United States Patent
Lee et al.

(10) Patent No.: US 10,417,763 B2
(45) Date of Patent: Sep. 17, 2019

(54) IMAGE PROCESSING APPARATUS, IMAGE PROCESSING METHOD, X-RAY IMAGING APPARATUS AND CONTROL METHOD THEREOF

(71) Applicant: SAMSUNG ELECTRONICS CO., LTD., Suwon-si (KR)

(72) Inventors: Ares Lee, Suwon-si (KR); Ki Jeong Oh, Bucheon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 14 days.

(21) Appl. No.: 15/651,782

(22) Filed: Jul. 17, 2017

(65) Prior Publication Data
US 2017/0316566 A1    Nov. 2, 2017

Related U.S. Application Data

(63) Continuation-in-part of application No. 14/808,419, filed on Jul. 24, 2015, now abandoned.

(30) Foreign Application Priority Data

Jul. 25, 2014    (KR) .......................... 10-2014-0095071

(51) Int. Cl.
*G06T 7/00* (2017.01)
*A61B 6/06* (2006.01)
*A61B 6/00* (2006.01)
*G06F 3/0484* (2013.01)
(Continued)

(52) U.S. Cl.
CPC .............. *G06T 7/0012* (2013.01); *A61B 6/06* (2013.01); *A61B 6/469* (2013.01); *A61B 6/5252* (2013.01);
(Continued)

(58) Field of Classification Search
CPC ................ G06T 7/0012; G06T 11/203; G06T 2207/10116; G06F 3/04842;
(Continued)

(56) References Cited

U.S. PATENT DOCUMENTS 7,916,142 B2    3/2011    Carroll
2001/0024200 A1    9/2001    Gupta et al.
(Continued)

FOREIGN PATENT DOCUMENTS

EP    0523771 A1    1/1993
KR    10-2013-0097491 A    9/2013

OTHER PUBLICATIONS

Search Report dated Oct. 20, 2015, issued by the International Searching Authority in counterpart International Application No. PCT/KR2015/007695.

*Primary Examiner* — Katrina R Fujita
(74) *Attorney, Agent, or Firm* — Sughrue Mion, PLLC

(57) ABSTRACT

An image processing apparatus includes a display configured to display a medical image; an input unit configured to receive n (n being an integer equal to or greater than three) number of input points with respect to the displayed medical image; and a controller configured to set a window in the medical image based on an area in a shape of a polygon, the area being defined by the input points, and to perform image processing of reducing at least one of brightness and definition of the medical image in a remaining area except for an area of the window.

24 Claims, 62 Drawing Sheets

(51) Int. Cl.
  *G06T 11/20* (2006.01)
  *A61B 6/03* (2006.01)
  *G21K 1/02* (2006.01)
  *G21K 1/04* (2006.01)
(52) U.S. Cl.
  CPC ............ *A61B 6/54* (2013.01); *G06F 3/04842* (2013.01); *G06F 3/04845* (2013.01); *G06T 11/203* (2013.01); *G21K 1/02* (2013.01); *G21K 1/046* (2013.01); *A61B 6/032* (2013.01); *A61B 6/461* (2013.01); *A61B 6/467* (2013.01); *A61B 6/488* (2013.01); *G06F 2203/04804* (2013.01); *G06F 2203/04808* (2013.01); *G06T 2207/10116* (2013.01)
(58) Field of Classification Search
  CPC ....... G06F 3/04845; G06F 2203/04804; G06F 2203/04808; A61B 6/032; A61B 6/06; A61B 6/361; A61B 6/369; A61B 6/5252; A61B 6/54
  See application file for complete search history.

(56) References Cited

U.S. PATENT DOCUMENTS

| | | |
|---|---|---|
| 2002/0151781 A1* | 10/2002 | Ohishi .................. A61B 6/466 600/407 |
| 2003/0156748 A1 | 8/2003 | Fang |
| 2003/0194057 A1 | 10/2003 | Dewaele |
| 2005/0119564 A1 | 6/2005 | Rosholm |
| 2006/0061595 A1 | 3/2006 | Goede et al. |
| 2007/0100226 A1 | 5/2007 | Yankelevitz |
| 2007/0116357 A1 | 5/2007 | Dewaele |
| 2007/0189589 A1 | 8/2007 | Fidrich |
| 2010/0194781 A1 | 8/2010 | Tossing et al. |
| 2012/0215095 A1* | 8/2012 | Av-Shalom .............. A61B 6/06 600/424 |
| 2014/0055462 A1 | 2/2014 | Hsu et al. |
| 2014/0093150 A1 | 4/2014 | Zalev |
| 2014/0181740 A1 | 6/2014 | Gachoka |
| 2018/0129896 A1* | 5/2018 | Wu .......................... A61B 6/06 |

* cited by examiner

IMAGE PROCESSING APPARATUS, IMAGE PROCESSING METHOD, X-RAY IMAGING APPARATUS AND CONTROL METHOD THEREOF

CROSS-REFERENCE TO RELATED APPLICATIONS

This application is a Continuation-In-Part of application Ser. No. 14/808,419, filed Jul. 24, 2015, which claims priority from Korean Patent Application No. 10-2014-0095071, filed on Jul. 25, 2014, in the Korean Intellectual Property Office, the disclosures of which are incorporated herein in their entireties by reference.

BACKGROUND

1. Field

Apparatuses and methods consistent with exemplary embodiments relate to an image processing apparatus, an image processing method, an X-ray imaging apparatus, and a control method for processing to improve clarity of a desired area of a medical image.

2. Description of the Related Art

Medical imaging apparatuses for imaging the inside of an object to diagnose the object include, for example, a radiation imaging apparatus to irradiate radiation onto the object and to detect radiation transmitted through the object, a magnetic resonance imaging (MRI) apparatus to apply high-frequency signals to the object located in a magnetic field and to receive MRI signals from the object, and an ultrasonic imaging apparatus to transmit ultrasonic waves to the object and to receive echo signals reflected from the object.

Since a medical image acquired by a medical imaging apparatus may include a lesion area or a background area other than an area that is to be diagnosed, shutter processing may be performed to render a user's desired area of the medical image appear clearly and the remaining area appear dark or blurry, to improve user convenience and visibility of images.

SUMMARY

One or more exemplary embodiments provide an image processing apparatus and an image processing method, which are capable of performing shutter processing with respect to a desired area through a user's intuitive and simple input operation.

Additional aspects of the disclosure will be set forth in part in the description which follows and, in part, will be obvious from the description, or may be learned by practice of the exemplary embodiments.

According to an aspect of an exemplary embodiment, there is provided an image processing apparatus including: a display configured to display a medical image; an input unit configured to receive n (n being an integer equal to or greater than three) number of input points with respect to the displayed medical image; and a controller configured to set a window in the medical image based on an area in a shape of a polygon, the area being defined by the input points, and to perform image processing of reducing at least one of brightness and definition of the medical image in a remaining area except for an area of the window.

The controller may be configured to set the window based on the area in the shape of the polygon having vertexes corresponding to the input points.

The controller may be configured to determine validity of the input points based on whether the input points define the area in the shape of the polygon.

In response to receiving an input point, the controller may be configured to determine validity of the input point, and when the controller determines that the input point is invalid, the controller may be configured to indicate a result of determining that the input point is invalid through the display.

When a distance between a first input point and a second input point among the input points is less than a reference distance, the controller may be configured to determine that an input point that is last input among the first input point and the second input point is invalid.

When at least three input points among the input points are on a straight line, the controller may be configured to determine that an input point that is last input among the at least three input points is invalid.

When n is equal to or greater than four and a figure defined by the input points has a concave shape, the controller may be configured to determine that an input point that is last input among the input points is invalid.

The controller may be configured to determine whether the figure defined by the input points has a concave shape based on whether an order in which a lastly input point among the input points is connected with previously input points is in a clockwise order or a counterclockwise order.

When the controller determines that the input point is invalid, the input unit may be configured to receive a new input point that replaces the input point that is determined to be invalid.

When the controller determines that all of the input points are valid, the controller may be configured to connect the input points to define the area in the shape of the polygon.

The controller may be configured to connect the input points such that straight lines connecting at least two input points among the input points do not cross each other.

The display may be configured to display the input point that is determined to be invalid to have at least one of a color and a shape that is different from at least one of a color and a shape of an input point that is determined to be valid.

The display may be configured to display the window on the medical image.

The display may be configured to display the medical image on which the image processing is performed.

The image processing apparatus may further include: a communicator configured to transmit the medical image on which the image processing is performed to an outside.

According to an aspect of another exemplary embodiment, there is provided an image processing apparatus including: a display configured to display a medical image; an input unit configured to receive n (n being an integer equal to or greater than one) number of input points with respect to the displayed medical image; and a controller configured to set a window in the medical image based on an area in a shape of a circle, the area being defined by the input points, and to perform image processing to reduce at least one of brightness and definition of the medical image in a remaining area except for an area of the window.

In response to receiving two input points through the input unit, the controller may be configured to set the window based on the area in the shape of the circle, the circle having a diameter or a radius corresponding to a straight line connecting the two input points.

In response to receiving an input point and a straight line starting from the input point through the input unit, the controller may be configured to set the window based on the area in the shape of the circle, the circle having a center point corresponding to the input point and a radius corresponding to the straight line.

In response to receiving an input point and a straight line starting from the input point through the input unit, the controller may be configured to set the window based on the area in the shape of the circle, the circle having a diameter corresponding to the straight line.

In response to receiving an input point through the input unit, the controller may be configured to set the window based on the area in the shape of the circle, the circle having a center point corresponding to the input point, and a radius of which length is determined in proportion to a time period during which an input of the input point is maintained.

The controller may be configured to set the window based on the area in the shape of the circle, the circle having a radius of which length is determined at a time when the input of the input point is stopped.

According to an aspect of another exemplary embodiment, there is provided an image processing method including: displaying a medical image on a display; receiving n (n being an integer equal to or greater than three) number of input points with respect to the displayed medical image; setting a window in the medical image based on an area in a shape of a polygon, the area being defined by the input points; and performing image processing to reduce at least one of brightness and definition of the medical image in a remaining area except for an area of the window area.

The setting may include setting the window based on the area in the shape of the polygon having vertexes corresponding to the input points.

The setting may include determining validity of the input points based on whether the input points define the area in the shape of the polygon.

The setting may include: determining, in response to receiving an input point, validity of the input point; and indicating, when it is determined that the input point is invalid, a result of determining that the input point is invalid through the display.

The determining may include determining, when a distance between a first input point and a second input point among the input points is less than a reference distance, that an input point that is last input among the first input point and the second input point is invalid.

The determining may include determining, when at least three input points among the input points are on a straight line, an input point that is last input among the at least three input points is invalid.

The determining may include determining, when a figure defined by the input points has a concave shape, that an input point that is last input among the input points is invalid.

The determining may include determining whether the figure defined by the input points has a concave shape based on whether an order in which a lastly input point among the input points is connected with previously input points is in a clockwise order or a counterclockwise order.

The image processing method may further include: receiving, in response to determining that the input point is invalid, a new input point that replaces the input point that is determined to be invalid.

The setting may include connecting, in response to determining that all of the input points are valid, the input points to define the area in the shape of the polygon.

The connecting may include connecting the input points such that straight lines connecting at least two input points among the input points do not cross each other.

The indicating may include displaying the input point that is determined to be invalid to have at least one of a color and a shape that is different from at least one of a color and a shape of an input point that is determined to be valid.

The image processing method may further include displaying the window on the medical image.

The image processing method may further include displaying the medical image on which the image processing is performed.

According to an aspect of another exemplary embodiment, there is provided an image processing method including: displaying a medical image on a display; receiving n (n being an integer equal to or greater than one) number of input point with respect to the displayed medical image; setting a window in the medical image based on an area in a shape of a circle, the area being defined based on the input point; and performing image processing to reduce at least one of brightness and definition of the medical image in a remaining area except for an area of the window.

The setting may include setting, in response to receiving two input points, the window based on the area in the shape of the circle, the circle having a diameter or a radius corresponding to a straight line connecting the two input points.

The setting may include, in response to receiving the input point and a straight line starting from the input point, setting the window based on the area in the shape of the circle, the circle having a center point corresponding to the input point and a radius corresponding to the straight line.

The setting may include, in response to receiving the input point and a straight line starting from the input point, setting the window based on the area in the shape of the circle, the circle having a diameter corresponding to the straight line.

The setting may include, in response to receiving the input point, setting the window based on the area in the shape of the circle, the circle having a center point corresponding to the input point, and a radius of which length is determined in proportion to a time period during which an input of the input point is maintained.

The setting may include, setting the window based on the area in the shape of the circle, the circle having a radius of which length is determined at a time when the input of the input point is stopped.

According to an aspect of another exemplary embodiment, there is provided an X-ray imaging apparatus including: a display configured to display an X-ray image; an input unit configured to receive n (n being an integer equal to or greater than three) number of input points with respect to the displayed X-ray image; and a controller configured to set a window in the medical image based on an area in a shape of a polygon, the area being defined by the input points, and to perform image processing to reduce at least one of brightness and definition of the medical image in a remaining area except for an area of the window.

The X-ray imaging apparatus may further include: an X-ray source configured to irradiate X-rays; and an X-ray detector configured to detect the X-rays and to acquire the X-ray image.

According to an aspect of another exemplary embodiment, there is provided an apparatus for processing a medical image, the apparatus including: a display configured to display a medical image; and a controller configured to: set a window in the medical image in a circular shape in response to a user input for designating a preset number of points or less in the medical image, and set the window in the medical image in a shape of a polygon in response to a user input for designating points greater than the preset number in the medical image, the polygon having vertexes corresponding to the points designated by the user input, wherein the controller is configured to perform image processing on the medical image based on the set window.

The controller may be configured to perform the image processing such that at least one of brightness and definition of the medical image is different between an area of the window and a remaining area of the medical image.

According to an aspect of an another exemplary embodiment, there is provided an image processing apparatus including: a collimator including a plurality of blades to form a collimation area, wherein at least one blade of the plurality of blades is rotatable in a clockwise direction or in a counterclockwise direction; a display configured to display a guide image; an input device configured to receive n (n being an integer equal to or greater than three) number of input points with respect to the displayed guide image; and a controller configured to set a polygon defined by the input points to a window area, and to control the collimator to form a collimation area corresponding to the window area.

The plurality of blades are configured to perform at least one movement of a rotational movement and a linear movement The controller may be configured to determine validity of the input points.

In response to receiving an input point, the controller may be configured to determine validity of the input point, and when the controller determines that the input point is invalid, the controller may be configured to display the result of that the input point is invalid through the display.

When a distance between a first input point and a second input point among input points is less than a reference value, the controller may be configured to determine that an input point that is last input among the first input point and the second input point is invalid.

When at least three input points of the input points are located on a straight line, the controller may be configured to determine that an input point that is last input among the at least three input points is invalid.

When a figure defined by the input points has a concave shape, the controller may be configured to determine that an input point that is last input among the input points is invalid.

The controller may be configured to determine whether the figure defined by the input points has a concave shape based on whether an order in which a lastly input point among the input points is connected with previously input points is in a clockwise order or a counterclockwise order.

When the controller determines that the input point is invalid, the input device may be configured to receive a new input point that replaces the input point that is determined to be invalid.

When the controller determines that all of the input points are valid, the controller may be configured to connect the input points to define the area in the shape of the polygon.

The guide image includes at least one image among an X-ray image acquired by irradiating a low dose of X-rays on an object before main scanning, a camera image acquired by photographing the object with a camera, and a previously acquired X-ray image of the object.

The controller may be configured to determine whether the collimator is able to form a collimation area having a polygon shape defined by the input points.

When the controller determines that the collimator is unable to form the collimation area having the polygon shape defined by the input points, the controller may be configured to control the collimator to form a collimation area of a shape most similar to the polygon.

When the controller determines that the collimator is unable to form the collimation area having the polygon shape defined by the input points, the controller may be configured to control the collimator to perform image processing on the acquired X-ray image.

The controller may be configured to perform the image processing in such a way to reduce brightness or definition of the remaining area except for the window area in the acquired X-ray image or to cut off the remaining area.

According to an aspect of an another exemplary embodiment, there is provided an image processing apparatus including: a collimator including a plurality of blades to form a collimation area, wherein at least one blade of the plurality of blades is rotatable in a clockwise direction or in a counterclockwise direction; a display configured to display a guide image; an input device configured to receive n points for the guide image, the n points input by a user, wherein n is an integer that is equal to or greater than 1; and a controller configured to set a circle defined by the input points to a window area, to control the collimator to form a collimation area corresponding to the window area, and to perform image processing on an X-ray image acquired by X-rays passed through the collimation area to acquire an X-ray image corresponding to the window area.

When two points are input through the input device, the controller may be configured to set a circle whose diameter or radius is a straight line connecting the two points, to the window area.

When a point and a straight line starting from the point are input through the input device, the controller may be configured to set a circle whose center point is the point and whose radius is the straight line, to the window area.

When a point and a straight line starting from the point are input through the input device, the controller may be configured to set a circle whose diameter is the straight line, to the window area.

When a point is input through the input device, the controller may be configured to create a circle whose center point is the input point, and increase a radius of the circle in proportion to a time period for which the point is input.

The controller may be configured to set a circle having a radius acquired at time at which the point is no longer input, to the window area.

The plurality of blades may be configured to perform at least one movement of a rotational movement and a linear movement.

According to an aspect of another exemplary embodiment, there is provided a method of controlling an X-ray imaging apparatus including: displaying a guide image on a display; receiving n points for the guide image, the n points input by a user, wherein n is an integer that is equal to or greater than 3; and setting a polygon defined by the input points to a window area, and controlling a collimator including a plurality of blades to form a collimation area corresponding to the window area, wherein at least one blade of the plurality of blades is rotatable in a clockwise direction or in a counterclockwise direction.

The method of controlling an X-ray imaging apparatus further comprises determining whether the collimator is able to form a collimation area having a polygon shape defined by the input points.

The controlling of the collimator comprises: when the collimator is unable to form the collimation area having the polygon shape defined by the input points, controlling the collimator to form a collimation area of a shape most similar to the polygon; and controlling the collimator to perform image processing on an acquired X-ray image.

According to an aspect of another exemplary embodiment, there is provided a method of controlling an X-ray imaging apparatus including: displaying a guide image on a display; receiving n points for the guide image, the n points input by a user, wherein n is an integer that is equal to or greater than 1; and setting a circle defined by the input points to a window area; controlling a collimator including a plurality of blades to form a collimation area corresponding to the window area, wherein at least one blade of the plurality of blades is configured to be rotatable in a clockwise direction or in a counterclockwise direction; and performing image processing on an X-ray image acquired by X-rays passed through the collimation area to acquire an X-ray image corresponding to the window area.

BRIEF DESCRIPTION OF THE DRAWINGS

The above and/or other aspects will become more apparent by describing certain exemplary embodiments with reference to the accompanying drawings in which.

DETAILED DESCRIPTION

Figure 1:
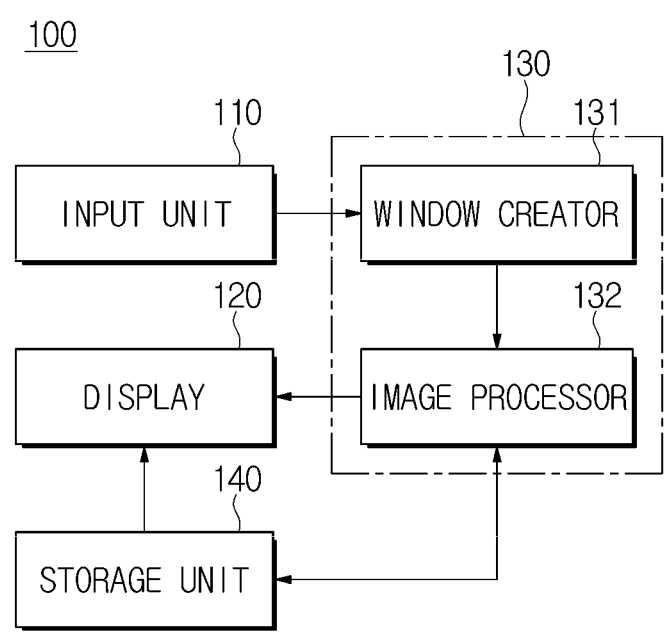
FIG. 1 is a control block diagram of an image processing apparatus according to an exemplary embodiment.

Reference will now be made in detail to exemplary embodiments, examples of which are illustrated in the accompanying drawings, wherein like reference numerals refer to like elements throughout.

Hereinafter, exemplary embodiments of an image processing apparatus and an image processing method according to an inventive concept will be described in detail.

Shutter processing that is performed according to the exemplary embodiments of the image processing apparatus and the image processing method does not mean physically adjusting a range of scanning in acquiring an image, but means enhancing a desired area of an already created image by rendering a remaining area except for the desired area appear dark or blurry. In the following description, the desired area enhanced by the shutter processing will be referred to as a window or a window area.

Figure 2:
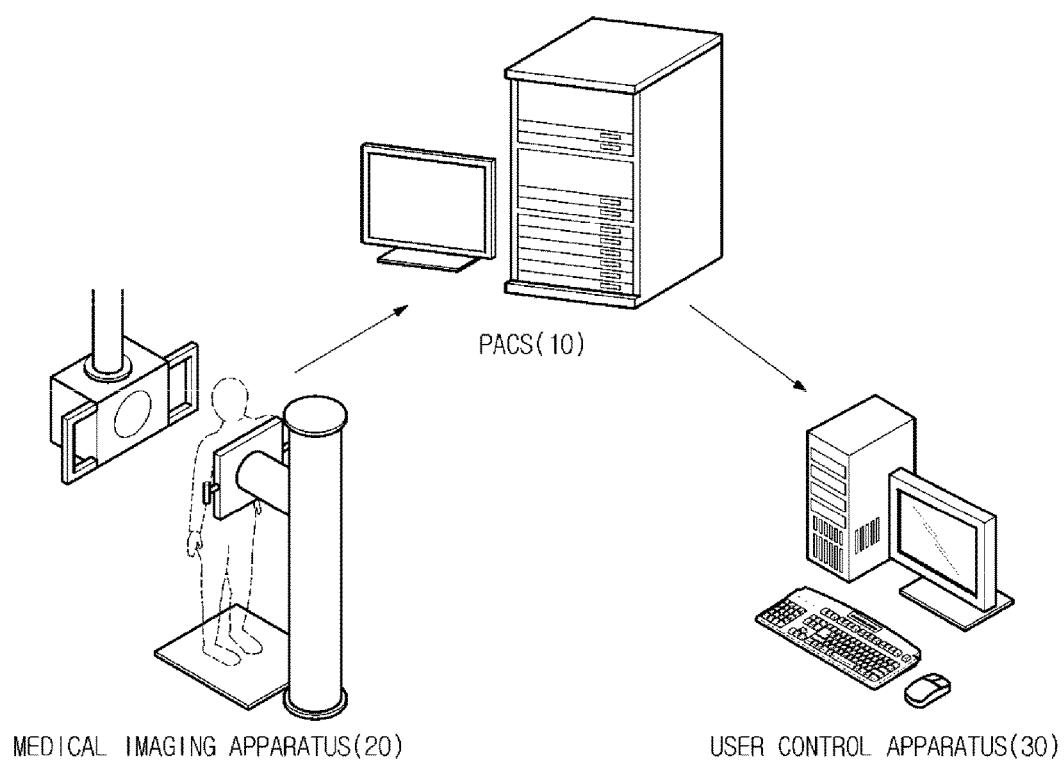
FIG. 2 is a view for describing a process of transmitting medical images.

FIG. 1 is a control block diagram of an image processing apparatus according to an exemplary embodiment, and FIG. 2 is a view for describing a process of transmitting medical images.

Referring to FIG. 1, an image processing apparatus according to an exemplary embodiment may include an input unit 110 to receive a user's selection for forming a shutter, a display 120 to display medical images, a controller 130 to control overall operations of the image processing apparatus 100, and a storage unit 140 to store medical images subject to shutter processing.

If a medical image is displayed on the display 120, a user may select a desired area (for example, an area including lesions or an area to be diagnosed) of the displayed medical image through the input unit 110. At this time, the user may select the desired area, for example but not limited to, using a method of inputting three points or more.

A window creator 131 of the controller 130 may determine whether the user's input is valid. Details about operations in which an area is selected by the user and the controller 130 determines validity of the selected area will be described later.

If the window creator 131 determines that the user's input is valid, the window creator 131 may set the area selected by the user to a window.

Then, an image processor 132 may perform shutter processing on the image displayed on the display 120. That is, the image processor 132 may reduce the brightness or definition of the remaining area except for the area set to the window in the image displayed on the display 120. The shutter-processed image may be stored in the storage unit 150.

The medical image that is displayed or processed by the image processor 132 may be a radiation image, a magnetic resonance (MR) image, or an ultrasonic image.

The radiation image may include a positron emission tomography (PET) image and an X-ray image acquired by irradiating X-rays onto an object and detecting X-rays transmitted through the object, wherein the X-ray image may include a general X-ray projected image and an X-ray tomography image acquired by imaging a section of an object. The X-ray projected image may be acquired by an imaging apparatus, such as general radiography and mammography, according to the kind of an object. The X-ray tomography image may be acquired by an imaging apparatus, such as computerized tomography (CT) and tomosynthesis.

However, the above-mentioned medical images are examples of medical images that can be displayed or processed by the image processing apparatus 100, and the kinds of medical images that can be displayed and processed by the image processing apparatus 100 according to an exemplary embodiment are not limited.

Generally, before a patient is scanned to acquire a medical image, the patient may consult with a doctor to explain his or her symptoms or show his or her affected area, and the doctor may decide an area to be scanned according to the patient's state to issue a scanning order. The doctor's scanning order may be transmitted to a central server of a medical institution, and the central server may transmit the doctor's scanning order to a medical imaging apparatus to acquire a medical image according to the scanning order. At this time, scanning the patient to acquire a medial image may be performed by a radiological technologist or a doctor.

As shown in FIG. 2, if a medical image is acquired by a medical imaging apparatus 20, the medical image may be transmitted to a central server 10 of a medical institution thought a network. For example, the central server 10 may be a picture archiving communication system (PACS), and the PACS 10 may store and manage the received medical image.

A user (for example, a doctor) who wants to check a medical image may use the PACS 10 to search for a desired medical image. The PACS 10 may, in addition to a database to store medical images, include various kinds of processors and a user interface, such as an input unit and a display. Accordingly, the user can search for and check a desired medical image though the user interface, and edit the searched medical image as needed.

Medical images stored in the PACS 10 may be searched by using a user control apparatus 30. The user control apparatus 30 may include a personal computer that can be used by a user such as a doctor. Accordingly, the user may use the user control apparatus 30 to search for a desired medical image in medical images stored in the PACS 10, without directly accessing the PACS 10.

The user may perform shutter processing on the medical image using any one of the medical imaging apparatus 20, the PACS 10, and the user control apparatus 30. Accordingly, the image processing apparatus 100 may be included in the medical imaging apparatus 20, the PACS 10, or the user control apparatus 30.

Figure 3:
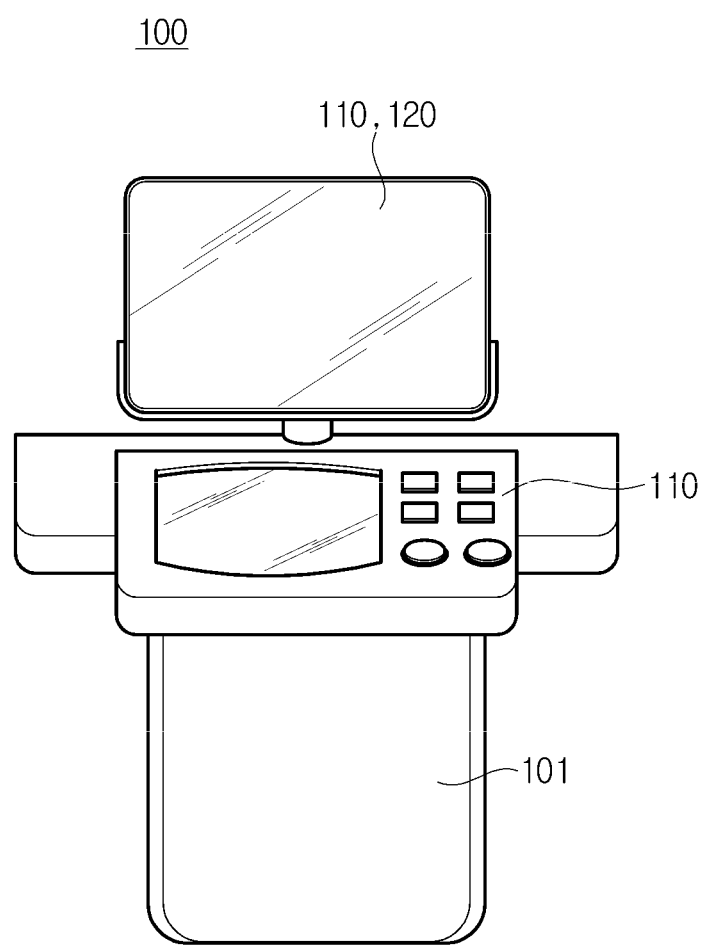
FIGS. 3 and 4 show external appearances of image processing apparatuses according to exemplary embodiments.
Figure 4:
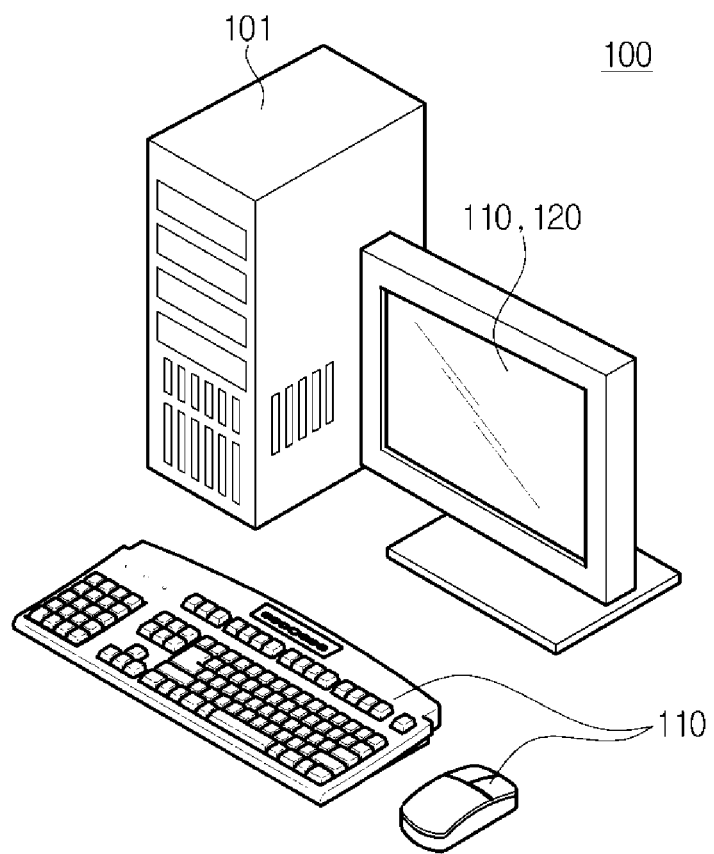

FIGS. 3 and 4 show external appearances of image processing apparatuses according to exemplary embodiments.

For example, if the image processing apparatus 100 is included in the medical imaging apparatus 20, the image processing apparatus 100 may include a workstation shown in FIG. 3. The workstation includes an apparatus that receives a user's commands for controlling the medical imaging apparatus 20 or processes medical image data to create and display visible medical images, independently from a configuration of scanning an object to acquire medical image data. The workstation is also called a host apparatus or a console, and may include any apparatus capable of storing and processing medical image data acquired by the medical image apparatus 20.

The display 120 may be a liquid crystal display (LCD), a light emitting diode (LED) display, or an organic light emitting diode (OLED) display.

The input unit 110 may include one or more keys or buttons that can be manipulated by applying pressure thereto, a trackball or a mouse that can be manipulated by moving its location, and a touch panel that can be manipulated by a user's touch input. If the input unit 110 includes a touch panel, the input unit 110 may be implemented as a touch screen by mounting a transparent touch panel on a side of the display 120, or may be provided separately from the display 120.

Although not shown in FIG. 3, the controller 130 and the storage unit 140 may be installed in a main body 101. The controller 130 may be implemented as a processor or controller, such as a central processor unit (CPU), a micro controller unit (MCU), or a micro processor unit (MPU). The storage unit 140 may include at least one of an integrated circuit (IC) memory (for example, a read only memory (ROM), a random access memory (RAM), or a flash memory), a magnetic memory (for example, a hard disk or a diskette drive), and an optical memory (for example, an optical disk).

The window creator 131 and the image processor 132 of the controller 130 may be implemented as physically separated devices, however, a part of functions of the window creator 131 and the image processor 132 may be performed by one device or one chip. Also, the storage unit 140 and the controller 130 may be implemented on one chip.

The external appearance of the image processing apparatus 100 in a case where the image processing apparatus 100 is included in a workstation may be different from that of the image processing apparatus 100 of FIG. 3. That is, FIG. 3 shows only an example of the external appearance of the image processing apparatus 100. Also, the image processing apparatus 100 is not required to perform all operations of a general workstation. That is, the image processing apparatus 100 may only need to perform operations of the input unit 110, the display 120, the controller 130, and the storage unit 140 which are described above or will be described later.

As another example, if the image processing apparatus 100 is included in the user control apparatus 30, the image processing apparatus 100 may have an external appearance as described in FIG. 4. The display 120 may be a monitor of a personal computer, and the input unit 110 may be a keyboard and/or a mouse. Also, in an alternative example, the input unit 110 may be a touch panel to form a touch screen together with the display 120, as described above.

Although not shown in the drawings, the controller 130 and the storage unit 140 may be installed in the main body 101, and repetitive descriptions about the controller 130 and the storage unit 140 will be omitted.

Also, in a case where the image processing apparatus 100 is included in the user control apparatus 30, the external appearance of the image processing apparatus 100 may be different from that of the image processing apparatus 100 of FIG. 4. That is, FIG. 4 shows only an example of the external appearance of the image processing apparatus 100. Also, the image processing apparatus 100 is not required to perform all operations of a general workstation. That is, the image processing apparatus 100 may only need to perform operations of the input unit 110, the display 120, the controller 130, and the storage unit 140 which are described above or will be described later.

In the above, the basic configuration and external appearance of the image processing apparatus 100 have been described. Hereinafter, a method of performing shutter processing on a medical image according to a user's input will be described in detail. For convenience of description, a medical image which is used in the following embodiments is assumed to be an X-ray image. However, it should be noted that the exemplary embodiments are not limited thereto. For example, the medical image may be a magnetic resonance (MR) image, or an ultrasonic image.

Figure 5:
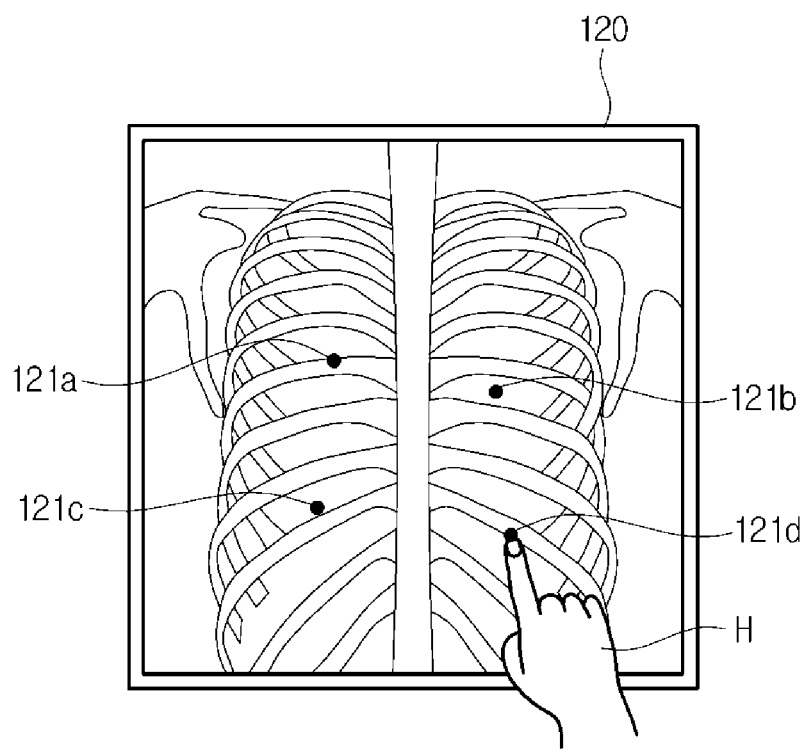
FIGS. 5 and 6 are views for describing examples of methods of receiving inputs of desired points when performing shutter processing on a medical image according to exemplary embodiments.
Figure 6:
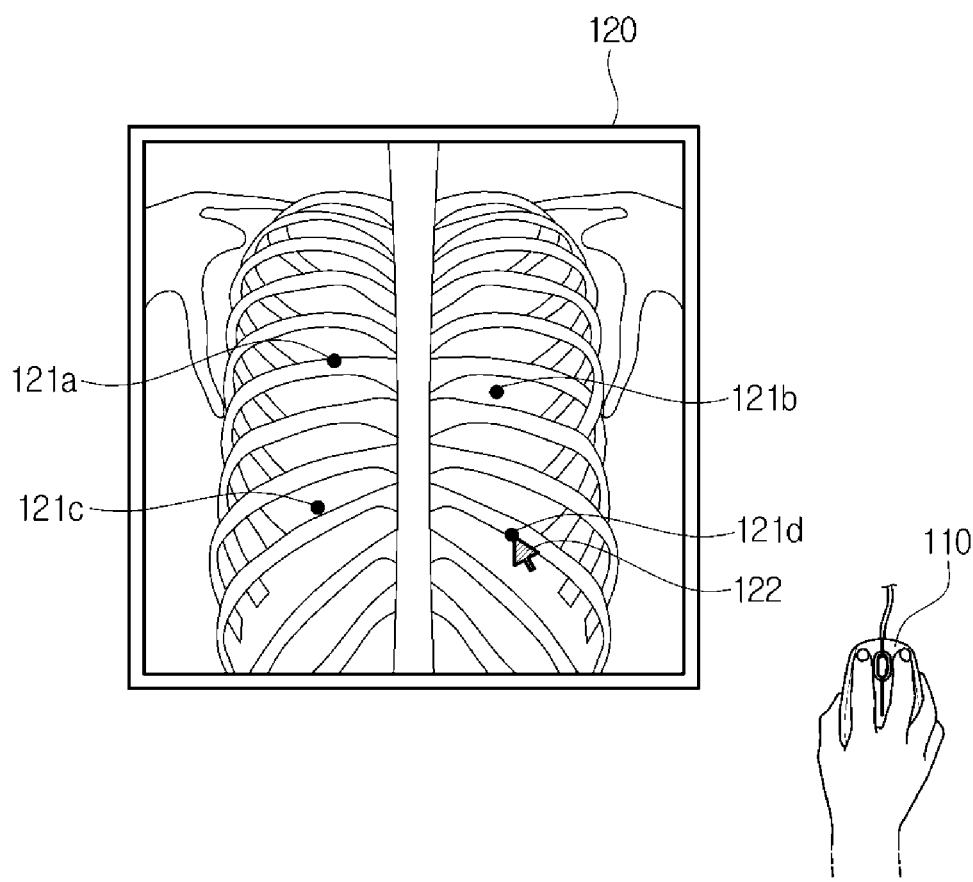
Figure 7:
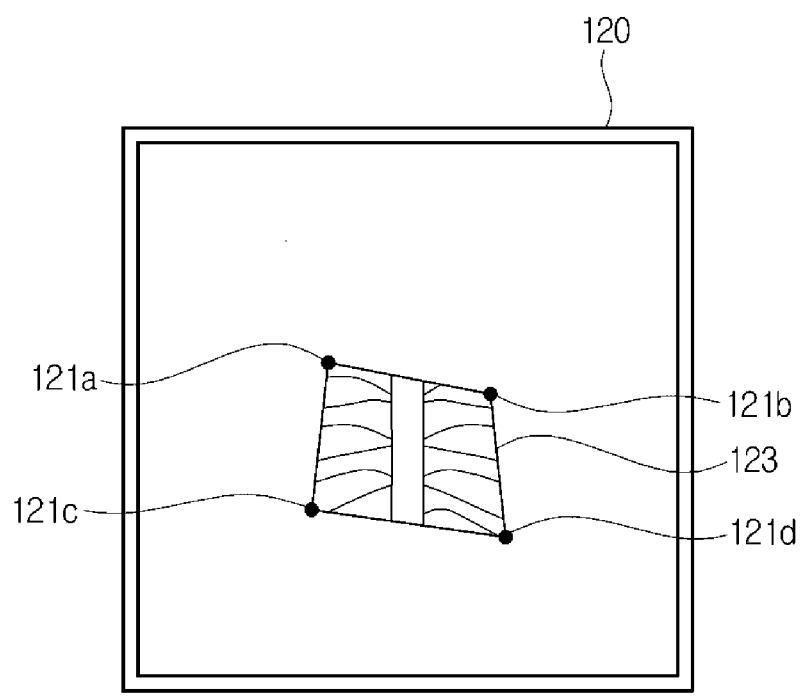
FIG. 7 shows a result of shutter processing performed by an image processing apparatus according to an exemplary embodiment.

FIGS. 5 and 6 are views for describing examples of methods of receiving inputs of desired points when performing shutter processing on a medical image in the image processing apparatus 100 according to exemplary embodiments, and FIG. 7 shows a result of shutter processing performed by the image processing apparatus 100 that receives the user inputs of four points.

The image processing apparatus 100 according to an exemplary embodiment may display a medical image on the display 120, and if a user selects a desired area from the displayed medical image, the image processing apparatus 100 may set the selected area to a window area, and then perform shutter processing.

At this time, by allowing a user to intuitively select a window area, it is possible to improve user convenience and the accuracy of window area setting. For example, the image processing apparatus 100 may receive all vertexes of a polygon that is to be formed as a window, from a user.

That is, the image processing apparatus 100 may allow a user to input n points (wherein n is an integer number greater than or equal to 3) on a medical image displayed on the display 120. In FIGS. 5 and 6, an example in which n is 4 is shown. Herein, the user may be a radiological technologist or a doctor although not limited to them.

Referring to FIG. 5, when the input unit 110 is implemented as a transparent touch panel to configure a touch screen together with the display 120, a user may use his or her hand H to touch desired four points 121a, 121b, 121c, and 121d on a medical image displayed on the display 120 to be entered. In this case, the image processing apparatus 100 may display the four points 121a, 121b, 121c, and 121d on the display 120 in order for the user to be able to check the points 121a, 121b, 121c, and 121d selected by the user.

Referring to FIG. 6, when the input unit 110 is implemented as a mouse, a pointer 122 moving on the display 120 according to a movement amount and a direction of the input unit 110 may be displayed. A user may manipulate the input unit 110 to locate the pointer 122 at locations corresponding to the four points 121a, 121b, 121c, and 121d on the medical image, and then click the input unit 110, thereby inputting the fourth points 121a, 121b, 121c, and 121d.

However, the methods of inputting points as shown in FIGS. 5 and 6 are only examples that can be applied to the image processing apparatus 100. According to another example, a user can input desired points using a trackball or a keyboard.

If the four points 121a, 121b, 121c, and 121d are input using any one of the above-described methods, a window 123 having the shape of a quadrangle that is defined by the four points 121a, 121b, 121c, and 121d, that is, a quadrangle whose vertexes are the four points 121a, 121b, 121c, and 121d may be created, and the remaining area except for the window 123 in the medical image displayed on the display 120 may be processed to appear dark or blurry. In this way, shutter processing of highlighting only the area included in the window 123 may be performed. Although FIG. 7 illustrates only an image in the area included in the window 123 is shown on the display, it should be understood that the image outside the window 123 that is processed to appear dark or blurry may be shown.

The shutter-processed image may be stored in the storage unit 140, and the original medical image not subject to the shutter processing may also be stored in the storage unit 140.

In the examples of FIGS. 5 and 6, since the user inputs all of the four points 121a through 121d defining the window 123, the window 123 having a desired shape may be created. In another example, if two points are input to create a window in a shape of a quadrangle, the two points may be used to define the diagonal vertexes of a rectangle and a rectangular window may be created based on the diagonal vertexes, instead of other quadrangles, such as a trapezoid, a diamond, and a parallelogram.

If the user wants to edit the window 123, the user may execute a window editing menu, directly edit the window 123 without executing the window editing menu, or again input n points. First, an example of directly editing the window 123 without executing the window editing menu will be described.

Figure 8:
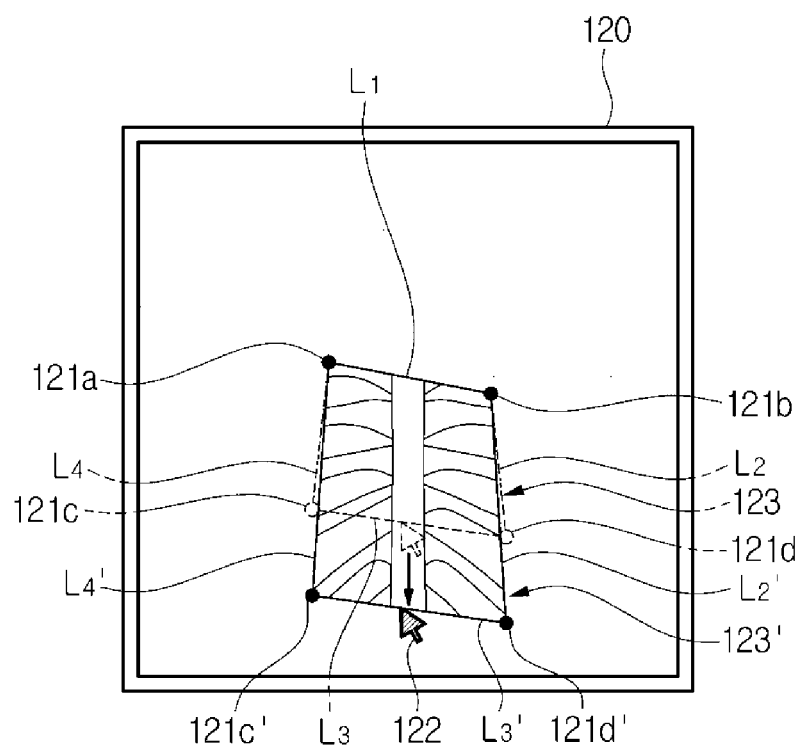
FIGS. 8, 9, and 10 are views for describing operation of editing a created window according to exemplary embodiments.
Figure 9:
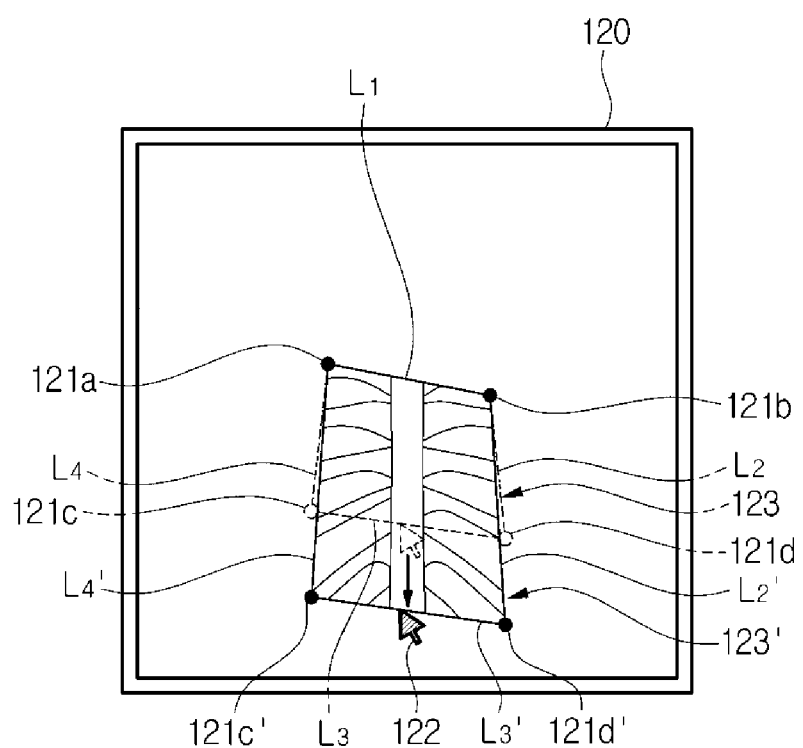
Figure 10:
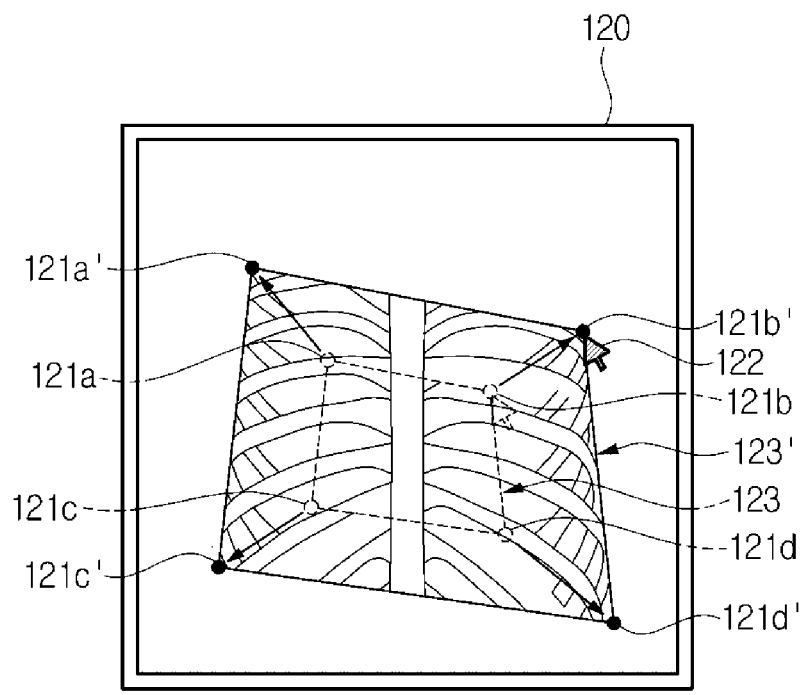

FIGS. 8, 9, and 10 are views for describing operation of editing the created window 123 according to exemplary embodiments.

After the window 123 is created and displayed on the display 120 as shown in FIG. 7, the user can change the shape or size of the window 123 without executing an editing menu.

For example, the user may select and move at least one point 121b among the four points 121a, 121b, 121c, and 121d defining the window 123, as shown in FIG. 8. In FIG. 8, an example in which the point 121b is moved by the movement of the pointer 122 displayed on the display 120 is shown. In this case, the input unit 110 may be a mouse, and the user may manipulate the mouse 110 to move the point 121b to a desired location 121b'. However, this operation is only an example of moving the point 121b, and if the input unit 110 is a touch panel, the user may move the point 121b by a touch operation, e.g., touching and dragging the point 121b.

When the point 121b moves to the desired location 121b' having new coordinates, the resultant four points 121a, 121b', 121c, and 121d may define a new window 123' having a shape and a size that are different from those of the previous window 123.

As another example, as shown in FIG. 9, a user may move at least one line $L_3$ among lines $L_1, L_2, L_3,$ and $L_4$ connecting the points 121a, 121b, 121c, and 121d to each other, respectively. The user may select the line $L_3$ through the input unit 110 to move the line $L_3$ to a desired location. The selected line $L_3$ moved to the desired location may change to a new line $L_3'$, and due to the movement of the selected line $L_3$, the lines $L_2$ and $L_4$ may change to form new lines $L_2'$ and $L_4'$, respectively. Accordingly, the resultant four lines $L_1, L_2', L_3',$ and $L_4'$ may define another window 123' having a shape and a size that are different from those of the previous window 123.

When the window 123 is edited, validity of input may be determined. For example, in the example as shown in FIG. 8, validity of an input of the new point 121b' to move the point 121b may be determined, and if it is determined that the input of the new point 121b' is invalid, a new input may be received from the user.

After the new window 123' is created, the image processor 132 may perform shutter processing with respect to the new window 123'. At this time, the image processor 132 may use the original medical image stored in the storage unit 140. The image processor 132 may reduce the brightness or definition of the remaining area except for the new window 123' in the original medical image. Then, the display 120 may display the resultant image acquired by performing shutter processing with respect to the new window 123'.

In an exemplary embodiment, editing of enlarging or reducing the size of a window while maintaining the shape of the window is also possible. As shown in FIG. 10, if a point 121b among points 121a, 121b, 121c, and 121d displayed on the display 120 is selected and moved, an enlargement/reduction magnification of a window may be determined according to a movement amount and a direction of the point 121b, and all or a part of the remaining points 121a, 121c, and 121d may move according to the determined enlargement/reduction magnification so that new points 121a', 121b', 121c' and 121d' may be generated.

In this example, all of the four points 121a, 121b, 121c, and 121d are moved according to the movement of the point 121b, however, the exemplary embodiments are not limited thereto. For example, if enlargement or reduction is performed only in the movement direction of the selected point 121b according to the determined an enlargement/reduction magnification, the point 121d may remain at a fixed position.

If the window 123 is enlarged or reduced to the window 123', the image processor 132 may perform shutter processing with respect to the enlarged or reduced window 123', and display the result of the shutter processing on the display 120.

As described above, a user may select and move a point and/or line of the created window 123 to thereby edit the window 123 without executing an editing menu.

When a user selects an area in the window 123, instead of a point or a line of the window 123, the window creator 131 may recognize the selection as an input of a new point. That is, if a user selects an area in the window 123 that does not correspond to a point or a line of the window 123 after the shutter-processed medical image including the window 123 is displayed on the display 120, the window creator 131 may recognize that n points are input to create a new window.

Figure 11:
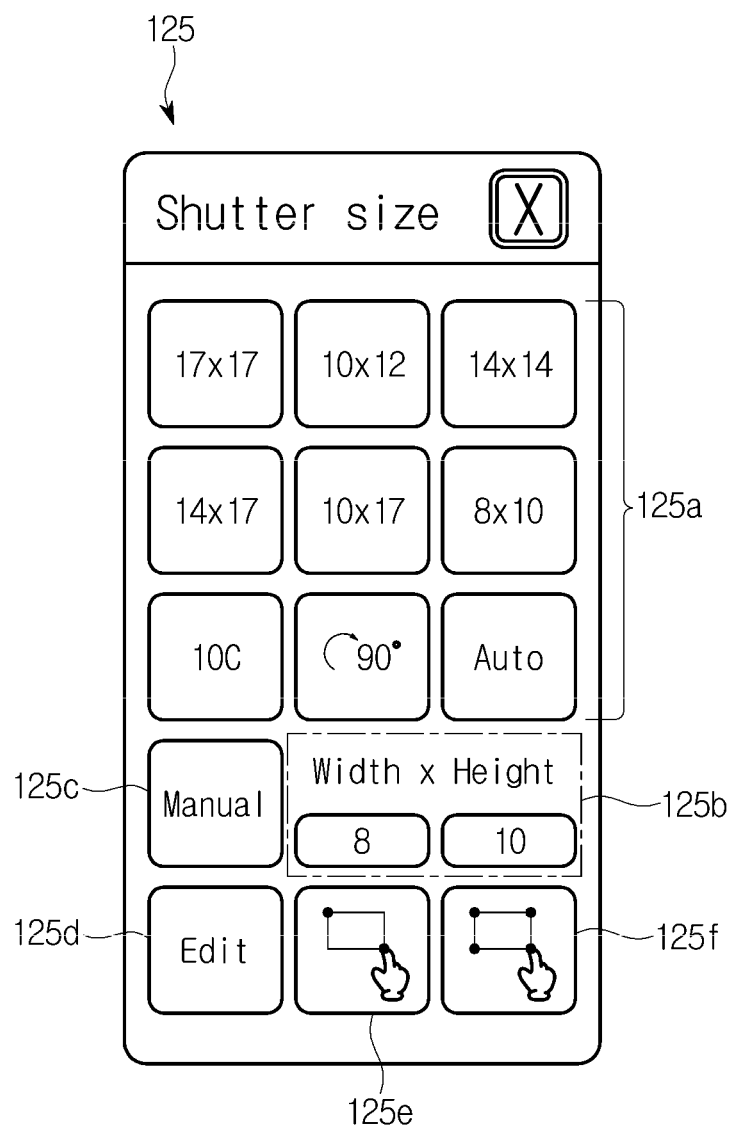
FIG. 11 shows an example of a graphic user interface that can be used for setting a window according to an exemplary embodiment.

FIG. 11 shows an example of a graphic user interface that can be used for window setting according to an exemplary embodiment.

If the image processing apparatus 100 executes a shutter function, the display 120 may display a graphic user interface (GUI) 125 as shown in FIG. 11. In the following exemplary embodiments, the GUI 125 that can be used for window setting will be referred to as a window setting menu.

Referring to FIG. 11, the window setting menu 125 may include icons 125a to adjust the size of a window to a predetermined size, icons 125b and 125c to manually input the size of a window, and an icon 125d to edit a set window.

In the examples of FIGS. 8, 9, and 10, operation of directly editing the window 123 without executing an editing menu has been described, however, the window 123 can be edited by selecting the icon 125d for editing a window to execute an editing menu.

Also, the window setting menu 125 may include an icon 125f to set a window in a shape of a quadrangle by inputting four points, and an icon 125e to set a window in a shape of a quadrangle by inputting two points, as needed.

If a user uses the input unit 110 to select the icon 125f, the input unit 110 may enter a state (e.g., standby state) to receive an input of four points, and if a point is input through the input unit 110, the controller 130 may determine whether the input point is valid. This operation will be described in detail, below.

Figure 12A:
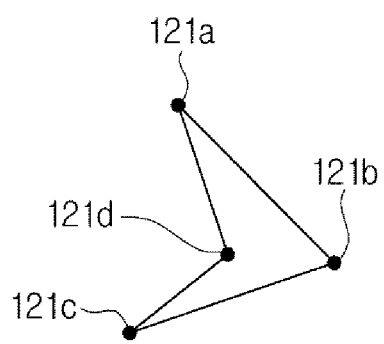
FIGS. 12A, 12B, and 12C show examples of invalid point inputs.
Figure 12B:
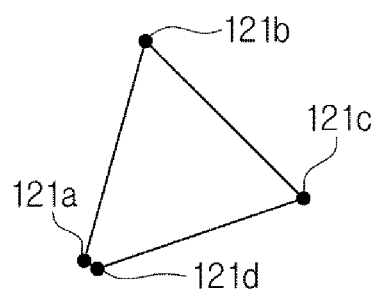
Figure 12C:
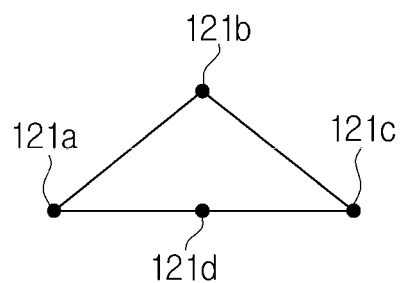
Figure 13:
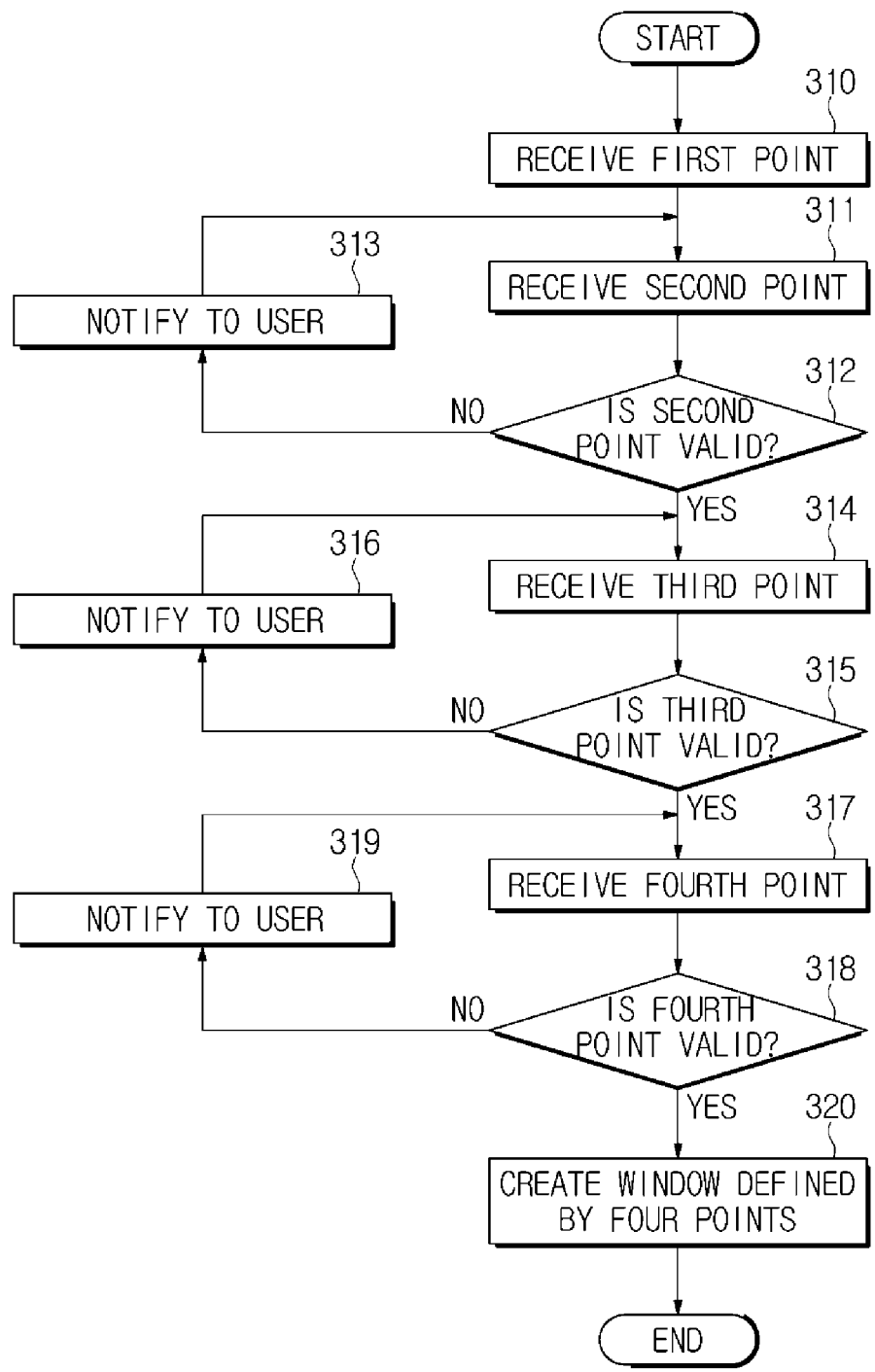
FIG. 13 is a flowchart illustrating a method of determining validity of input points according to an exemplary embodiment.

FIG. 12 shows examples of invalid point inputs, FIG. 13 is a flowchart illustrating a method in which the controller 130 determines validity of input points according to an exemplary embodiment, and FIGS. 14 and 15 are views for describing an example of a method of determining whether a concave polygon is formed by input points according to exemplary embodiments.

If a figure defined by four points input to set a window of a quadrangle is not a quadrangle or is a concave quadrangle, it may be determined that the input points are invalid.

For example, as shown in FIG. 12A, if at least one of the internal angles of a quadrangle formed by connecting four input points 121a, 121b, 121c, and 121d to each other is 180 degrees or more, the quadrangle may be determined to be a concave quadrangle, and the controller 130 may determine that the input points 121a, 121b, 121c, and 121d are invalid.

Also, as shown in FIG. 12B, if a distance between at least two points 121a and 121d among input points 121a, 121b, 121c, and 121d is shorter than a reference distance, the controller 130 may determine that the input points 121a, 121b, 121c, and 121d are invalid.

Also, as shown in FIG. 12C, if three points 121a, 121c, and 121d or more of input points 121a, 121b, 121c, and 121d are on a straight line, the controller 130 may determine that the input points 121a, 121b, 121c, and 121d are invalid.

Points input by a user may have information of two dimensional (2D) spatial coordinates. Accordingly, when the controller 130 or the image processor 132 determines or processes points in the following exemplary embodiments, the controller 130 or the image processor 132 may use the 2D spatial coordinates of the corresponding points.

Hereinafter, a method of determining validity of points will be described in detail with reference to FIG. 13.

Referring to FIG. 13, a first point of four points may be received, in operation 310. In the flowchart of FIG. 13, the order of "first", "second", "third", and "fourth" represents the order in which points are input, regardless of the order in which input points are connected to create a figure.

Since the validity of input points cannot be determined using only the first point, a second point may be received, in operation 311.

After the second point is received, the validity of the input point may be determined, in operation 312.

More specifically, it may be determined whether a distance between the first point and the second point is longer than a reference distance. For example, if the reference distance has been set to 5 mm, it may be determined that the second point is valid if the second point is spaced 5 mm or more apart from the first point ("Yes" in operation 312), and otherwise, it may be determined that the second point is invalid ("No" in operation 312).

If it is determined that the second point is invalid, a second point may be again received, in operation 311. To again receive the second point, it may be notified to a user that the second point is invalid, in operation 313. To notify the user of the invalidity of the second point, various methods such as, for example, a method of flickering the second point displayed on the display 120 flicker, a method of displaying the second point with a color and/or a shape that is different from that of the first point, a method of displaying a message informing that the second input is invalid, and a method of providing acoustic feedback, e.g., outputting warning sound. Also, a method of providing haptic feedback, e.g., transferring vibration signals to a user through the input unit 110 may be used.

If it is determined that the second point is valid ("Yes" in operation 312), a third point may be received, in operation 314. Then, it may be determined whether the third point is valid, in operation 315.

More specifically, if the third point is located on a straight line connecting the first point to the second point or on an extension line of the straight line connecting the first point to the second point although the third point is spaced apart from the first and second points by the reference distance or more, no quadrangle can be formed regardless of validity of a fourth point.

Accordingly, the controller 130 may determine whether the third point is spaced the reference distance or more apart from both the first and second points, and whether the first point, the second point, and the third point are on a straight line.

To determine whether the three points are on a straight line, for example, the controller 130 may use a function of calculating a distance between a straight line formed by two points and the remaining point. If a distance calculated by the function is short than the reference distance, the controller 130 may determine that the three points are on a straight line.

If the controller 130 determines that the third point is not spaced the reference distance or more apart from at least one of the first point and the second point, or that the first point, the second point, and the third point are on a straight line, the controller 130 may determine that the third point is invalid ("No" in operation 315).

Then, the controller 130 may notify the user that the third point is invalid, in operation 316, and a third point may be again received.

When the controller 130 determines that the third point is spaced the reference distance or more apart from both the first point and the second point, and that the first point, the second point, and the third point are not on a straight line, the controller 130 may determine that the third point is valid ("Yes" in operation 315).

Then, a fourth point may be received, in operation 317, and the controller 130 may determine whether the fourth point is valid, in operation 318.

To determine the validity of the fourth point, the controller 130 may determine whether the fourth point is spaced the reference distance or more apart from at least one of the first, second, and third points, whether the first point, the second point, and the fourth point are on a straight line, whether the first point, the third point, and the fourth point are on a straight line, or whether the second point, the third point, and the fourth point are on a straight line. If at least one of the above-mentioned conditions is satisfied, the controller 130 may determine that the fourth point is invalid.

In addition, the controller 130 may determine whether any one of the internal angles of a figure defined by the four points is 180 degrees or more. In this manner, whether a figure defined by the four points is a concave quadrangle is determined. If the controller 130 determines that a figure defined by the four points is a concave quadrangle, the controller 130 may determine that the fourth point is invalid.

More specifically, the controller 130 may use a function (for example, an IsCW function) of determining whether an arrangement order of points (i.e., an order in which each point is connected to another point) is a clockwise order or a counterclockwise order to determine whether the fourth point is valid.

Figure 14A:
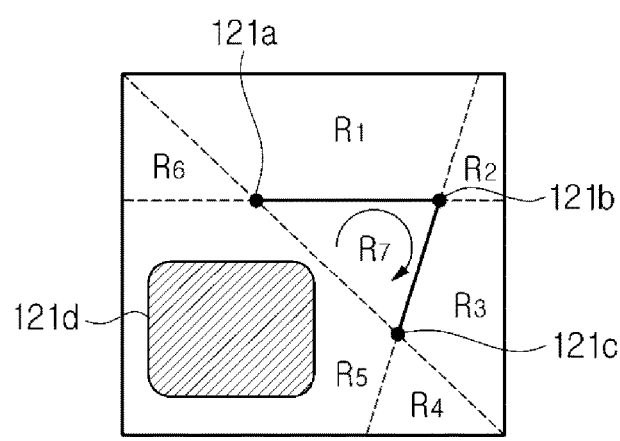
FIGS. 14A, 14B, 14C, 14D, 15A, 15B, 15C, and 15D are views for describing a method of determining whether a concave polygon is formed by input points according to exemplary embodiments.

For example, FIGS. 14A, 14B, 14C, and 14D illustrate a first point 121a, a second point 121b, and a third point 121c, which are arranged is a clockwise order. In this case, as shown in FIG. 14A, if an arrangement order of the first point 121a, the second point 121b, and a fourth point 121d is a clockwise order, an arrangement order of the first point 121a, the third point 121c, and the fourth point 121d is a clockwise order, and an arrangement order of the second point 121b, the third point 121c, and the fourth point 121d is a clockwise order, that is, if the fourth point 121d is located in an $R_5$ area, the controller 130 may determine that a figure defined by the four points 121a, 121b, 121c, and 121d is not a concave quadrangle.

Figure 14B:
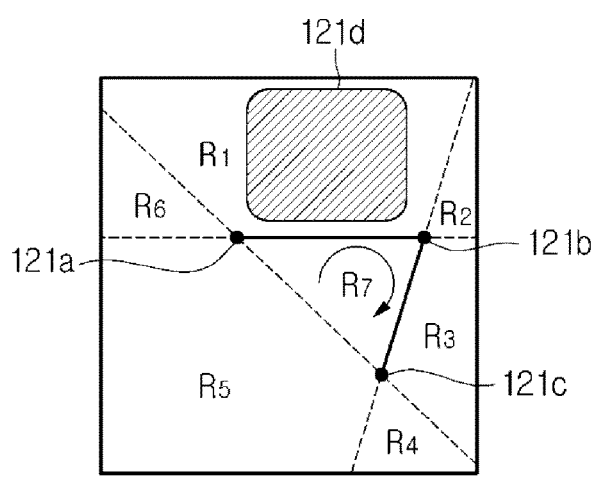

Also, as shown in FIG. 14B, if an arrangement order of the first point 121a, the second point 121b, and the fourth point 121d is a counterclockwise order, an arrangement order of the first point 121a, the third point 121c, and the fourth point 121d is a counterclockwise order, and an arrangement order of the second point 121b, the third point 121c, and the fourth point 121d is a clockwise order, that is, if the fourth point 121d is located in an $R_1$ area, the controller 130 may determine that a figure defined by the four points 121a, 121b, 121c, and 121d is not a concave quadrangle.

Figure 14C:
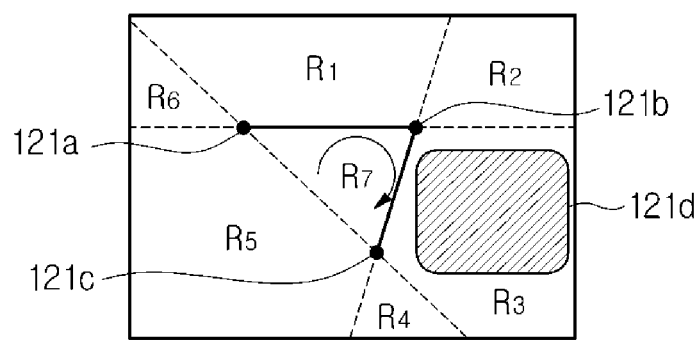

Also, as shown in FIG. 14C, if an arrangement order of the first point 121a, the second point 121b, and the fourth point 121d is a clockwise order, an arrangement order of the first point 121a, the third point 121c, and the fourth point 121d is a counterclockwise order, and an arrangement order of the second point 121b, the third point 121c, and the fourth point 121d is a counterclockwise order, that is, if the fourth point 121d is located in an $R_3$ area, the controller 130 may determine that a figure defined by the four points 121a, 121b, 121c, and 121d is not a concave quadrangle.

Figure 14D:
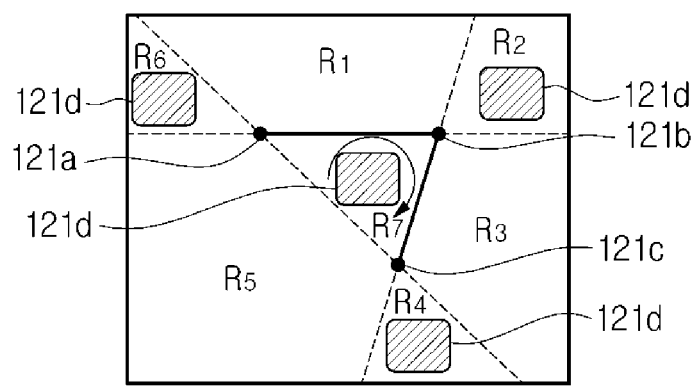

However, in the remaining cases that do not correspond to FIG. 14A, 14B, or 14C, for example, in a case where it is determined that the fourth point 121d is located in an $R_2$ area, an $R_4$ area, an $R_6$ area, or an $R_7$ area as shown in FIG. 14D, the controller 130 may determine that a figure defined by the four points 121a, 121b, 121c, and 121d is a concave quadrangle or does not correspond to any quadrangle.

Figure 15A:
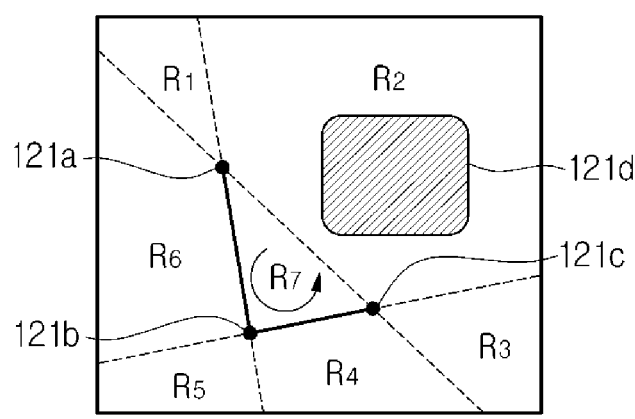

Also, as shown in FIG. 15A, when an arrangement order of the first point 121a, the second point 121b, and the third point 121c is a counterclockwise order, if an arrangement order of the first point 121a, the second point 121b, and the fourth point 121d is a counterclockwise order, an arrangement order of the first point 121a, the third point 121c, and the fourth point 121d is a counterclockwise order, and an arrangement order of the second point 121b, the third point 121c, and the fourth point 121d is a counterclockwise order, that is, if the fourth point 121d is located in an $R_2$ area, the controller 130 may determine that a figure defined by the four points 121a, 121b, 121c, and 121d is not a concave quadrangle.

Figure 15B:
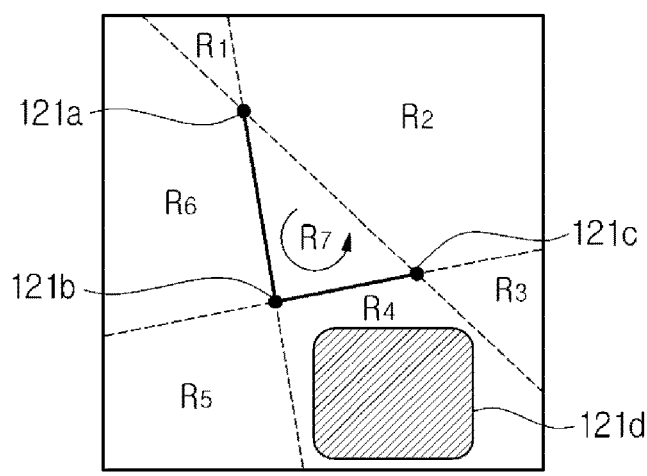

Also, as shown in FIG. 15B, if an arrangement order of the first point 121a, the second point 121b, and the fourth point 121d is a counterclockwise order, an arrangement order of the first point 121a, the third point 121c, and the fourth point 121d is a clockwise order, and an arrangement order of the second point 121b, the third point 121c, and the fourth point 121d is a clockwise order, that is, if the fourth point 121d is located in an $R_4$ area, the controller 130 may determine that a figure defined by the four points 121a, 121b, 121c, and 121d is not a concave quadrangle.

Figure 15C:
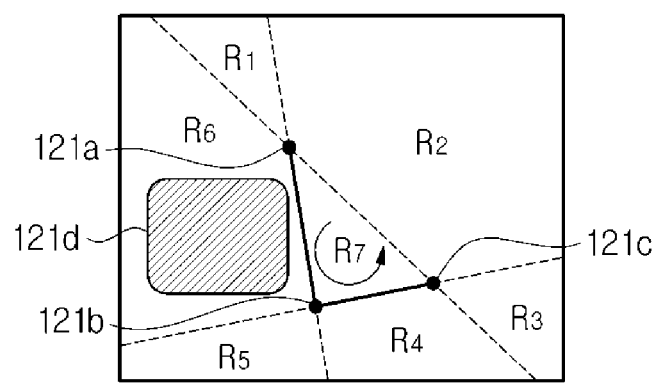

Also, as shown in FIG. 15C, if an arrangement order of the first point 121a, the second point 121b, and the fourth point 121d is a clockwise order, an arrangement order of the first point 121a, the third point 121c, and the fourth point 121d is a counterclockwise order, and an arrangement order of the second point 121b, the third point 121c, and the fourth point 121d is a counterclockwise order, that is, if the fourth point 121d is located in an $R_6$ area, the controller 130 may determine that a figure defined by the four points 121a, 121b, 121c, and 121d is not a concave quadrangle.

Figure 15D:
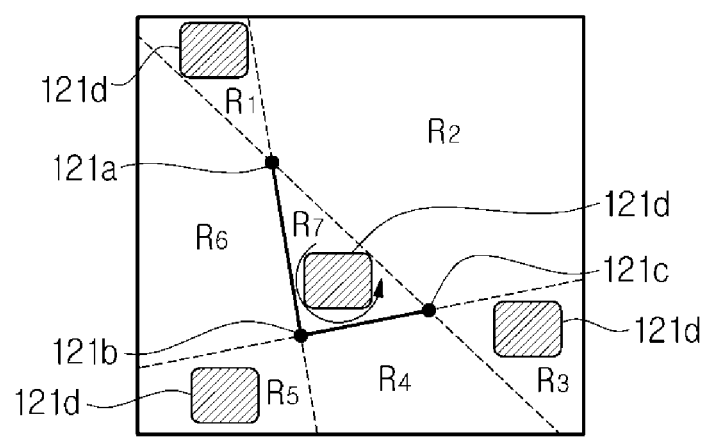

However, in the remaining cases that do not correspond to FIG. 15A, 15B, or 15C, for example, in a case where it is determined that the fourth point 121d is located in an $R_1$ area, an $R_3$ area, an $R_5$ area, or an $R_7$ area as shown in FIG. 15D, the controller 130 may determine that a figure defined by the four points 121a, 121b, 121c, and 121d is a concave quadrangle or does not correspond to any quadrangle.

In other words, in the cases of FIGS. 14A, 14B, and 14C and FIGS. 15A, 15B, and 15C, the controller 130 may determine that the first to fourth points 121a, 121b, 121c, and 121d are valid, and create a window defined by the four points 121a, 121b, 121c, and 121d, in operation 320.

FIGS. 16A, 16B, 16C, and 16D are views for describing operation of creating a window of a quadrangle using four points according to exemplary embodiments.

Figure 16A:
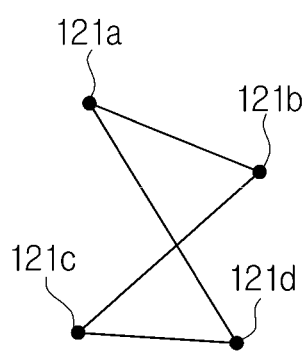
FIGS. 16A, 16B, and 16C are views for describing operation of creating a window in a shape of a quadrangle using four points according to an exemplary embodiment.
Figure 16B:
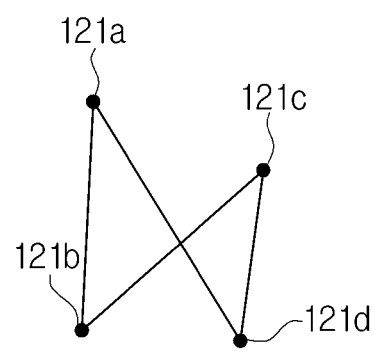

If four points 121a, 121b, 121c, and 121d input by a user are connected by straight lines in the input order of the points to create a window, the straight lines connecting the points to each other may cross each other to create two polygons or more, as shown in FIGS. 16A and 16B.

Figure 16C:
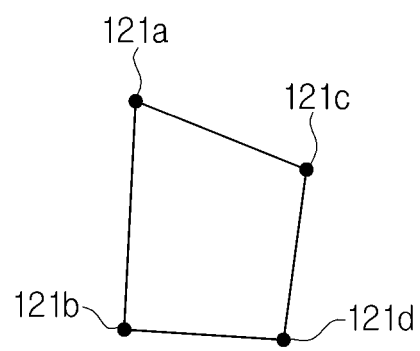

In an exemplary embodiment, the order in which points are input by a user may not be considered in creating a window. Accordingly, the window creator 131 may connect the four points 121a, 121b, 121c, and 121d to each other regardless of the order in which the points are input by a user such that a quadrangular window can be formed as shown in FIG. 16C.

To create a quadrangular window, the window creator 131 may connect each point to other two points by straight lines while the straight lines do not cross each other. Also, the window creator 131 may connect a point to other two points such that the connected four points 121a, 121b, 121c, and 121d are prevented from forming an incomplete figure with an opening, etc., or creating two or more polygons.

To prevent an incomplete figure with an opening, etc., or two or more polygons from being created, the window creator 131 may rearrange the order in which the points are connected, according to the arrangement order of the points, in operation of determining the validity of the points. Referring again to FIGS. 14A, 14B, and 14C and FIGS. 15A, 15B, and 15C, if the points 121a, 121b, 121c, and 121d are connected in the order in which the points 121a, 121b, 121c, and 121d have been input although all the four points 121a, 121b, 121c, and 121d are valid, an invalid figure such as two triangles may be created.

Accordingly, the window creator 131 may connect the points in the order in which the points are connected to create a normal quadrangle, regardless of the order in which the points have been input. Hereinafter, an example of connecting points in a clockwise order to create a window will be described.

In the case of FIG. 14A, the four points 121a, 121b, 121c, and 121d may be connected in the order in which the points 121a, 121b, 121c, and 121d have been input to create a window of a quadrangle. However, in the case of FIG. 14B, if the four points 121a, 121b, 121c, and 121d are connected in the order in which the points 121a, 121b, 121c, and 121d have been input, two triangles may be formed. Accordingly, the first point 121a and the fourth point 121d may be in the reverse order when connecting the four points 121a, 121b, 121c, and 121d. That is, the fourth point 121d, the second point 121b, the third point 121c, and the first point 121a may be connected in this order to create a window of a quadrangle.

Similarly, in the case of FIG. 14C, if the four points 121a, 121b, 121c, and 121d are connected in the order in which the points 121a, 121b, 121c, and 121d have been input, two triangles may be formed. In this case, the third point 121c and the fourth point 121d may be in the reverse order when connecting the four points 121a, 121b, 121c, and 121d to thereby create a window of a quadrangle.

In the case of FIG. 15A, the second point 121b and the fourth point 121d may be in the reverse order when connecting the four points 121a, 121b, 121c, and 121d, that is, in a clockwise order to thereby create a window of a quadrangle. In the case of FIG. 15B, the second point 121b and the third point 121c may be in the reverse order when connecting the four points 121a, 121b, 121c, and 121d, and again the third point 121c and the fourth point 121d may be in the reverse order when connecting the four points 121a, 121b, 121c, and 121d to thereby create a window of a quadrangle. In the case of FIG. 15C, the second point 121b and the third point 121c may be in the reverse order when connecting the four points 121a, 121b, 121c, and 121d to thereby create a window of a quadrangle.

When the window creator 131 determines the validity of a point and feeds the result of the determination back to a user whenever the point is input, as described above, the user can quickly correct any invalid point, and a time period for which shutter processing is performed can be reduced.

After creating the window, the window creator 131 may detect coordinates corresponding to coordinates of the window from the medical image displayed on the display 120, and set an area corresponding to the detected coordinates to a window area. If a domain in which the coordinates of the window are defined is different from a domain that is applied to the medical image, the window creator 131 may perform domain conversion using a correlation between the two domains.

Also, the image processor 132 may perform shutter processing to reduce the brightness of the remaining area except for the window area in the medical image displayed on the display 120 to render the remaining area appear dark, or to reduce the definition of the remaining area to render the remaining area appear blurry.

Since the remaining area except for the window area is not cut off although the image processor 132 performs shutter processing, image information about the remaining area can be maintained without being deleted.

Figure 17:
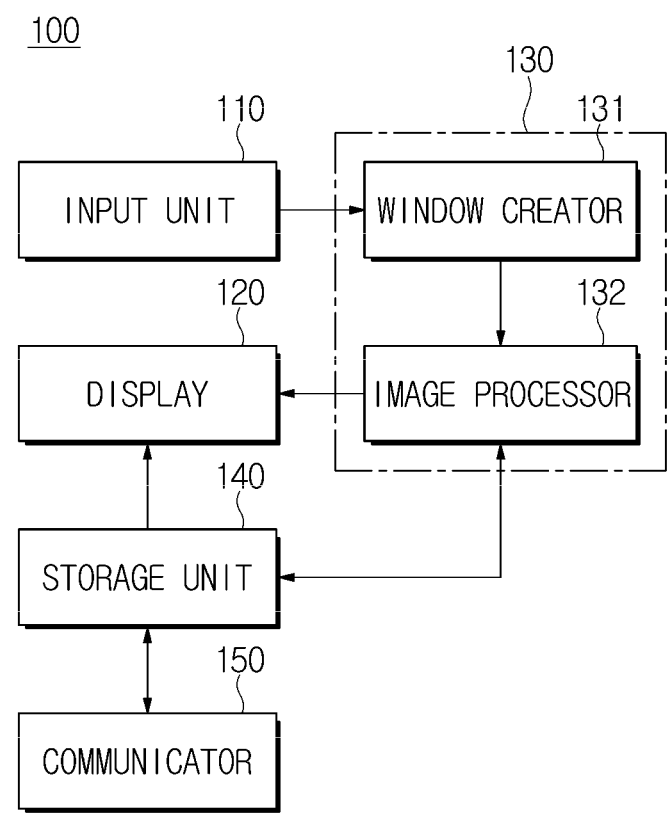
FIG. 17 is a control block diagram of an image processing apparatus further including a communicator, according to an exemplary embodiment.

FIG. 17 is a control block diagram of the image processing apparatus 100 further including a communicator, according to an exemplary embodiment.

Referring to FIG. 17, the image processing apparatus 100 may further include a communicator 150 to perform wired and/or wireless communication with another apparatus or system.

A medical image subject to shutter processing by the image processor 132 may be stored in the storage unit 150, and the medical image stored in the storage unit 150 may be transmitted to another apparatus or system through the communicator 150.

For example, if the image processing apparatus 100 is included in the medical imaging apparatus 20, a window area may be selected by a radiological technologist, shutter processing may be performed according to the window area, and then, the resultant medical image may be stored in the storage unit 150. The medical image stored in the storage unit 150 may be transmitted to a central server 10 in a medical institution through the communicator 150. At this time, the original image not subject to shutter processing may also be transmitted to the central server 10, together with the shutter-processed medical image, or only the shutter-processed medical image may be transmitted to the central server 10.

The central server 10 may store the received image(s). A doctor may search for the shutter-processed image from among images stored in the central server 10 to receive the searched image through the user control apparatus 30 using the communicator 150. Accordingly, the doctor can accurately recognize an area to be diagnosed, based on the shutter-processed image, and perform more accurate and quicker diagnosis.

According to another example, if the image processing apparatus 100 is included in the central server 10, the image processing apparatus 100 may receive a medical image from the medical imaging apparatus 20 through the communicator 150, and store the received medical image in the storage unit 140. Accordingly, a doctor or a radiological technologist can search for a desired medical image in the central server 10, and input a selection for setting a window area to the central server 10. Then, a shutter-processed image may be transmitted to the user control apparatus 30 through the communicator 150.

According to still another example, if the image processing apparatus 100 is included in the user control apparatus 30, the image processing apparatus 100 may receive a medical image from the central server 10 or the medical imaging apparatus 20 through the communicator 150, and receive a selection for setting a window area of the received image to perform shutter processing.

In the exemplary embodiments described above, a case of creating a window of a quadrangle by receiving four points (n=4) has been described. Hereinafter, another exemplary embodiment of receiving user inputs will be described.

Figure 18:
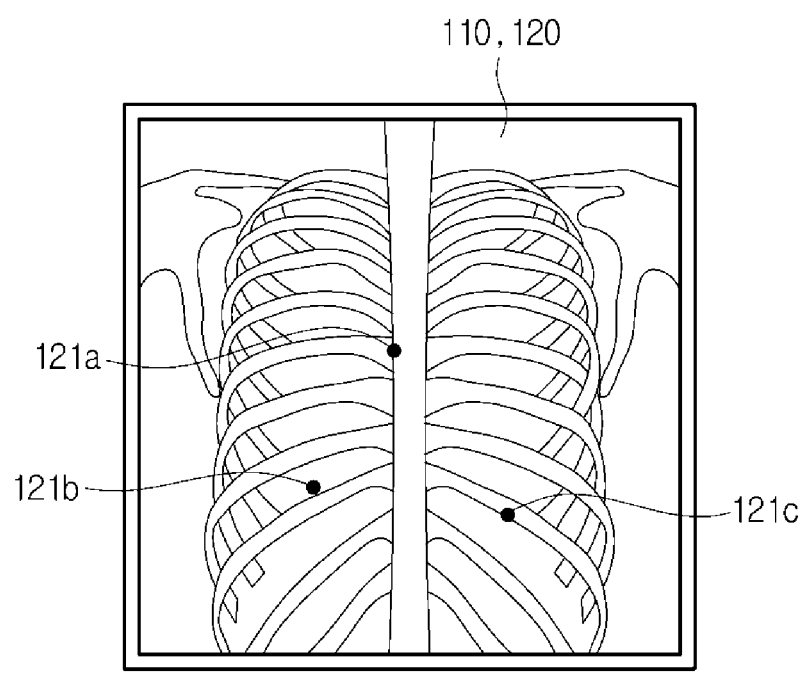
FIG. 18 is a view for describing an example of receiving inputs of three points for performing shutter processing on a medical image in an image processing apparatus according to an exemplary embodiment.
Figure 19:
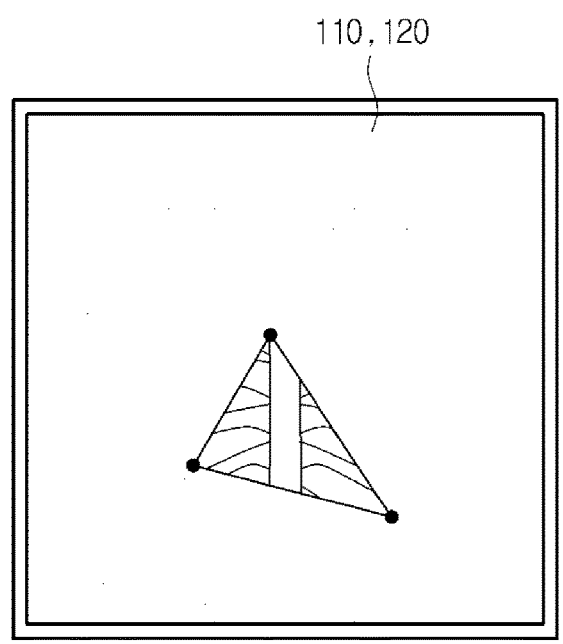
FIG. 19 shows a result of shutter processing performed by an image processing apparatus that receives three points according to an exemplary embodiment.

FIG. 18 is a view for describing an example of receiving inputs of three points for performing shutter processing on a medical image in the image processing apparatus 100 according to an exemplary embodiment, and FIG. 19 shows the result of shutter processing performed by the image processing apparatus 100 that receives the three points.

The image processing apparatus 100 may receive n points (wherein n is an integer greater than or equal to 3) from a user, and set a window in a shape of a polygon whose vertexes are the n points, as described above. Accordingly, if n is 3, the image processing apparatus 100 may set a window in a shape of a triangle.

As shown in FIG. 18, a user may input three points 121a, 121b, and 121c on an image displayed on the display 120 through the input unit 110. A method in which a user inputs points has been described above with reference to the case of n being 4.

The window creator 131 may determine validity of the three points 121a, 121b, and 121c. This operation may be the same as operation of determining validity of the first to third points, as described above with reference to FIG. 13.

If the window creator 131 determines that all of the three points 121a, 121b, and 121c are valid, the controller 130 may set a triangle whose vertexes are the three points 121a, 121b, and 121c, to a window, and the image processor 132 may perform shutter processing on the remaining area except for the window area of the medical image displayed on the display 120 to render the remaining area appear dark or blurry, as shown in FIG. 19.

Figure 20:
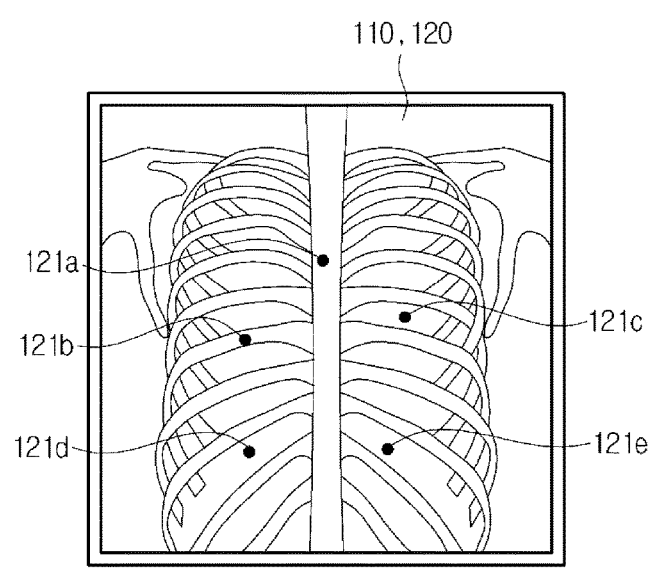
FIG. 20 is a view for describing an example of receiving inputs of five points for performing shutter processing on a medical image according to an exemplary embodiment.
Figure 21:
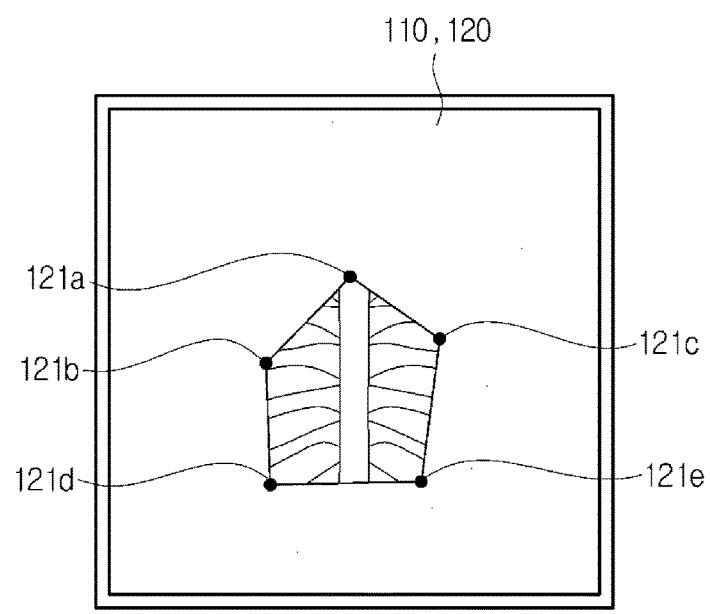
FIG. 21 shows a result of shutter processing performed by an image processing apparatus that receives five points according to an exemplary embodiment.

FIG. 20 is a view for describing an example in which the image processing apparatus 100 according to an exemplary embodiment receives a user's inputs of inputting five points when performing shutter processing on a medical image, and FIG. 21 shows the result of shutter processing performed by the image processing apparatus 100 that received the five points.

When receiving n points, wherein n is 5, a window in a shape of a pentagon may be set. As shown in FIG. 20, a user may input five points 121a, 121b, 121c, 121d, and 121e on an image displayed on the display 120 through the input unit 110. A method in which a user inputs points has been described above with reference to the case of n being 4.

The window creator 131 may determine validity of the five points 121a, 121b, 121c, 121d, and 121e. This operation may be performed by determining validity of the fifth point 121e after operation of determining validity of the first to fourth points 121a, 121b, 121c, and 121d as described above with reference to FIG. 13. If the fifth point 121e is not spaced the reference distance or more apart from at least one of the first point 121a, the second point 121b, the third point 121c, and the fourth point 121d, if the fifth point 121e is on a straight line with at least two of the first point 121a, the second point 121b, the third point 121c, and the fourth point 121d, or if a concave figure is formed by the fifth point 121e, that is, if at least one of the internal angles of a figure defined by connecting the five points 121a, 121b, 121c, 121d, and 121e to each other is 180 degrees or more, the window creator 131 may determine that the fifth point 121e is invalid, and again receive an input from a user.

If the window creator 131 determines that all of the five points 121a, 121b, 121c, 121d, and 121e are valid, the window creator 131 may set a pentagon whose vertexes are the five points 121a, 121b, 121c, 121d, and 121e to a window, and the image processor 132 may perform shutter processing on the remaining area except for the window area in the medical image displayed on the display 120 to render the remaining area dark or blurry, as shown in FIG. 21.

Figure 22:
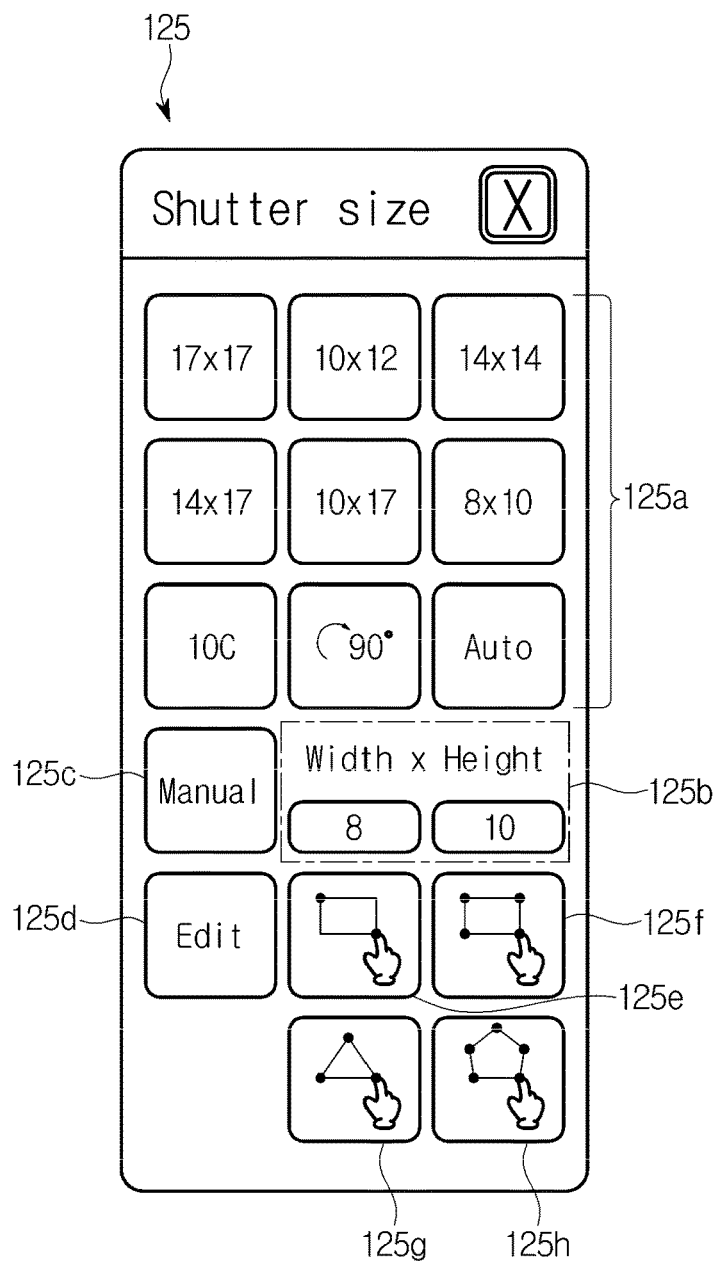
FIG. 22 shows an example of a graphic user interface that can be used to set a window having a triangle or pentagon shape according to an exemplary embodiment.

FIG. 22 shows an example of a graphic user interface that can be used to set a window having a triangle or pentagon shape.

The image processing apparatus 100 may set a window of a triangle or a pentagon, as well as a window of a quadrangle. Therefore, the image processing apparatus 100 can receive a user's input of selecting a shape of a window to be set. Referring to FIG. 22, a window setting menu 125 may include an icon 125g to set a window of a triangle by selecting three points, and an icon 125h to set a window of a pentagon by selecting five points.

If a user selects the icon 125g, the input unit 110 may enter a standby state to receive three points, and if the user selects the icon 125h, the input unit 110 may enter a standby state to receive five points. If the user selects an icon 125f, the input unit 110 may enter a standby state to receive four points.

Figure 23:
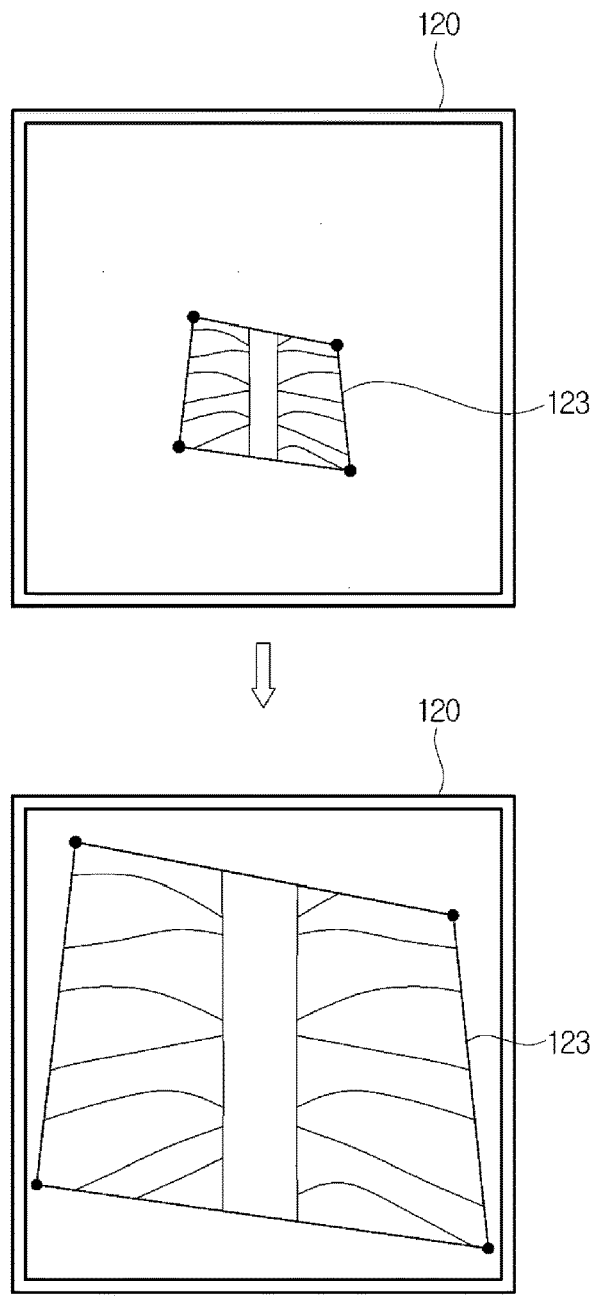
FIG. 23 shows a set window and an enlarged image of the set window according to an exemplary embodiment.
Figure 24:
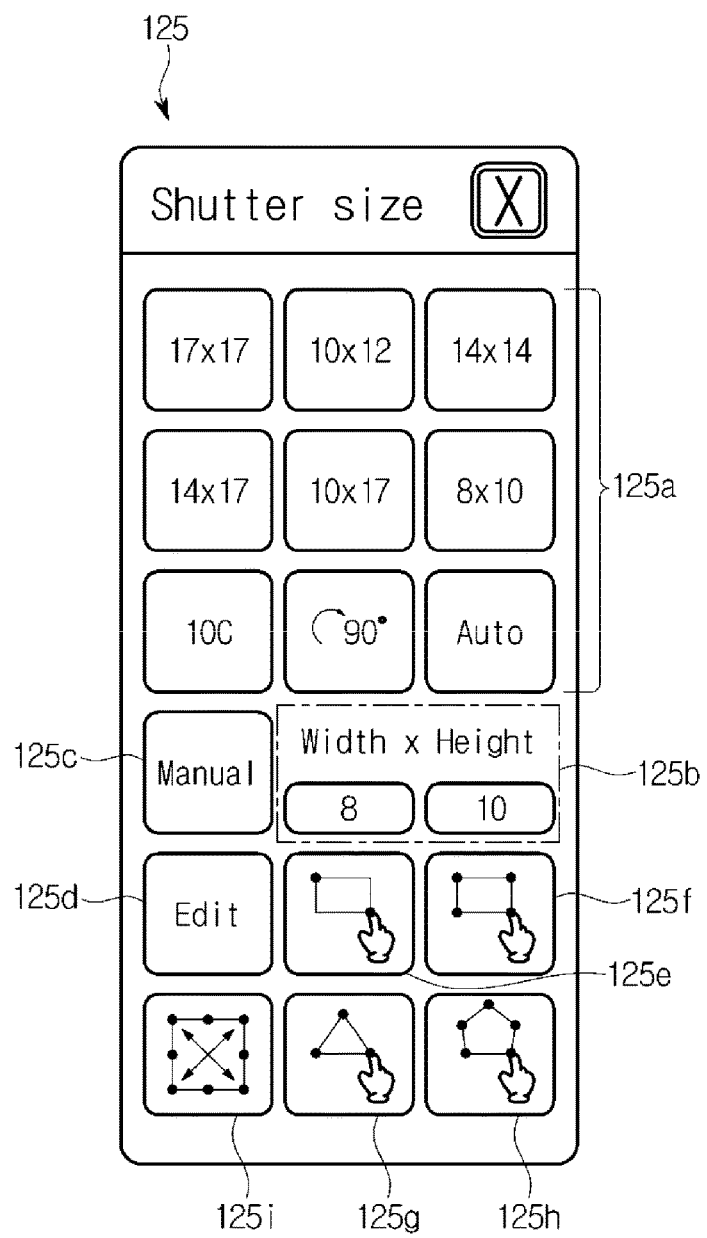
FIG. 24 shows an example of a graphic user interface that can be used to enlarge a window area according to an exemplary embodiment.

FIG. 23 shows a set window and an enlarged image according to an exemplary embodiment, and FIG. 24 shows an example of a graphic user interface that can be used to enlarge a window area according to an exemplary embodiment.

A window area 123 may be defined by points input by a user, as described above, and the size of the window area 123 may also be defined by the points input by the user. However, when a user wants to view the window area 123 in detail in a medical image 230 displayed on the display 120, the user can enlarge the window area 123, as shown in FIG. 23.

Herein, enlarging the window area 123 does not mean enlarging an area of the window area 123 in the medical image 230, but means showing an enlarged view of the window area 123.

As shown in FIG. 24, the window setting menu 125 may further include an icon 125i to enlarge a window. Accordingly, a user may select the icon 125i for enlarging a window after a window is set, to view the window area in detail.

In the exemplary embodiments of the image processing apparatus 100, as described above, the case of setting a window of a polygon has been described, however, the exemplary embodiments are not limited thereto. For example, the image processing apparatus 100 can set a window of a circle. Hereinafter, an exemplary embodiment of setting a window of a circle will be described in detail.

FIGS. 25, 26, 27, and 28 are views for describing an example in which an image processing apparatus according to an exemplary embodiment receives a user's selection of setting a circular window when performing shutter processing on a medical image.

Figure 25:
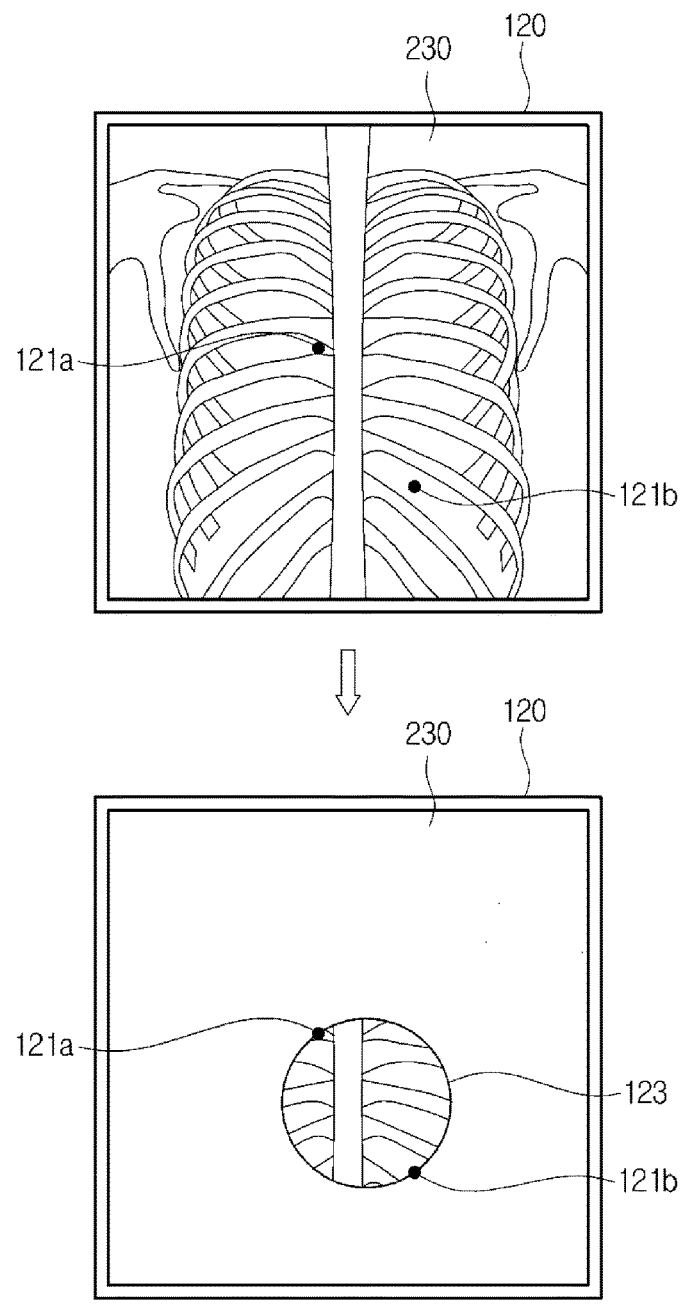
FIGS. 25, 26, 27, and 28 are views for describing an example of receiving a user's input of setting a circular window for performing shutter processing on a medical image in an image processing apparatus according to an exemplary embodiment.

For example, referring to FIG. 25, if a user may input two points 121a and 121b on a medical image displayed on the display 120, the controller 130 may set a window in a shape of a circle whose circumference is defined by the two points 121a and 121b, that is, a window in a shape of a circle whose diameter corresponds to a straight line connecting the two points 121a and 121b.

In another example, the controller 130 may set a window of a circle whose circumference includes at least one of the two points 121a and 121b, and whose center point is the other one of the two points. That is, the controller 130 may set a window of a circle whose radius corresponds to a straight line connecting the two points.

Also, the controller 130 may determine validity of the input points. More specifically, the window creator 131 may determine that the second point is invalid if a distance between the two points is shorter than the reference distance, and again receive another input from a user.

Figure 26:
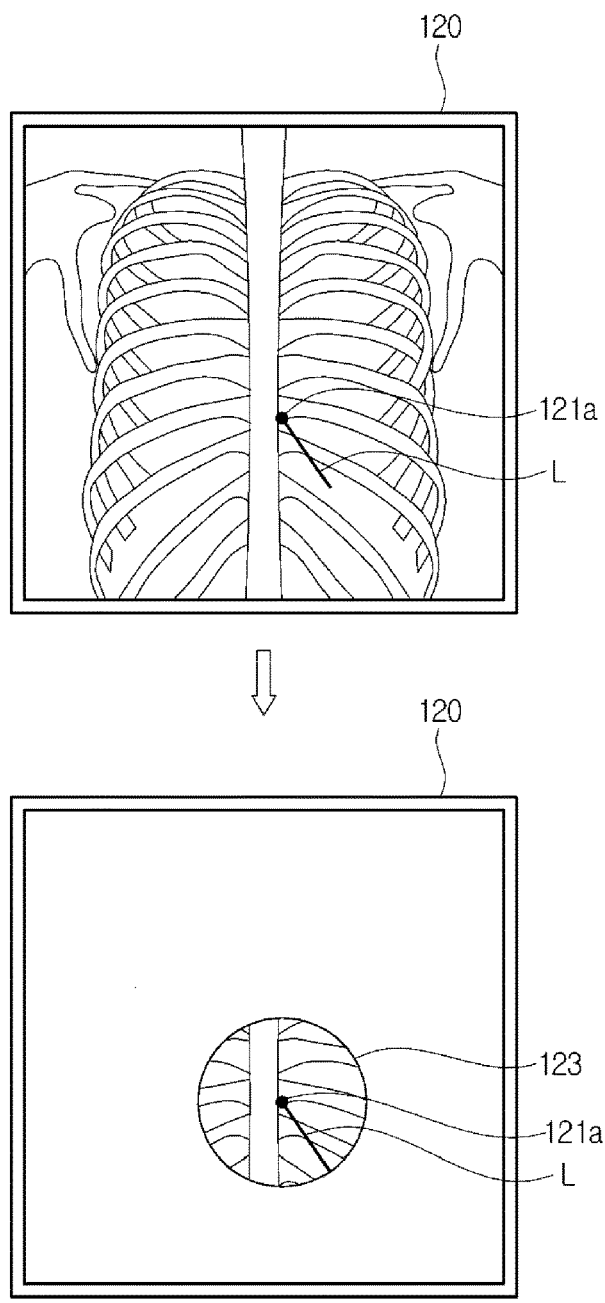

According to another example, as shown in FIG. 26, a user may input a point 121a and a straight line L starting from the point 121a on a medical image 230 displayed on the display 120. In this case, the controller 130 may set a window of a circle whose center point is the point 121a and whose radius corresponds to the straight line L.

Figure 27:
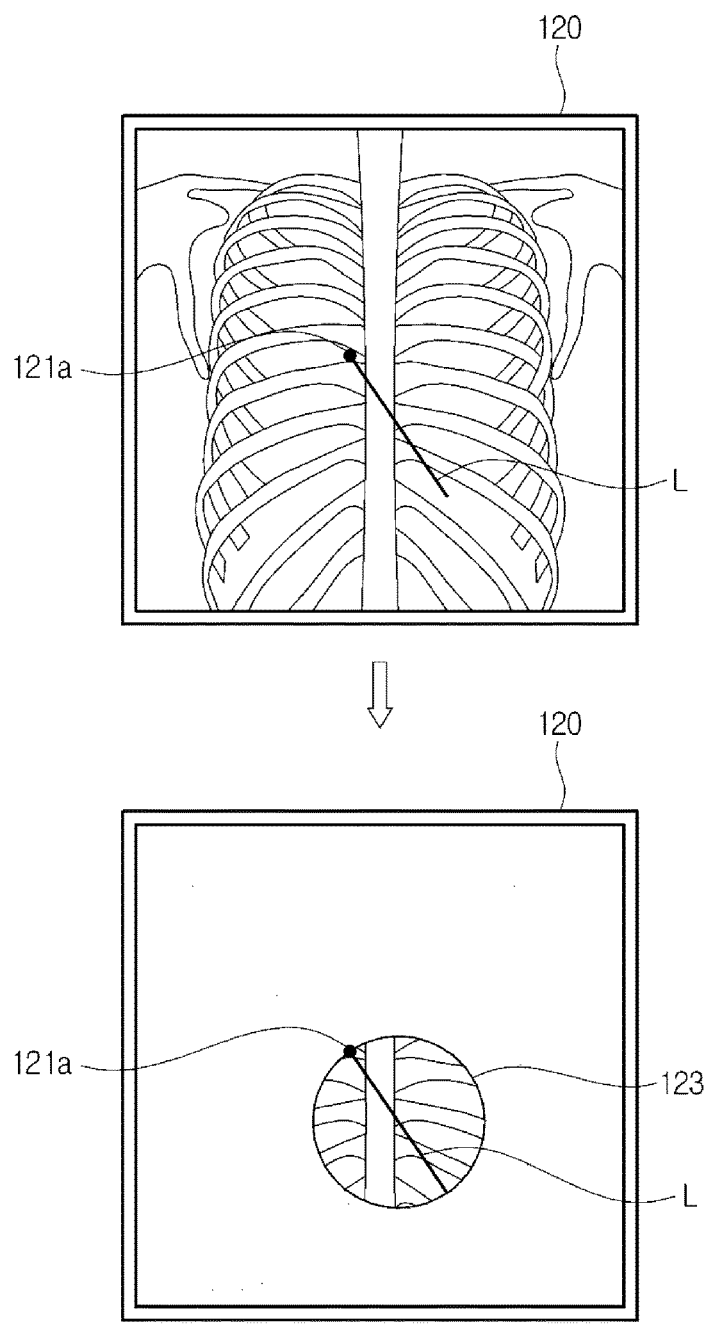

Alternatively, as shown in FIG. 27, the controller 130 may set a window of a circle whose circumference includes the input point 121a, and whose diameter corresponds to the straight line L.

Similarly, the controller 130 may determine validity of the input point. More specifically, the window creator 131 may determine that the input point is invalid if a length of the straight line is shorter than a reference length, and again receive another input from the user.

Figure 28:
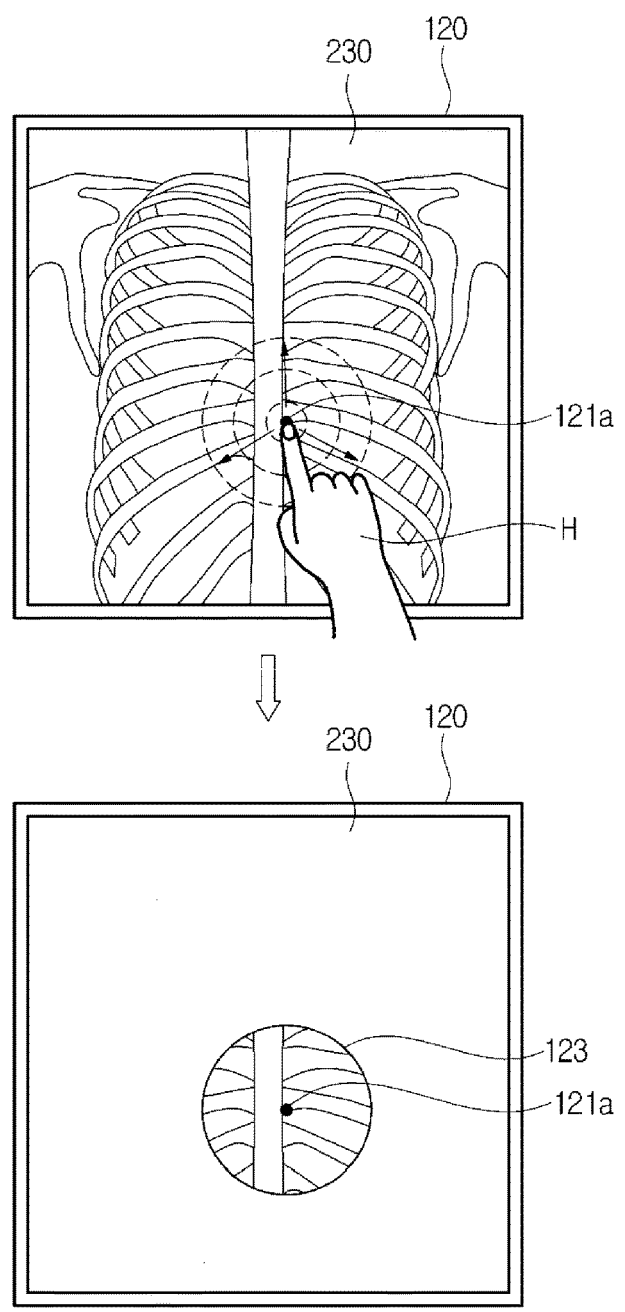

According to still another example, as shown in FIG. 28, a user may input a point 121a on a medical image 230 displayed on the display 120. If the input unit 110 is a touch panel, the user may touch the corresponding point with the user's hand H. If the user's touch is input, a circle whose center is the input point 121a may be created, and in response to a time duration of the user's touch, the size of the circle may gradually increase.

When the user stops touching the point 121a, that is, when the user takes the user's hand H off the input unit 110, the size of the circle may no longer increase, and a circle having a size at which the size of the circle no longer increase may define the shape of a window.

Figure 29:
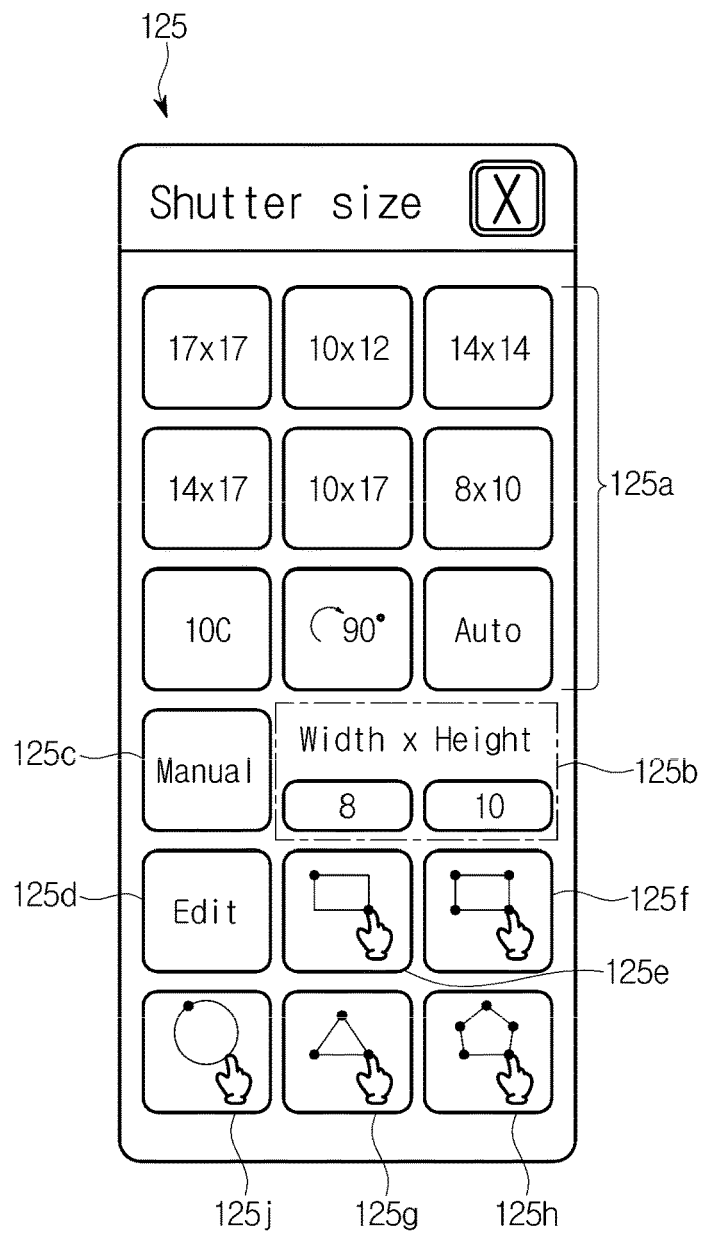
FIG. 29 shows an example of a graphic user interface that can be used to set a circular window according to an exemplary embodiment.

FIG. 29 shows an example of a graphic user interface that can be used to set a circular window.

As shown in FIG. 29, a window setting menu 125 may include an icon 125j to set a circular window. If the icon 125j is selected by a user, the input unit 110 may enter a standby state to receive a selection for setting a circular window, and the window creator 131 may determine validity of inputs, independently from the case of setting a window of a polygon as shown in FIGS. 25 and 26.

The image processing apparatus 100 can be included in the medical imaging apparatus 20, as described above, and hereinafter, the medical imaging apparatus 20 including the image processing apparatus 100 will be described.

Figure 30:
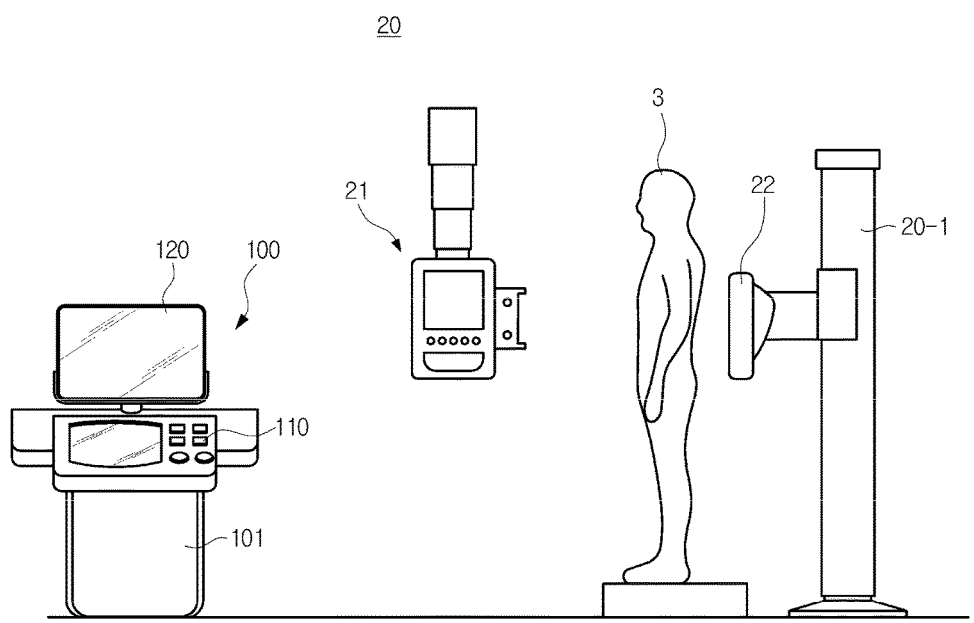
FIG. 30 shows an external appearance of a medical imaging apparatus which is an X-ray imaging apparatus that performs radiography, according to an exemplary embodiment.
Figure 31:
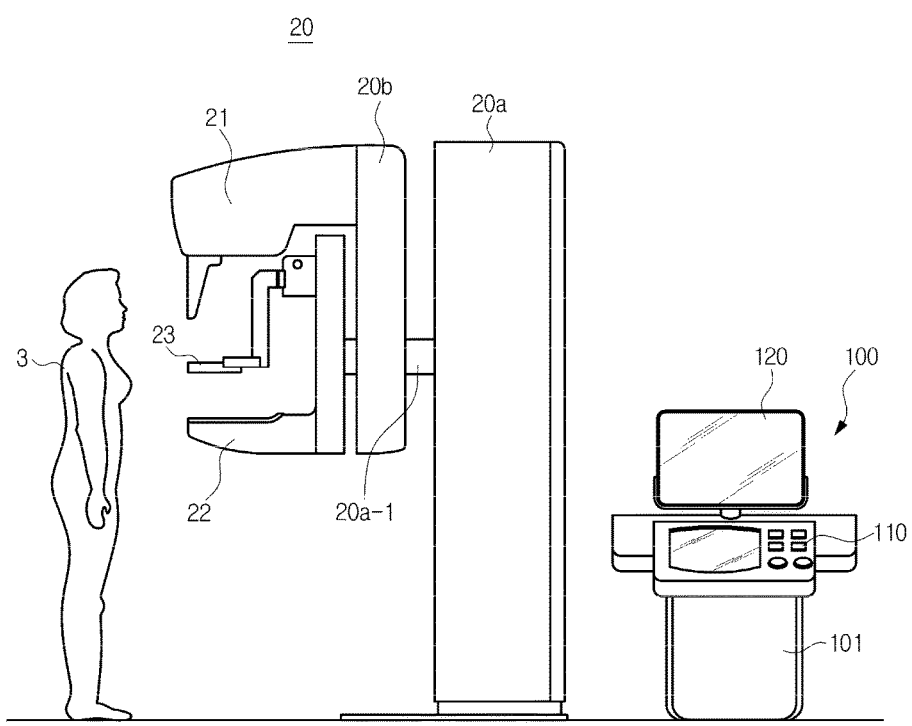
FIG. 31 shows an external appearance of a medical imaging apparatus which is an X-ray imaging apparatus that performs mammography, according to another exemplary embodiment.
Figure 32:
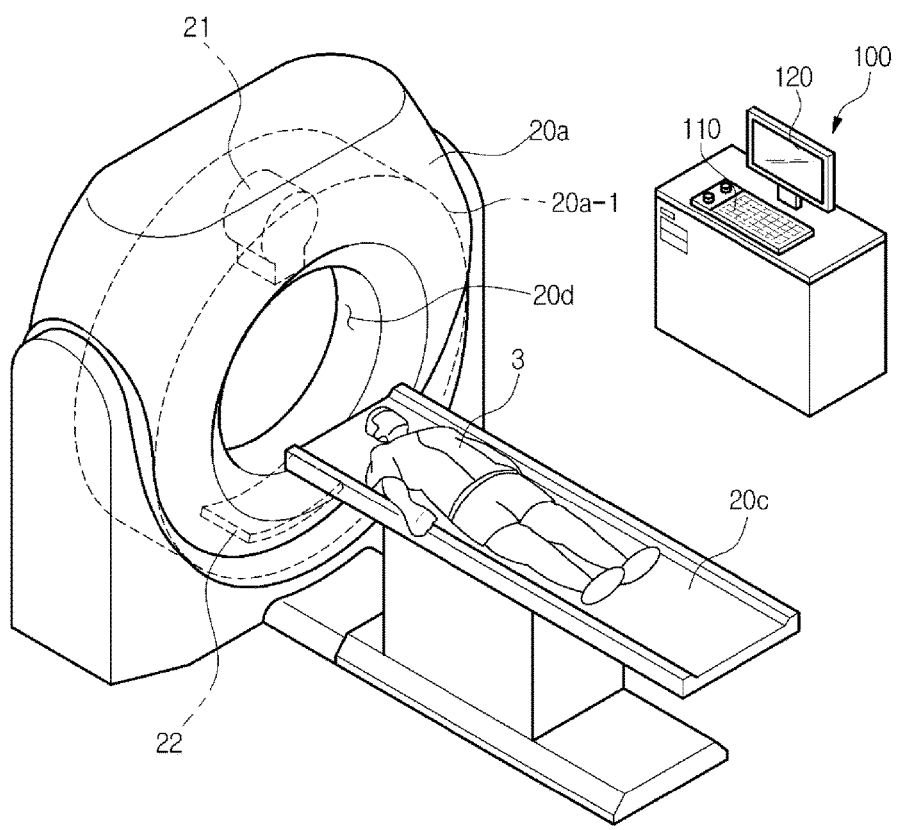
FIG. 32 shows an external appearance of a medical imaging apparatus which is a computerized tomography (CT) apparatus according to still another exemplary embodiment.

FIG. 30 shows an external appearance of an X-ray imaging apparatus that performs radiography, according to an example of the medical imaging apparatus 20, FIG. 31 shows an external appearance of an X-ray imaging apparatus that performs mammography, according to another example of the medical imaging apparatus 20, and FIG. 32 shows an external appearance of a computerized tomography (CT) apparatus according to still another example of the medical imaging apparatus 20.

If the medical imaging apparatus 20 is an X-ray imaging apparatus to perform radiography, the X-ray imaging apparatus 20 may include an X-ray source 21 to irradiate X-rays to an object, and an X-ray detector 22 to detect X-rays, as shown in FIG. 30.

The X-ray source 21 may be mounted on the ceiling of a room for X-ray scanning. If the X-ray source 21 irradiates X-rays toward a target area of an object 3, the X-ray detector 22 mounted on a stand 20-1 may detect X-rays transmitted through the object 3.

Referring to FIG. 31, if the medical imaging apparatus 20 is an X-ray imaging apparatus for mammography, an arm 20b may be connected to a housing 20a, an X-ray source 21 may be installed in the upper part of the arm 20b, and an X-ray detector 22 may be installed in the lower part of the arm 20b. When tomosynthesis is performed, the arm 20b may rotate with respect to a shaft 20b-1.

The X-ray source 21 may be disposed to face the X-ray detector 22. By locating a breast of the object 3 between the X-ray source 21 and the X-ray detector 22, and irradiating X-rays to the breast, X-rays transmitted through the breast of the object 3 may be detected. Since breasts are soft tissues, the X-ray imaging apparatus 20 for mammography may further include a pressure paddle 23.

The pressure paddle 23 may press the breast to a predetermined thickness during X-ray scanning. If the breast is pressed, the thickness of the breast may be thinned to acquire clearer images while reducing a dose of X-rays. Also, overlapping tissues may be spread so that a viewer can observe the internal structure of the breast in more detail.

A CT apparatus, which acquires images by transmitting X-rays to an object, similar to the X-ray imaging apparatus 20 of FIGS. 30 and 31, can irradiate X-rays at various angles toward an object to thereby acquire section images of the object.

If the medical imaging apparatus 20 is a CT apparatus, a housing 20a may include a gantry 20a-1, and an X-ray source 21 and an X-ray detector 22 may be disposed to face each other in the inside of the gantry 20a-1, as shown in FIG. 32.

If an object 3 is conveyed by a patient table 20c and placed inside a bore 20d that is the center of the gantry 20a-1, the X-ray source 21 and the X-ray detector 22 may rotate 360 degrees with respect to the bore 20d to acquire projected data of the object 3.

Figure 33:
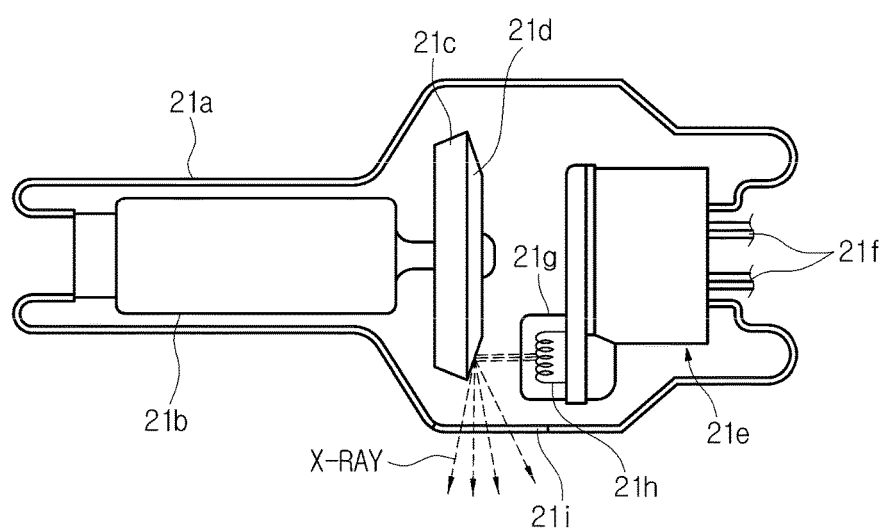
FIG. 33 shows a configuration of an X-ray source included in an X-ray imaging apparatus according to an exemplary embodiment.
Figure 34:
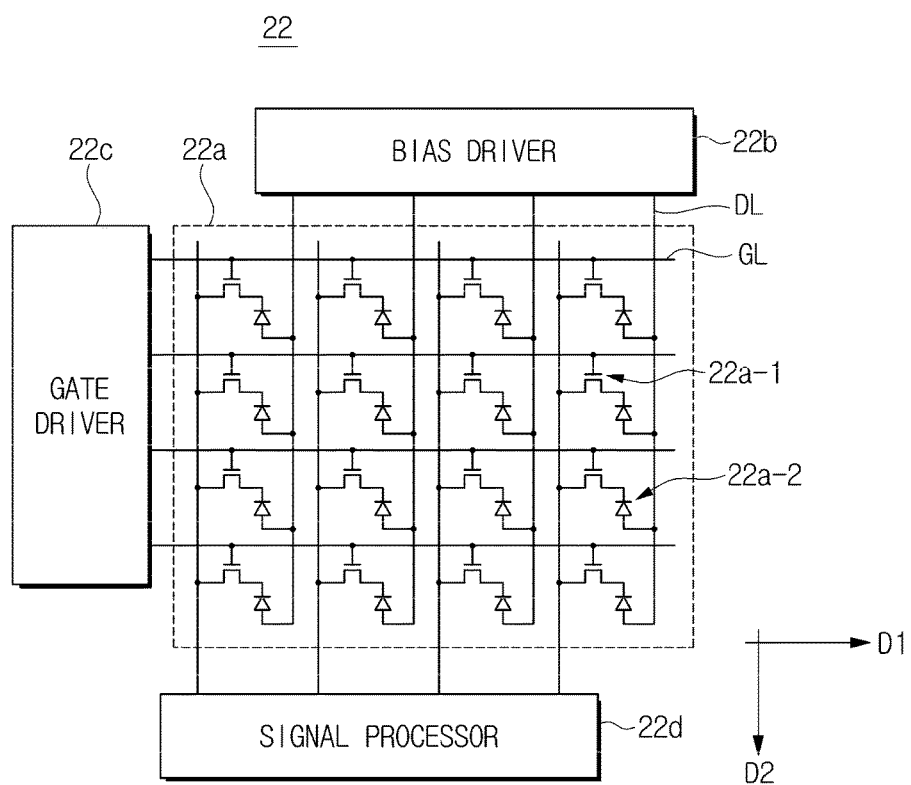
FIG. 34 shows a configuration of an X-ray detector included in an X-ray imaging apparatus according to an exemplary embodiment.

FIG. 33 shows a configuration of the X-ray source 21 included in the X-ray imaging apparatus 20 according to an exemplary embodiment, and FIG. 34 shows a configuration of the X-ray detector 22 included in the X-ray imaging apparatus 20 according to an exemplary embodiment.

The X-ray source 21 is also called an X-ray tube, and may receive a supply voltage from an external power supply (not shown) to generate X-rays.

Referring to FIG. 33, the X-ray detector 22 may be embodied as a two-electrode vacuum tube including an anode 21c and a cathode 21e. The cathode 21e may include a filament 21h and a focusing electrode 21g for focusing electrons, and the focusing electrode 21g is also called a focusing cup.

The inside of a glass tube 21a may be evacuated to a high vacuum state of about 10 mmHg, and the filament 21h of the cathode 21e may be heated to a high temperature, thereby generating thermoelectrons. The filament 21h may be a tungsten filament, and the filament 21h may be heated by applying current to electrical leads 21f connected to the filament 21h.

The anode 21c may include copper, and a target material 21d may be applied on the surface of the anode 21c facing the cathode 21e, wherein the target material 21d may be a high-resistance material, e.g., Cr, Fe, Co, Ni, W, or Mo. The target material 21d may be formed to have a slope inclined at a predetermined angle, and the greater the predetermined angle, the smaller the focal spot size. In addition, the focal spot size may vary according to a tube voltage, tube current, the size of the filament 21h, the size of the focusing electrode 21e, a distance between the anode 21c and the cathode 21e, etc.

When a high voltage is applied between the cathode 21e and the anode 21c, thermoelectrons may be accelerated and collide with the target material 21d of the anode 21e, thereby generating X-rays. The X-rays may be irradiated to the outside through a window 21i. The window 21i may be a Beryllium (Be) thin film. Also, a filter (not shown) for filtering a specific energy band of X-rays may be provided on the front or rear side of the window 21i.

The target material 21d may be rotated by a rotor 21b. When the target material 21d rotates, the heat accumulation rate may increase ten times per unit region and the focal spot size may be reduced, compared to when the target material 21d is fixed.

The voltage that is applied between the cathode 21e and the anode 21c of the X-ray tube 21 is called a tube voltage. The magnitude of a tube voltage may be expressed as a crest value (kVp). When the tube voltage increases, velocity of thermoelectrons increases accordingly. Then, energy (energy of photons) of X-rays that are generated when the thermoelectrons collide with the target material 21d also increases.

Current flowing through the X-ray tube 21 is called tube current, and can be expressed as an average value (mA). When tube current increases, the number of thermoelectrons emitted from the filament 21h increases, and as a result, a dose of X-rays (that is, the number of X-ray photons) that are generated when the thermoelectrons collide with the target material 21d increases.

In summary, energy of X-rays can be controlled by adjusting a tube voltage. Also, a dose or intensities of X-rays can be controlled by adjusting tube current and an X-ray exposure time. Accordingly, it is possible to control the energy, intensity, or dose of X-rays according to the properties of the object such as the kind or thickness of the object or according to the purposes of diagnosis.

The X-ray source 21 may irradiate monochromatic X-rays or polychromatic X-rays. If the X-ray source 21 irradiates polychromatic X-rays having a specific energy band, the energy band of the irradiated X-rays may be defined by upper and lower limits.

The upper limit of the energy band, that is, the maximum energy of the irradiated X-rays may be adjusted according to the magnitude of the tube voltage, and the lower limit of the energy band, that is, the minimum energy of the irradiated X-rays may be adjusted by a filter disposed in the irradiation direction of X-rays.

The filter functions to pass or filter only a specific energy band of X-rays therethrough. Accordingly, by providing a filter for filtering out a specific wavelength band of X-rays on the front or rear side of the window 21i, it is possible to filter out the specific wavelength band of X-rays.

For example, by providing a filter including aluminum or copper to filter out a low energy band of X-rays that deteriorates image quality, it is possible to improve X-ray beam quality, thereby raising the upper limit of the energy band and increasing average energy of X-rays to be irradiated. Also, it is possible to reduce a dose of X-rays that is applied to the object 3.

The X-ray detector 22 may convert X-rays transmitted through the object 3 into electrical signals. As methods for converting X-rays into electrical signals, a direct conversion method and an indirect conversion method may be used.

In the direct conversion method, if X-rays are incident, electron-hole pairs may be temporarily generated in a light receiving device, electrons may move to the anode 21c and holes may move to the cathode 21e by an electric field applied to both terminals of the light receiving device. The X-ray detector 22 may convert the movements of the electrons and holes into electrical signals. In the direct conversion method, the light receiving device may be a photoconductor including amorphous selenium (a-Se), CdZnTe, $HgI_2$, or $PbI_2$.

In the indirect conversion method, a scintillator may be provided between the light receiving device and the X-ray source 21. If X-rays irradiated from the X-ray source 21 react with the scintillator to emit photons having a wavelength of a visible-ray region, the light receiving device may detect the photons, and convert the photons into electrical signals. In the indirect conversion method, the light receiving device may include a-Si, and the scintillator may be a GADOX scintillator of a thin film type, or a CSI (TI) of a micro pillar type or a needle type.

The X-ray detector 22 can use any one of the direct conversion method and the indirect conversion method, and in the following exemplary embodiment, for convenience of description, under an assumption that the X-ray detector 22 uses the indirect conversion method to convert X-rays into electrical signals, a configuration of the X-ray detector 22 will be described in detail.

Referring to FIG. 34, the X-ray detector 22 may include a scintillator (not shown), a light detecting substrate 22a, a bias driver 22b, a gate driver 22c, and a signal processor 22d.

The scintillator may convert X-rays irradiated from the X-ray source 21 into visible rays.

The light detecting substrate 22a may receive the visible rays from the scintillator, and convert the received visible rays into a light detected voltage. The light detecting substrate 22a may include a plurality of gate lines GL, a plurality of data lines DL, a plurality of thin-film transistors 22a-1, a plurality of light detecting diodes 22a-2, and a plurality of bias lines BL.

The gate lines GL may be arranged in a first direction D1, and the data lines DL may be arranged in a second direction D2 that intersects the first direction D1. The first direction D1 may be at right angles to the second direction D2. In the example of FIG. 34, fourth gate lines GL and four data lines DL are shown.

The thin-film transistors 22a-1 may be arranged in the form of a matrix that extends in the first and second directions D1 and D2. Each of the thin-film transistors 22a-1 may be electrically connected to one of the gate lines GL and one of the data lines DL. The gate electrodes of the thin-film transistors 22a-1 may be electrically connected to the gate lines GL, and the source electrodes of the thin-film transistors 22a-1 may be electrically connected to the data lines DL. In the example of FIG. 34, 16 thin-film transistors 22a-1 arranged in four rows and four columns are shown.

The light detecting diodes 22a-2 may be arranged in the form of a matrix that extends in the first and second directions D1 and D2 and have a one-to-one correspondence with the thin-film transistors 22a-1. Each of the light detecting diodes 22a-2 may be electrically connected to one of the thin-film transistors 22a-1. The N-type electrodes of the light detecting diodes 22a-2 may be electrically connected to the drain electrodes of the thin-film transistors 22a-1. In the example of FIG. 34, sixteen light detecting diodes 22a-2 arranged in four rows and four columns are shown.

Each of the light detecting diodes 22a-2 may receive light from the scintillator, and convert the received light into a light detected voltage. The light detected voltage may be a voltage corresponding to a dose of X-rays.

The bias lines BL may be electrically connected to the light detecting diodes 22a-2. Each of the bias lines BL may be electrically connected to the P-type electrodes of the light detecting diodes 22a-2 arranged in a direction. For example, the bias lines 22a-2 may be arranged in substantially parallel to the second direction D2 to be electrically connected to the light detecting diodes 22a-2. Alternatively, the bias lines BL may be arranged in a direction substantially parallel to the first direction D1 to be electrically connected to the light detecting diodes 22a-2. In the example of FIG. 34, four bias lines BL arranged in the second direction D2 are shown.

The bias driver 22b may be electrically connected to the bias lines BL to apply a driving voltage to the bias lines BL. The bias driver 22b may apply a reverse bias or a forward bias selectively to the light detecting diodes 22a-2. A reference voltage may be applied to the N-type electrodes of the light detecting diodes 22a-2. The bias driver 22b may apply a voltage that is lower than the reference voltage to the P-type electrodes of the light detecting diodes 22a-2 to apply a reverse bias to the light detecting diodes 22a-2. Also, the bias driver 22b may apply a voltage that is higher than the reference voltage to the P-type electrodes of the light detecting diodes 22a-2 to apply a forward bias to the light detecting diodes 22a-2.

The gate driver 22C may be electrically connected to the gate lines GL to apply gate signals to the gate lines GL. The gate driver 22C may apply gate signals sequentially in the second direction D2 to the gate lines GL. For example, if the gate signals are applied to the gate lines GL, the thin-film transistors 22a-1 may be turned on. In contrast, if the gate signals are no longer applied to the gate lines GL, the thin-film transistors 22a-1 may be turned off.

The signal processor 22d may be electrically connected to the data lines DL to receive sample input voltages from the data lines DL. The signal processor 22d may output image data to the image processing apparatus 100 based on the sample input voltages. The image data may be an analog/digital signal corresponding to the light detected voltage.

The image data output from the X-ray detector 22 may itself configure an X-ray image. However, an image that is displayed on the display 120 by the image processing apparatus 100 may be an image resulting from performing various image processing on an X-ray image output from the X-ray detector 22 to improve the visibility of the X-ray image. The controller 130 of the image processing apparatus 100 may perform such image processing.

Although not shown in FIG. 34, if the X-ray detector 22 is embodied as a wireless detector or a portable detector, the X-ray detector 22 may further include a battery unit and a wireless communication interface unit.

Figure 35:
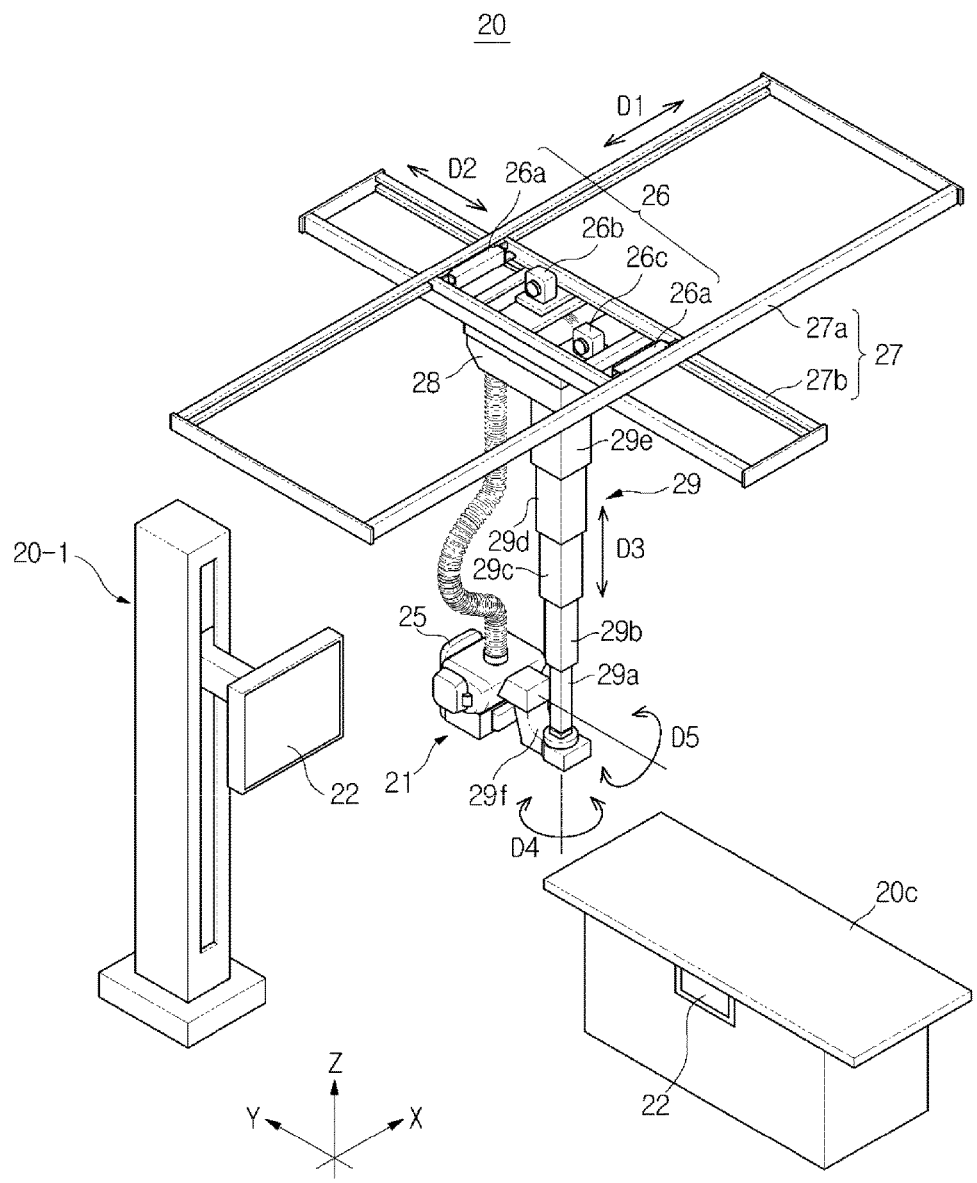
FIG. 35 shows an external appearance of a medical imaging apparatus which is a sealing type X-ray imaging apparatus according to an exemplary embodiment.
Figure 36:
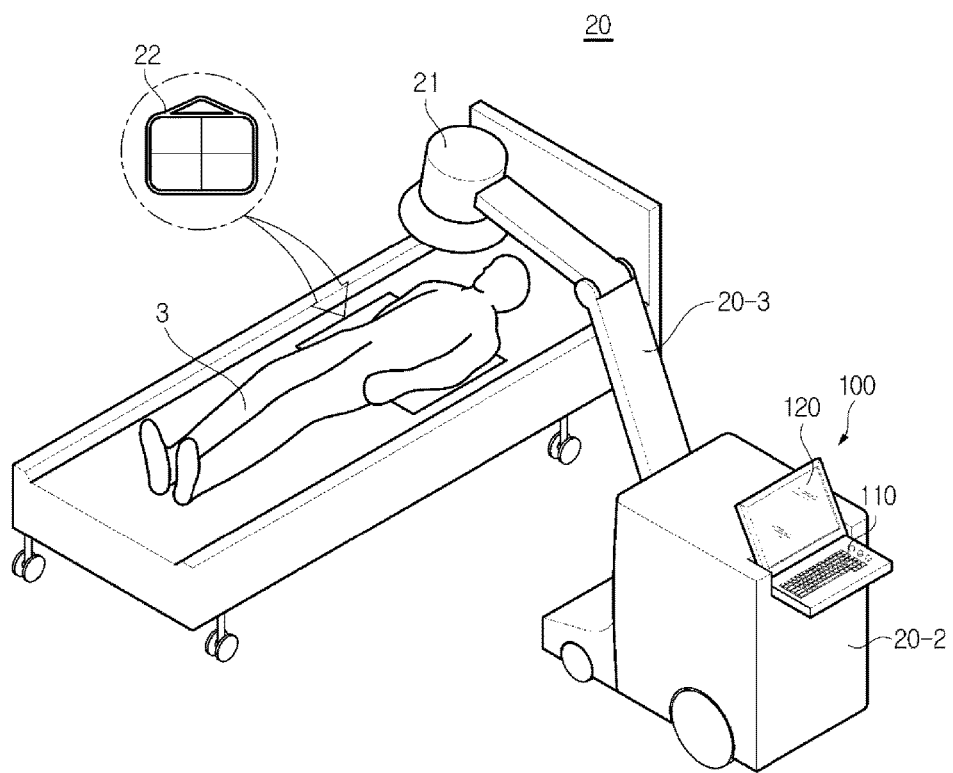
FIG. 36 shows an external appearance of a medical imaging apparatus which is a mobile X-ray imaging apparatus according to an exemplary embodiment.

FIG. 35 shows an external appearance of the medical imaging apparatus 20 according to an exemplary embodiment which is a sealing type X-ray imaging apparatus, and FIG. 36 shows an external appearance of the medical imaging apparatus 20 according to an exemplary embodiment which is a mobile X-ray imaging apparatus.

If the X-ray detector 22 is embodied as a wireless detector or a portable detector, the X-ray detector 22 may be used for various kinds of X-ray scanning by moving the X-ray detector 22 as needed.

In this case, as shown in FIG. 35, the X-ray imaging apparatus 20 may include a manipulator 25 to provide an interface for manipulating the X-ray imaging apparatus 20, a motor 26 to provide a driving force for moving the X-ray source 21, and a guide rail 27 to move the X-ray source 21 according to the driving force of the motor 26, a movement carriage 28, and a post frame 29.

The guide rail 27 may include a first guide rail 27a and a second guide rail 27b disposed at a predetermined angle with respect to the first guide rail 27a. The first guide rail 27a may be orthogonal to the second guide rail 27b.

The first guide rail 27a may be installed on the ceiling of an examination room where the X-ray imaging apparatus 20 is placed.

The second guide rail 27b may be disposed beneath the first guide rail 27a, and slide with respect to the first guide rail 27a. The first guide rail 27a may include a plurality of rollers (not shown) that are movable along the first guide rail 27a. The second guide rail 27b may connect to the rollers and move along the first guide rail 27a.

A direction in which the first guide rail 27a extends may be defined as a first direction D1, and a direction in which the second guide rail 27b extends may be defined as a second direction D2. Accordingly, the first direction D1 may be orthogonal to the second direction D2, and the first and second directions D1 and D2 may be parallel to the ceiling of the examination room.

The movement carriage 28 may be disposed beneath the second guide rail 27b, and move along the second guide rail 27b. The movement carriage 28 may include a plurality of rollers (not shown) to move along the second guide rail 27b.

Accordingly, the movement carriage 28 may be movable in the first direction D1 together with the second guide rail 27b, and movable in the second direction D2 along the second guide rail 27b.

The post frame 29 may be fixed on the movement carriage 28 and disposed below the movement carriage 28. The post frame 29 may include a plurality of posts 29a, 29b, 29c, 29d, and 29e.

The posts 29a, 29b, 29c, 29d, and 29e may connect to each other to be folded with each other. The length of the post frame 29 fixed on the movement carriage 28 may increase or decrease in an elevation direction (i.e., Z direction) of the examination room.

A direction in which the length of the post frame 29 increases or decreases may be defined as a third direction D3. Accordingly, the third direction D3 may be orthogonal to the first direction D1 and the second direction D2.

A revolute joint 29f may be disposed between the X-ray source 21 and the post frame 29. The revolute joint 29f may couple the X-ray source 21 with the post frame 29, and support a load applied to the X-ray source 21.

The X-ray source 21 connected to the revolute joint 29f may rotate on a plane that is perpendicular to the third direction D3. The rotation direction of the X-ray source 21 may be defined as a fourth direction D4.

Also, the X-ray source 21 may be rotatable on a plane that is perpendicular to the ceiling of the examination room.

Accordingly, the X-ray source 21 may rotate in a fifth direction D5 which is a rotation direction of an axis parallel to the first direction D1 and the second direction D2, with reference to the revolute joint 29f.

To move the X-ray source 21 in the first direction D1 through the third direction D3, a motor 26 may be provided. The motor 26 may be electrically driven, and may include encoders.

The motor 26 may include a first motor 26a, a second motor 26b, and a third motor 26c.

The first to third motors 26a to 26c may be arranged at appropriate locations in consideration of convenience of design. For example, the first motor 26a that is used to move the second guide rail 27b in the first direction D1 may be disposed around the first guide rail 27a, the second motor 26b that is used to move the movement carriage 28 in the second direction D2 may be disposed around the second guide rail 27b, and the third motor 26c that is used to increases or decreases the length of the post frame 29 in the third direction D3 may be disposed in the movement carriage 28.

As another example, the motor 26 may connect to power transfer device (not shown) to linearly move or rotate the X-ray source 21 in the first to fifth directions D1 to D5. The power transfer device may include a belt and a pulley, a chain and a sprocket, or a shaft.

As another example, motors 26a to 26c may be provided between the revolute joint 29f and the post frame 29 and between the revolute joint 29f and the X-ray source 21 to rotate the X-ray source 21 in the fourth and fifth directions D4 and D5.

If the X-ray detector 22 is embodied as a wireless detector or a portable detector, the X-ray detector 22 may be attached on the stand 20-1 or the patient table 20c when it is used for X-ray scanning. The X-ray detector 22 may be selected as one having an appropriate specification according to the kind of an object to be scanned or the purpose of diagnosis. When the X-ray detector 22 is not a wireless detector or a portable detector, the X-ray detector 22 may be fixed at the stand 20-1 or the patient table 20c.

If the X-ray detector 22 is embodied as a wireless detector or a portable detector, the X-ray detector 22 may be used in a mobile X-ray imaging apparatus 20.

Referring to FIG. 36, in the mobile X-ray imaging apparatus 20, both the X-ray source 21 and the X-ray detector 22 may move freely in a three dimensional (3D) space. More specifically, the X-ray source 21 may be attached on a movable main body 20-2 through a support arm 20-3, and the support arm 20-3 can rotate or adjust its angle to move the X-ray source 21. Also, since the X-ray detector 22 is a mobile X-ray detector, the X-ray detector 22 may also be placed at an arbitrary location in the 3D space.

The mobile X-ray imaging apparatus 20 can be used usefully to scan patients having difficulties in moving to an examination room or in taking a predetermined posture such as standing or lying.

In the above, an X-ray imaging apparatus that images the inside of an object using X-rays has been described as an example of the medical imaging apparatus 20, however, the medical imaging apparatus 20 may be any imaging apparatus using other radiation than X-rays. For example, the medical imaging apparatus 20 may be a positron emission tomography (PET) apparatus using gamma rays. The PET apparatus may inject medicine containing radioisotopes emitting positrons into a human body, and detect gamma rays emitted when positrons emitted from the human body disappear to thereby image the inside of an object.

Figure 37:
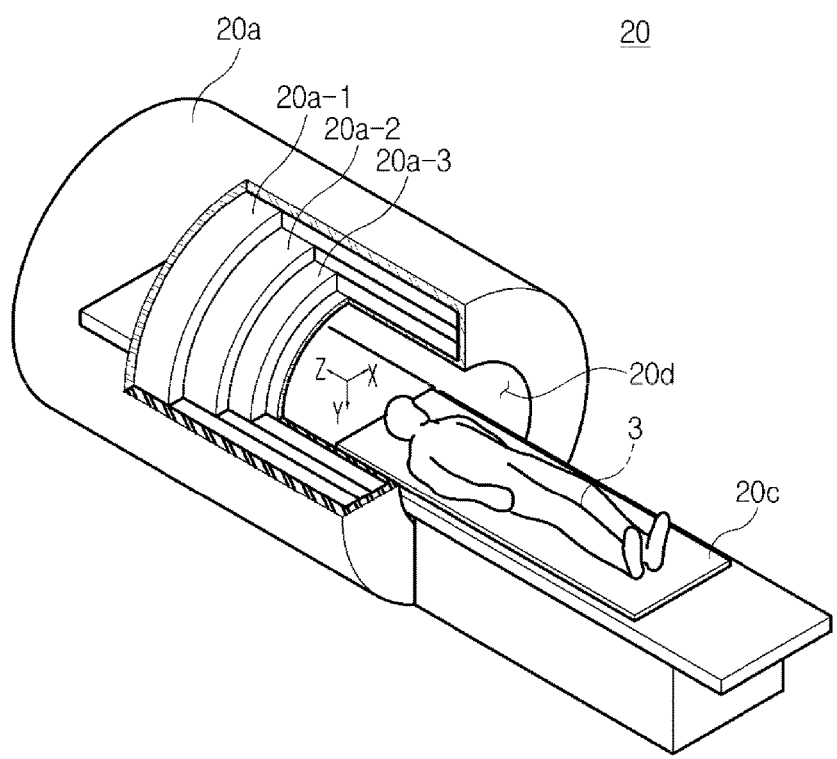
FIG. 37 shows an external appearance of a medical imaging apparatus which is a magnetic resonance imaging (MRI) apparatus according to an exemplary embodiment.

FIG. 37 shows an external appearance of a medical imaging apparatus according to an exemplary embodiment which is an MRI apparatus.

If the medical imaging apparatus 20 is an MRI apparatus, a static coil 20a-1 to form a static magnetic field in a bore 20d, a gradient coil 20a-2 to form a gradient magnetic field by making a gradient in the static magnetic field, and an RF coil 20a-3 to apply an RF pulse to an object to excite atomic nuclei and to receive an echo signal from the atomic nuclei may be provided in a housing 20a, as shown in FIG. 37.

More specifically, if the patent table 20c is conveyed into the bore 20d in which a static magnetic field is formed by the static coil 20a-1, the gradient coil 20a-2 may apply a gradient magnetic field, and the RF coil 20a-3 may apply an RF pulse to excite atomic nuclei consisting of an object 3 and to receive echo signals from the object, thereby imaging the inside of the object 3.

The medical imaging apparatus 20 described above with reference to FIGS. 30 to 37 may include the image processing apparatus 100. In this case, the image processing apparatus 100 may perform functions of a general workstation related to acquisition of medical images.

Meanwhile, according to another embodiment of the medical imaging apparatus, a window area selected by a user according to the above-described embodiment may be applied to collimate X-rays to adjust an irradiation area of the X-rays. The medical imaging apparatus according to the current embodiment may be an X-ray imaging apparatus.

Figure 38:
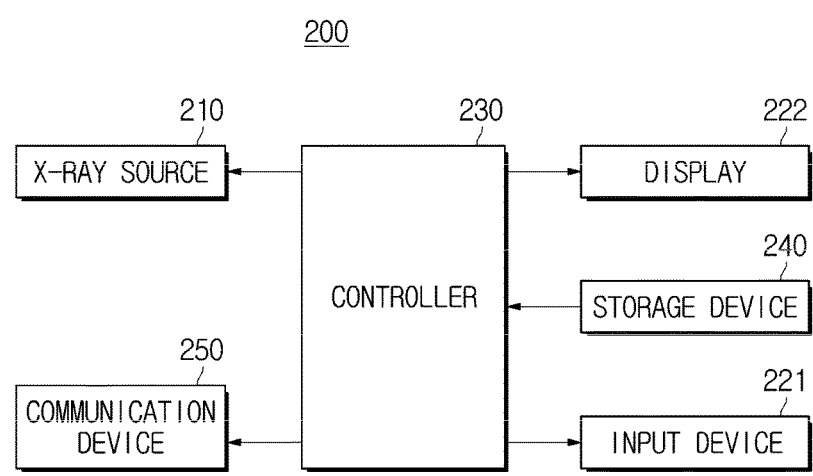
FIG. 38 is a control block diagram of an X-ray imaging apparatus according to another embodiment of the present disclosure.
Figure 39:
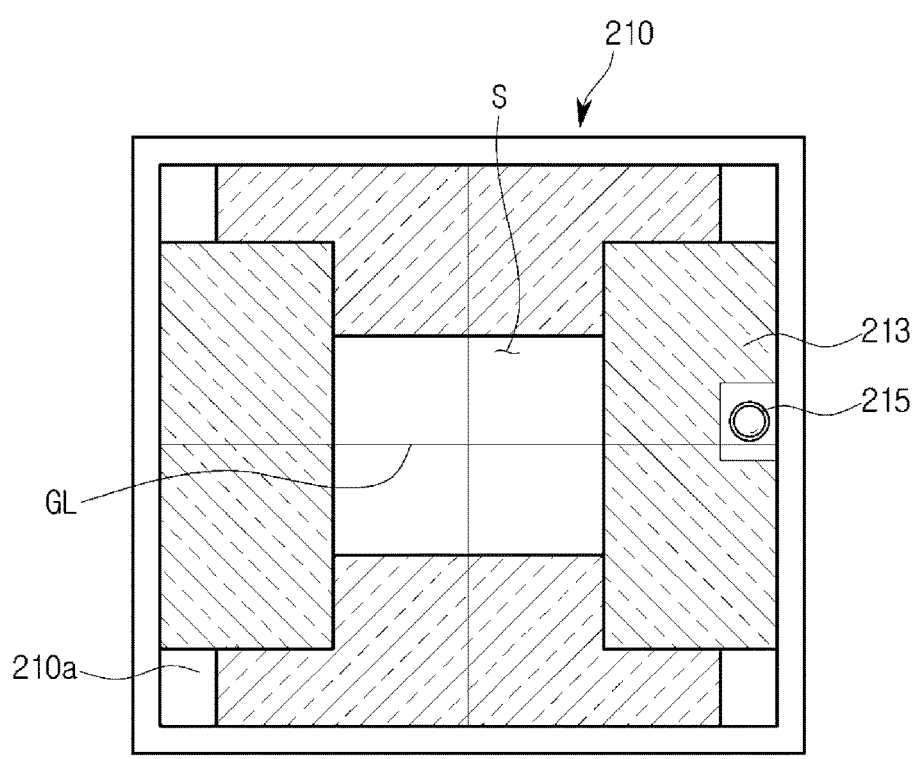
FIG. 39 is a diagram illustrating a position of a camera disposed in the X-ray imaging apparatus according to the another embodiment.

FIG. 38 is a control block diagram of an X-ray imaging apparatus according to another embodiment of the present disclosure and FIG. 39 is a diagram illustrating a position of a camera disposed in the X-ray imaging apparatus according to the another embodiment.

Referring to FIG. 38, an X-ray imaging apparatus 200 according to another embodiment of the present disclosure may include an X-ray source 210 to generate and irradiate X-rays, an input device 221 to receive a setting of a window area, a display 222 to guide an input for a window area and to display an X-ray image, a controller 230 to control operation of the X-ray source 210, a storage device 240 to store an X-ray image, and a communication device 250 to communicate with an external device.

According to the embodiment of the X-ray imaging apparatus 200, if the display 222 displays a guide image to guide a user's input, and the user sets a window area on the guide image through the input device 221, the controller 230 may control a collimator 213 (see FIG. 42) to form a collimation area corresponding to the window area.

The guide image displayed on the display 222 may be at least one image among an X-ray image acquired by irradiating a low dose of X-rays onto an object before main scanning (main X-ray imaging), a camera image acquired by photographing the object with a camera, and a previously acquired X-ray image of the object.

For example, the guide image acquired before main scanning may be a scout image.

Also, when an X-ray image of the object is again acquired for follow-up examination, a previously acquired X-ray image for the object may be displayed on the display 222 so that the user can set a window area on the previously acquired X-ray image.

Also, in case that the guide image is a camera image, a camera may be installed in the X-ray source 210, an object may be photographed by the camera before X-ray imaging, and camera image of the object may be displayed on the display 222.

FIG. 39 shows an X-ray source 210 viewed from the front. Here, a direction toward a front of the X-ray source 210 signifies a direction in which X-rays are radiated.

Referring to FIG. 39, the collimator 213 may be disposed in front of the X-ray source 110, and the camera 215 may be embedded in a region adjacent to the collimator 213.

While the X-ray source 210 captures an X-ray image of an object, the camera 215 captures a real image of the object, e.g., a target. In an embodiment to be described below, an image captured by the X-ray source 210 will be referred to as an X-ray image, and an image captured by the camera 215 will be referred to as a camera image.

The camera 215 may be disposed at a position at which a portion of an object to be imaged by X-rays may be captured. For example, the camera 215 may be mounted on the X-ray source 210 in a direction that is the same as a direction in which X-rays are radiated from the X-ray source 210. When the camera 215 is mounted on the X-ray source 210, the user may more easily set settings related to an X-ray image while looking at a camera image since an offset between a region shown in the X-ray image and a region shown in the camera image is reduced.

Since a housing 210a may be formed in front of the collimator 213, the housing 210a may be formed with a material such as a transparent resin or glass to minimize its influence on X-rays radiated from the X-ray tube.

The camera 215 may be mounted on an inner portion of the housing 110a as illustrated in FIG. 39. Alternatively, the camera 215 may also be mounted on an outer portion of the housing 110a. Here, the camera 215 may be mounted on a bezel provided at a circumference of the housing 210a. However, since an embodiment of the X-ray imaging apparatus 200 is not limited thereto, the camera 215 may be mounted on any position so long as an image of an object can be captured at the position.

In addition, a collimator guideline GL in a cross shape may be formed on the housing 210a formed in front of the collimator 213. When the X-ray irradiation region is irradiated with visible rays by a collimator lamp embedded in the X-ray source 210, the collimator guideline GL may be displayed at the center of the X-ray irradiation region and the user may intuitively recognize a position of the X-ray irradiation region by looking at the collimator guideline GL.

Hereinafter, an example of receiving a setting of a window area from a user will be described. For a detailed description, some of the above-described embodiments of the X-ray imaging apparatus 100 will be applied to the X-ray imaging apparatus 200 according to the current embodiment.

Figure 40:
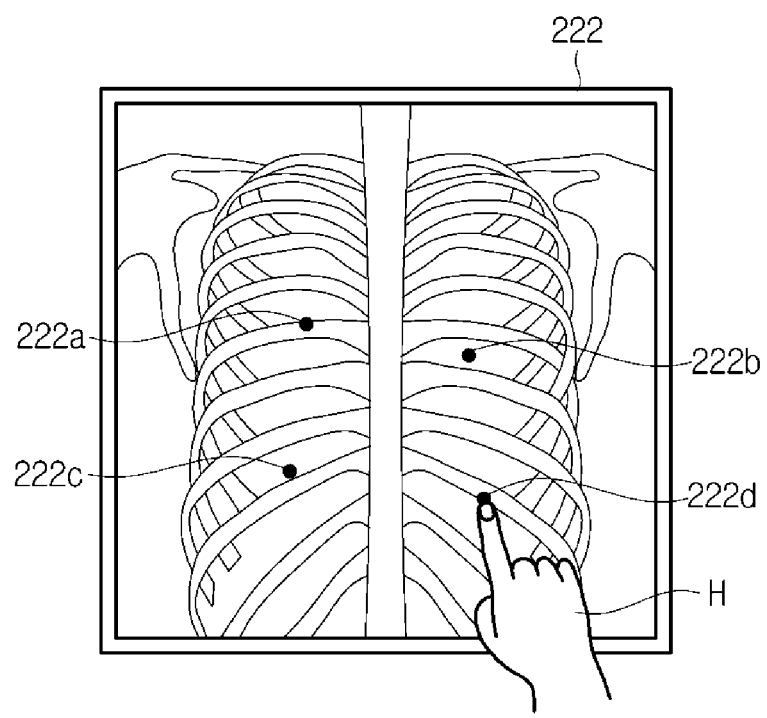
FIGS. 40 and 41 show an example in which the X-ray imaging apparatus according to the other embodiment of the present disclosure receives four points from a user order to set a window area.
Figure 41:
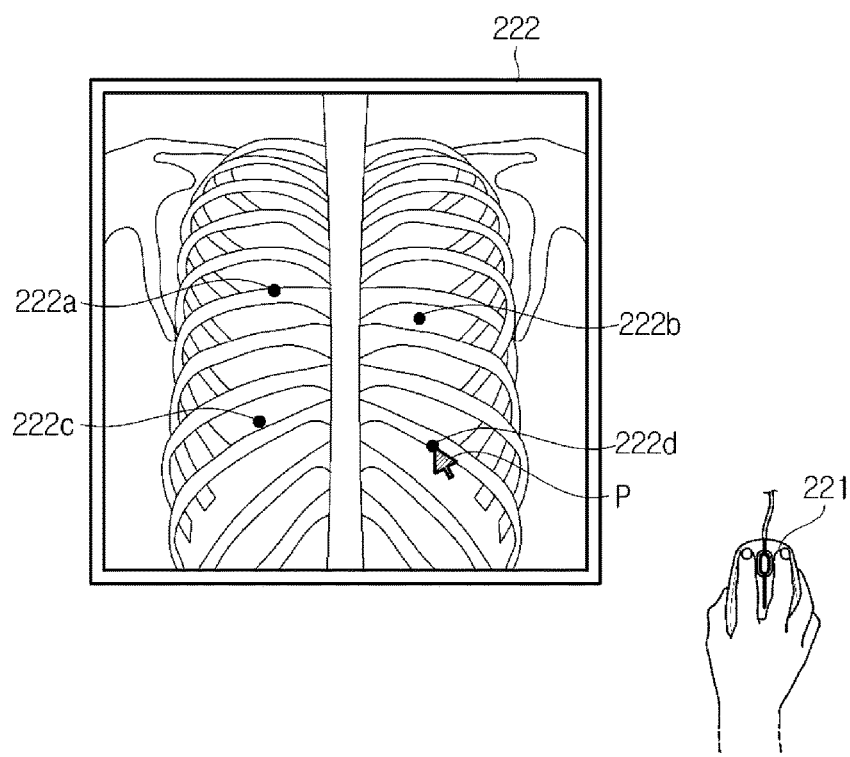
Figure 42:
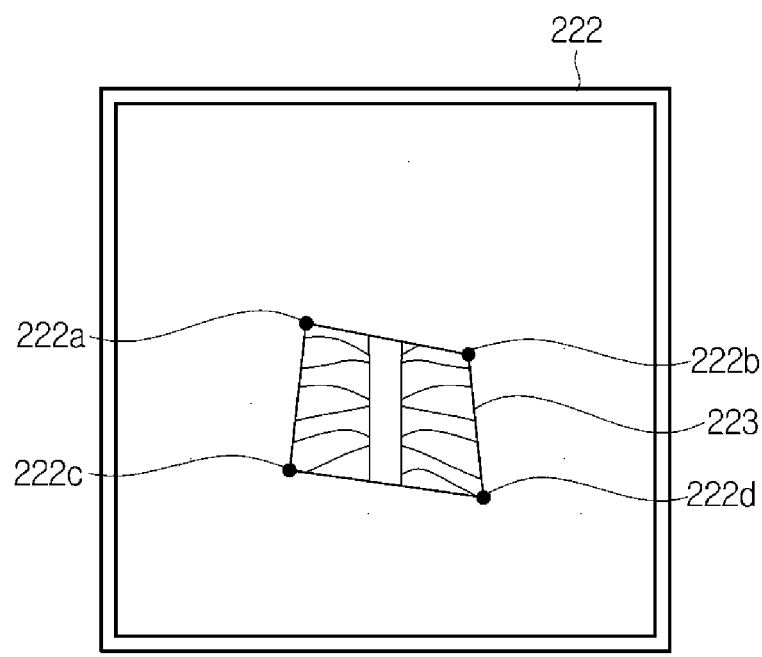
FIG. 42 shows a result obtained after the X-ray imaging apparatus performs collimation based on the four points.

FIGS. 40 and 41 show an example in which the X-ray imaging apparatus according to the other embodiment of the present disclosure receives four points from a user in order to set a window area, and FIG. 42 shows a result obtained after the X-ray imaging apparatus performs collimation based on the four points. An X-ray image is used as the guide image in this example.

The X-ray imaging apparatus 200 may allow a user to input n points (n is an integer that is equal to or greater than 3) on a medial image displayed on the display 222. FIG. 40 to FIG. 42 show a case of n=4.

If the input device 221 is implemented as a transparent touch panel to form a touch screen together with the display device 222, the user may touch locations corresponding to desired four points 222a, 222b, 222c, and 222d on an X-ray image displayed on the display 222 with his/her hand H to thereby input the four points 222a, 222b, 222c, and 222d, as shown in FIG. 40. At this time, the input points 222a, 222b, 222c, and 222d may be displayed on the display 222 so that the user can check the selected locations.

Alternatively, if the input device 221 is implemented as a mouse, a pointer p moving on the display 222 according to a movement amount and a movement direction of the input device 221 may be displayed on the display 222, as shown in FIG. 41. In this case, the user may use the input device 221 to locate the pointer p at locations corresponding to desired four points 222a, 222b, 222c, and 222d on a medical image, and then click the input device 221 to thereby input the four points 222a, 222b, 222c, and 222d.

If the four points 222a, 222b, 222c, and 222d are input on the X-ray image using any one of the above-described methods, a quadrangle defined by the four points 222a, 222b, 222c, and 222d, that is, a window 223 having a quadrangular shape whose vertices are the four points 222a, 222b, 222c, and 222d may be formed, as shown in FIG. 41. That is, the controller 230 may set a quadrangle whose vertices are the four points 222a, 222b, 222c, and 222d, to a window 223, and control a collimation area in order to acquire an X-ray image corresponding to a window area. Herein, the window area may be an area defined by the window 223.

Also, the controller 230 may determine validity of a point input by the user. For example, whenever a point is input, the controller 230 may determine validity of the input point. If the controller 230 determines that the input point is invalid, the controller 230 may display the result of the determination through the display 222.

If a distance between input points is smaller than a reference value, the controller 230 may determine that a last point is invalid.

Also, if at least three points of input points are located on a straight line, the controller 230 may determine that a last point is invalid.

Also, if a figure formed by input points has a concave shape, the controller 230 may determine that a last point is invalid.

Also, the controller 230 may determine whether a figure formed by input points has a concave shape, depending on whether an arrangement direction of a fourthly input point with respect to at least two of three points previously input is a counterclockwise direction or a clockwise direction.

If the controller 230 determines that all of the input points are valid, the controller 230 may connect each point to the other two points with a straight line to form a polygon.

If the controller 230 determines that any one of the input points is invalid, the input device 221 may receive a new point to replace the point determined to be invalid.

In the above-described example, the window area is a polygon, however, the window area may be set to a circle by receiving one or more points from the user, as described above in the embodiment of the image processing apparatus 100.

For example, if two points are input through the input device 221, the controller 230 may set a circle whose diameter or radius is a straight line connecting the two points, to a window area.

Also, if a point and a straight line starting from the point are input through the input device 221, the controller 230 may set a circle whose center is the input point and whose radius is the straight line, to a window area. Or, the controller 230 may set a circle whose diameter is the straight line, to a window area.

Also, if a point is input through the input device 221, the controller 230 may create a circle whose center is the input point, and increase the radius of the circle in proportion to a time period for which the point is input. The controller 230 may set a circle of a radius acquired at time at which the point is no longer input, to a window area.

Figure 43:
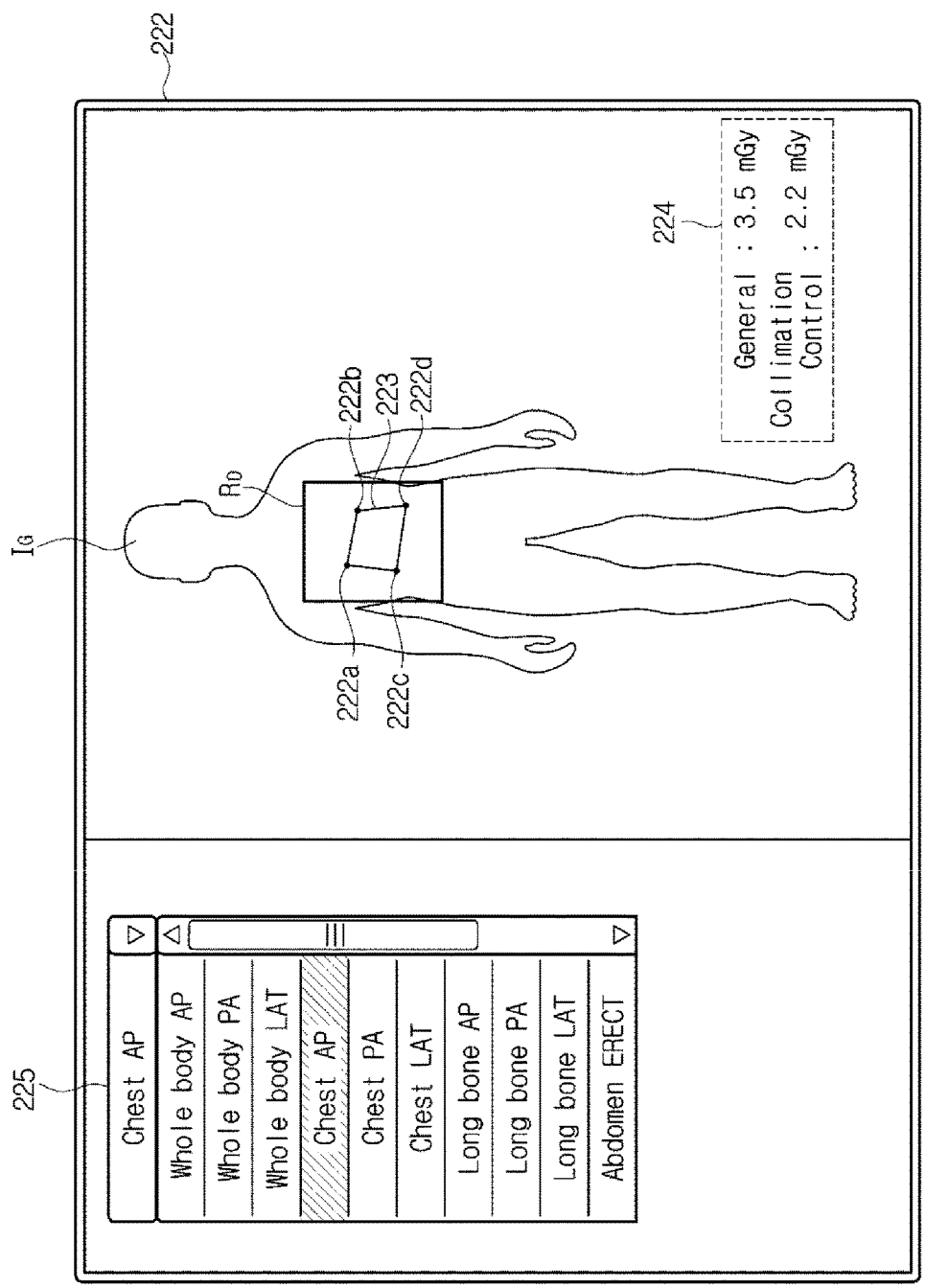
FIG. 43 shows an example in which the X-ray imaging apparatus according to the other embodiment of the present disclosure uses a camera image as a guide image.

FIG. 43 shows an example in which the X-ray imaging apparatus according to the other embodiment of the present disclosure uses a camera image as the guide image.

Referring to FIG. 43, display 222 may display a camera image $I_G$. The user may set a window area using camera image $I_G$ as the guide image.

Display 222 may further display a protocol list 225 to receive a selection of the imaging protocol from the user.

An X-ray imaging region may change for each imaging protocol, and a suitable X-ray irradiation condition may change for each X-ray imaging region. The imaging protocol may be determined according to an X-ray imaging portion, a posture of an object, and the like. For example, imaging protocols may include whole body anterior-posterior (AP), whole body posterior-anterior (PA), and whole body lateral (LAT), may also include chest AP, chest PA, and chest LAT, and may also include long bone AP, long bone PA and long bone LAT for long bones such as a leg bone. In addition, the imaging protocols may also include abdomen erect.

If the user select one among the imaging protocols included in the protocol list 225, display 222 may display a region C corresponding to the selected imaging protocol on the guide image $I_G$. The user may set the window area within the displayed region C.

Also, display 222 may display a value of X-ray dose which the object is exposed to when the collimation area is adjusted to match the window area set by the user and a value of X-ray dose which the object is exposed to when the collimation area is adjusted to a region generally set for the selected protocol in an region 224. The user may intuitively recognize a dose reduction effect according to the adjustment of the collimation area by looking at the displayed values.

Also, above descriptions related to operation of setting a window area in the embodiment of the image processing apparatus 100 can be applied to the X-ray imaging apparatus 200. In order to avoid redundant descriptions, further descriptions about operation of setting a window area will be omitted.

Figure 44:
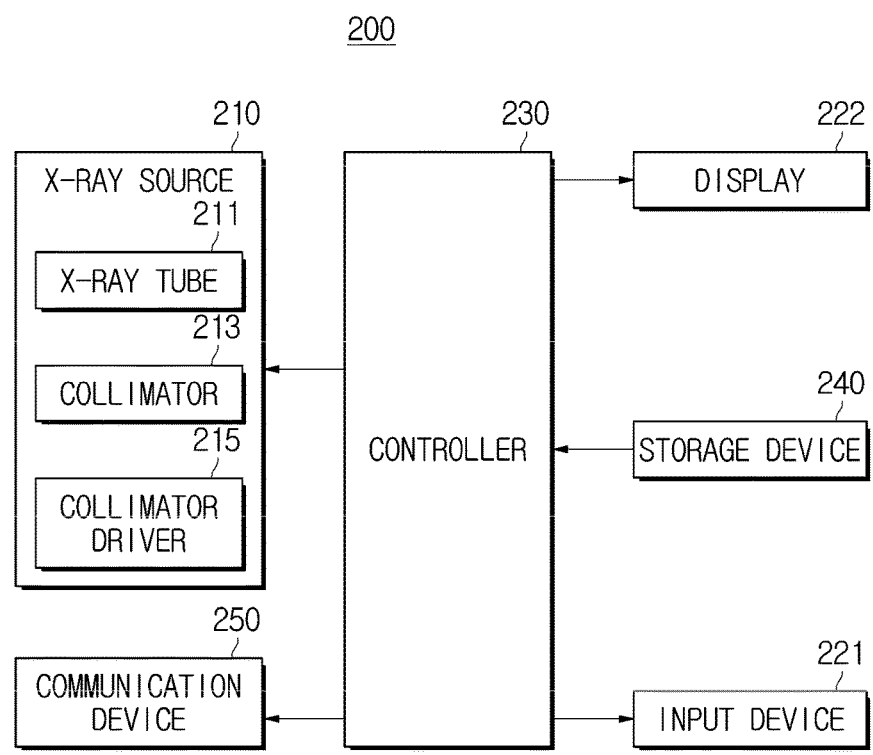
FIG. 44 is a control block diagram of an X-ray source of the X-ray imaging apparatus according to the other embodiment of the present disclosure.
Figure 45:
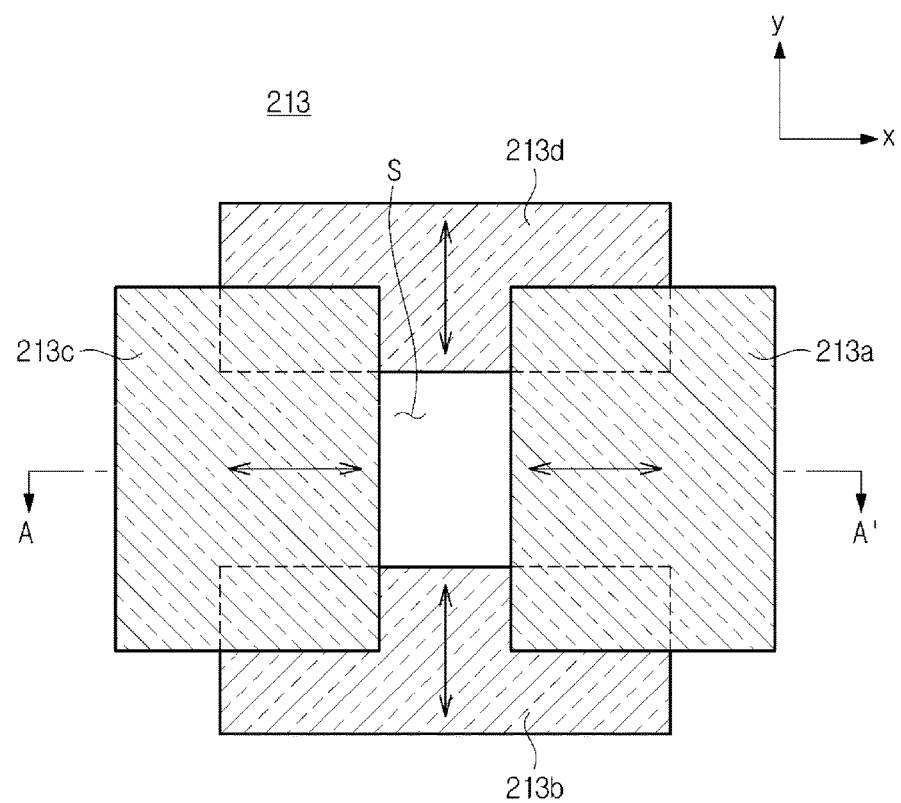
FIG. 45 is a top view showing a structure of a collimator used in the X-ray imaging apparatus according to the other embodiment of the present disclosure.
Figure 46:
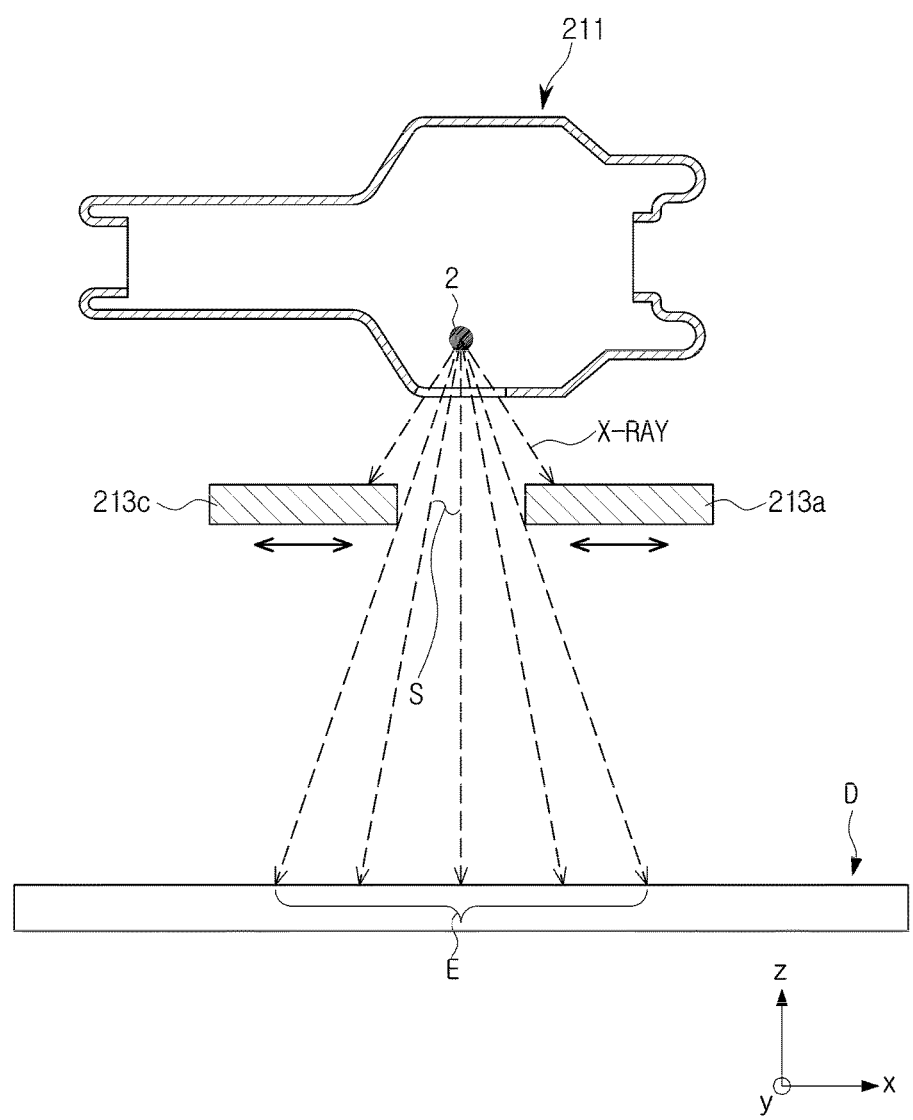
FIG. 46 is a side sectional view of blades of the collimator used in the X-ray imaging apparatus according to the other embodiment of the present disclosure, cut along a line A-A' shown in FIG. 45.

FIG. 44 is a control block diagram of an X-ray source of the X-ray imaging apparatus according to the another embodiment of the present disclosure, FIG. 45 is a top view showing a structure of a collimator used in the X-ray imaging apparatus according to the other embodiment of the present disclosure, and FIG. 46 is a side sectional view of blades of the collimator used in the X-ray imaging apparatus according to the other embodiment of the present disclosure, cut along a line A-A' shown in FIG. 45.

Referring to FIG. 44, the X-ray source 210 may include an X-ray tube 211 to generate X-rays, a collimator 213 to perform collimation on X-rays generated by the X-ray tube 211 and to adjust an irradiation area of the X-rays, and a collimator driver 217 to move the blades constituting the collimator 213.

The collimator 213 may include at least one movable blade, and the blade may be formed of a material having a high bandgap to absorb X-rays. The blade may move to adjust an irradiation area of X-rays, that is, a collimation area, and the collimator driver 217 may include a motor for supplying power to each blade, and a driving circuit for driving the motor.

The controller 230 may calculate a movement amount of each blade in correspondence to a collimation area, and transmit a control signal for moving the blade by the calculated movement amount to the collimator driver 217.

For example, the collimator 213 may include four blades 213a, 213b, 213c, and 213d each formed in the shape of a rectangular flat plate, as shown in FIG. 45. Each of the blades 213a, 213b, 213c, and 213d may move in an X-axis direction or in a Y-axis direction, or may rotate in a clockwise direction or in a counterclockwise direction on any location of the flat plane as an axis of rotation.

X-rays may be irradiated through a slot S formed by the plurality of blades 213a, 213b, 213c, and 213d. By passing X-rays through the slot S, collimation may be performed. Accordingly, the slot S formed by the plurality of blades 213a, 213b, 213c, and 213d may be defined as a collimation area.

Referring to FIG. 46, the collimator 213 may be disposed in a front direction from the X-ray tube 211. Herein, the front direction from the X-ray tube 211 may be a direction in which X-rays are irradiated.

X-rays incident onto the blades 213a, 213b, 213c, and 213d among X-rays irradiated from the X-ray tube 211 may be absorbed in the blades 213a, 213b, 213c, and 213d, and X-rays passed through the collimation area may be incident onto an X-ray detector D. Accordingly, an irradiation area of X-rays irradiated from a focal point 2 of the X-ray tube 211 may be limited by the collimator 213, and scattering of the X-rays may be reduced. By preventing X-rays from being irradiated onto an unnecessary area, it is possible to perform X-ray imaging with a low dose of X-rays.

In the example of FIG. 46, the first blade 213a and the third blade 213c may be located on the same plane. However, according to another example, the plurality of blades 213a, 213b, 213c, and 213d may be respectively located on different planes. If the plurality of blades 213a, 213b, 213c, and 213d are respectively located on different planes, the plurality of blades 213a, 213b, 213c, and 213d may move while overlapping with each other so as to form more various shapes of collimation areas.

The controller 230 may control the collimator 213 based on a relation between the collimation area and the window area to thereby acquire an X-ray image corresponding to the window area. The X-ray image corresponding to the window area may be an X-ray image having the same or similar size and shape as those of the window area.

If an X-ray image to be used as a guide image is acquired, the first blade 213a and the third blade 213c may move in the X-axis direction, and the second blade 213b and the fourth blade 213d may move in the Y-axis direction to form a collimation area in the shape of a rectangle. Like the above-described example, if an input for selecting a collimation area is received from a user, the blades 213a, 213b, 213c, and 213d may again move in order to irradiate X-rays to the selected collimation area.

The controller 230 may decide a movement direction and a movement amount of which one(s) of the blades 213a, 213b, 213c, and 213d for forming a collimation area corresponding to the window area, generate a control signal, and transmit the control signal to the collimator driver 217. The collimation area corresponding to the window area may be a collimation area required for creating an X-ray image having the same or similar size and shape as those of the window area. The shape of the collimation area may be the same as or similar to that of the window area, and the size of the collimation area may be proportional to that of the window area.

The collimator driver 217 may generate a driving signal according to the received control signal, and transmit the driving signal to the corresponding blade(s).

Figure 47:
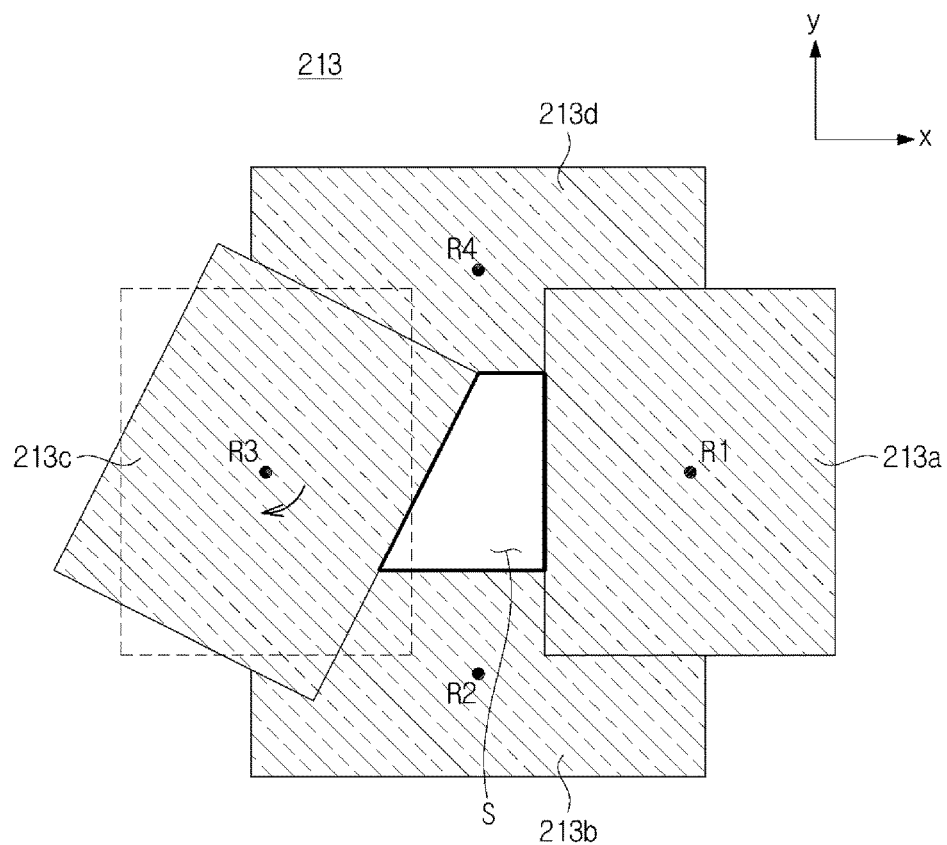
FIGS. 47, 48, and 49 show examples in which a blade of the collimator used in the X-ray imaging apparatus according to the other embodiment of the present disclosure moves.
Figure 48:
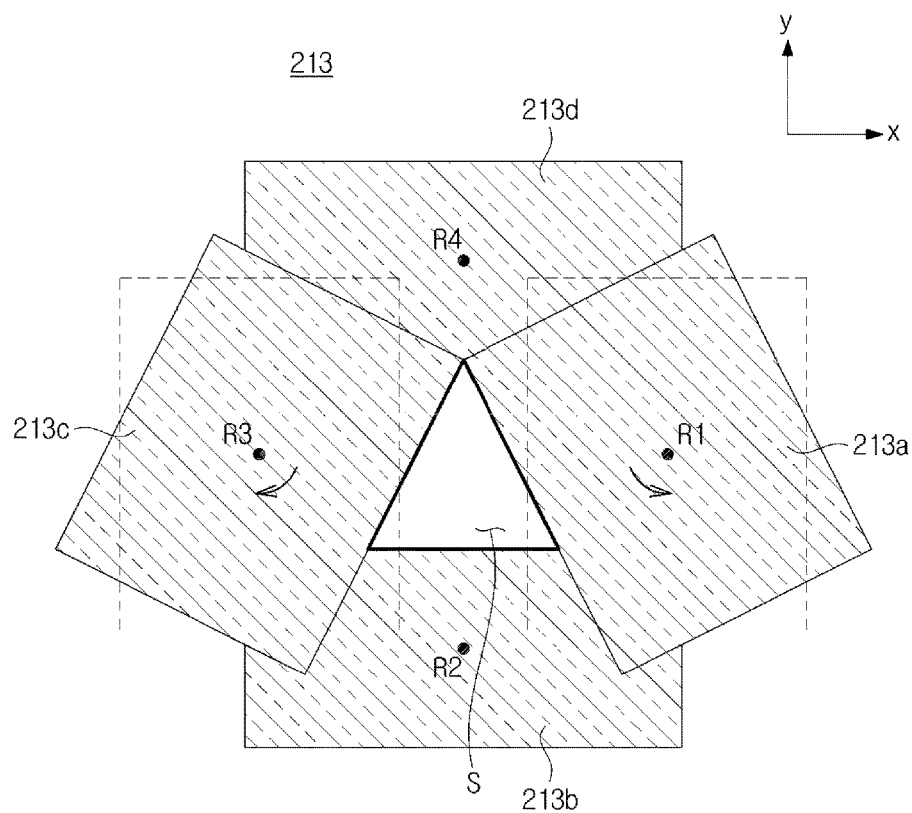
Figure 49:
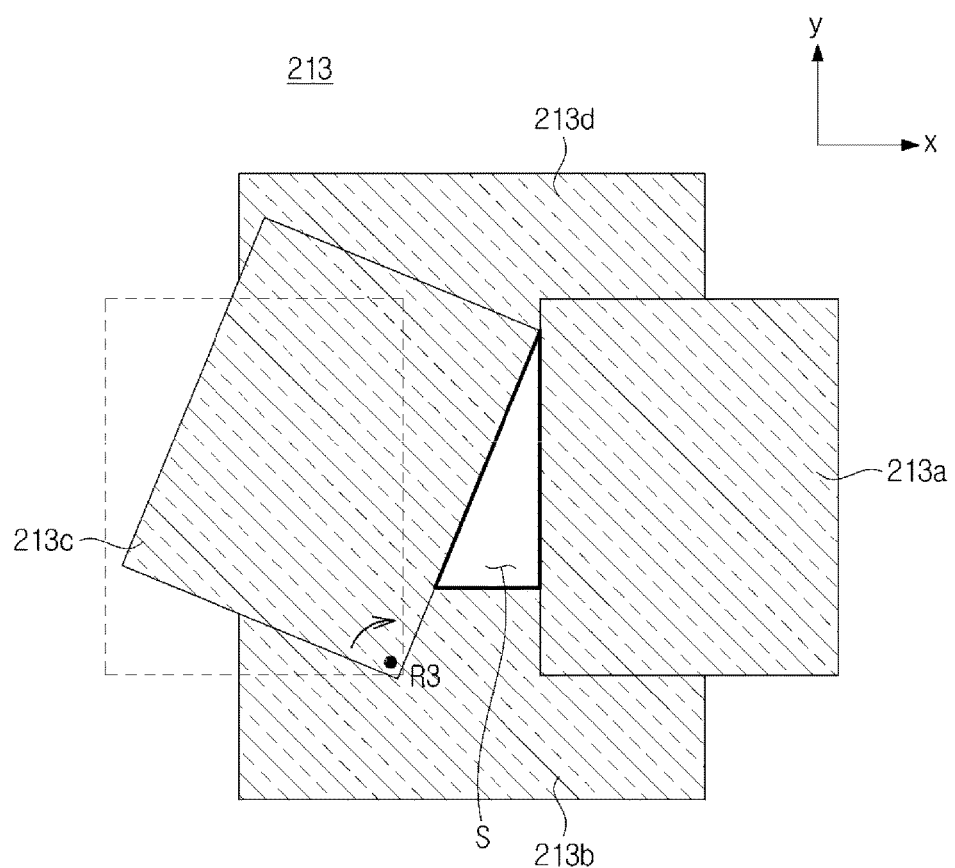

FIGS. 47, 48, and 49 show examples in which a blade of the collimator used in the X-ray imaging apparatus according to the other embodiment of the present disclosure moves.

For example, at least one of the plurality of blades 213a, 213b, 213c, and 213d may rotate in the clockwise direction or in the counterclockwise direction on the center as an axis of rotation.

Referring to FIG. 47, if the third blade 213c rotates in the clockwise direction on the center as an axis R3 of rotation, a collimation area may be formed in the shape of a trapezoid.

Also, the first blade 213a may also be configured to be rotatable in the clockwise direction or in the counterclockwise direction on the center as an axis R1 of rotation, the second blade 213b may also be configured to be rotatable in the clockwise direction or in the counterclockwise direction on the center as an axis R2 of rotation, and the fourth blade 213d may also be configured to be rotatable in the clockwise direction or in the counterclockwise direction on the center as an axis R4 of rotation.

If the plurality of blades 213a, 213b, 213c, and 213d are rotatable, a collimation area may be formed in the shape of a triangle by rotating the first blade 213a in the counterclockwise direction and rotating the third blade 213c in the clockwise direction, as shown in FIG. 48.

Meanwhile, rotational movements and linear movements of the blades 213a, 213b, 213c, and 213d may be combined. For example, by rotating one of the first blade 213a and the third blade 213c and linearly moving the other one in the X-axis direction to approach the one, a collimation area may be formed in the shape of a triangle, as shown in FIG. 48. Accordingly, only a rotation movement or a combination of a rotation movement and a linear movement may be used according to a desired shape of a triangle.

According to another example, at least one of the plurality of blades 213a, 213b, 213c, and 213d may use one of its four vertices as a center of rotation.

In this case, by rotating the third blade 213c in the clockwise direction on its one vertex as the axis R3 of rotation, a collimation area may be formed in the shape of a triangle, as shown in FIG. 49.

The above-described examples relate to cases of forming a collimation area in the shapes of a trapezoid and a triangle by rotating at least one blade, however, the embodiment of the X-ray imaging apparatus 200 is not limited to these examples. That is, by appropriately combining rotational movements and linear movements of the blades 213a, 213b, 213c, and 213d, a collimation area may be formed in the shape of another polygon not shown in the above-described examples.

Meanwhile, the controller 230 may additionally perform image processing on an X-ray image created by X-rays passed through the collimation area. More specifically, if a user sets a polygon shape having four vertices or less, such as a quadrangle or a triangle, to a window area, the controller 230 may control the collimator 213 to form a collimation area of the polygon shape, and additionally perform shutter processing on an X-ray image or cut off an unnecessary part from the X-ray image to thereby acquire an X-ray image more similar to the user's desired shape. At this time, the original X-ray image may be stored in the storage device 240, without being deleted.

Meanwhile, if the window area set by the user cannot be formed by the collimator 213, the controller 230 may combine the control of the collimator 213 with image processing to acquire an X-ray image corresponding to the window area set by the user. Herein, the X-ray image corresponding to the window area may be an X-ray image having the shape of the window area, or the remaining area excluding the window area may be an X-ray image having low definition and low brightness.

For this, the controller 230 may determine whether the collimator 213 can form a collimation area having a polygon shape defined by points input by a user, before controlling the collimator 213. If the controller 230 determines that the collimator 213 cannot form a collimation area having a polygon shape defined by points input by a user, the controller 230 may control the collimator 213 to form a collimation area of a shape most similar to the corresponding polygon.

For example, if the window area set by the user is a pentagon or a circle, the controller 230 may form a collimation area of a quadrangle or a triangle most similar to the window area, and perform shutter processing of reducing brightness or definition of the remaining area except for the window area from an X-ray image corresponding to the collimation area, or perform image processing of cutting off the remaining area.

Figure 50:
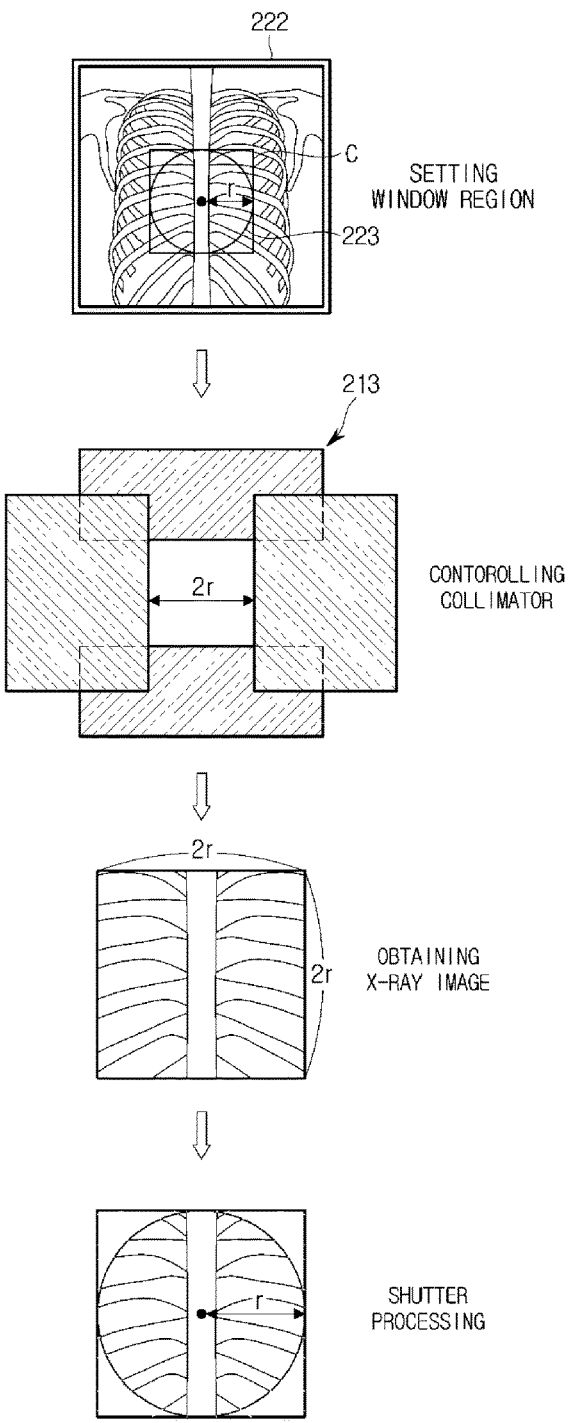
FIG. 50 is a view for describing an example of creating an X-ray image corresponding to a window area by combining the control of the collimator with image processing, in the X-ray imaging apparatus according to the other embodiment of the present disclosure.

FIG. 50 is a view for describing an example of creating an X-ray image corresponding to a window area by combining the control of the collimator with image processing, in the X-ray imaging apparatus according to the other embodiment of the present disclosure.

As shown in FIG. 50, if a window area set by a user is in the shape of a circle having a diameter 2r, the controller 230 may determine that it is impossible to form a collimation area having a the shape of the circle.

The display 222 may display a collimation window C representing a collimation area that can be formed by the collimator 213 together with the window 223 set by the user. Also, the display 222 may further display region in which image processing is performed within the collimation window C. Thus, the user may intuitively recognize the region in which the collimation is performed and the region in which the image processing is performed.

The controller 230 may control the collimator 213 to acquire an X-ray image in the shape of a square whose one side is equal to the diameter 2r of the circle in length.

If the X-ray image is acquired in the shape of the square, the controller 230 may perform shutter processing on the remaining area except for an area occupied by the circle having the diameter 2r to thus create an X-ray image corresponding to the window area set by the user. Details about the shutter processing have been described above in the embodiment of the image processing apparatus 100. Alternatively, the controller 230 may cut off the remaining area as necessary. In this case, the original X-ray image may be stored in the storage device 240.

The communication device 250 may transmit the original X-ray image or the image-processed image to a central server that manages medical images, or to the user's personal computer.

Hereinafter, an image processing method according to an exemplary embodiment will be described.

To perform an image processing method according to an exemplary embodiment, the image processing apparatus 100 according to the exemplary embodiments as described above can be used. Accordingly, the above description related to the image processing apparatus 100 can be applied to the image processing method according to an exemplary embodiment.

Figure 51:
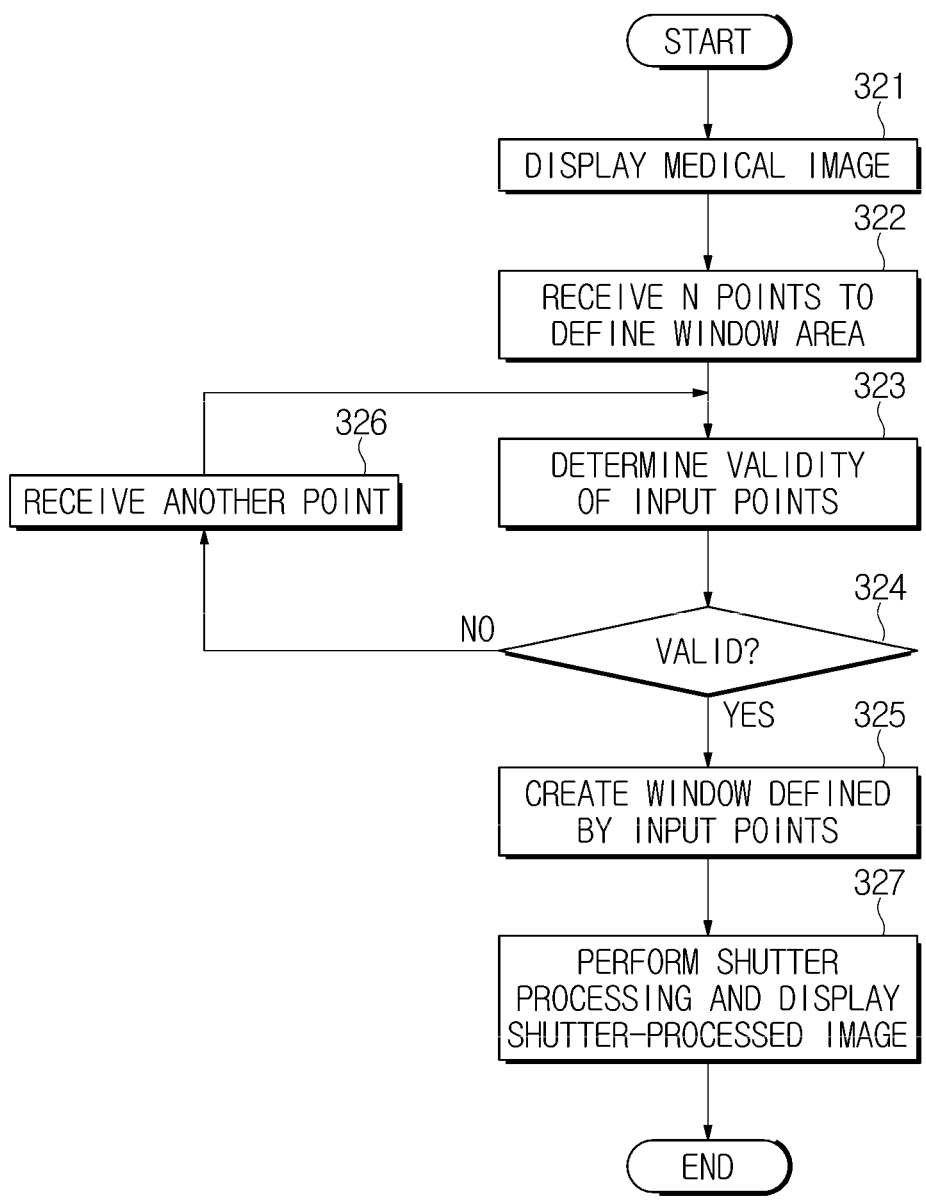
FIG. 51 is a flowchart illustrating an image processing method according to an exemplary embodiment.

FIG. 51 is a flowchart illustrating an image processing method according to an exemplary embodiment.

Referring to FIG. 51, a medical image may be displayed on the display 120, in operation 321. The medical image may be an image stored in the storage unit 150 or an image received from another external apparatus or system.

Then, n points may be received to define a window area, in operation 322. If a window to be set is a polygon whose vertexes are n points, n may be an integer that is greater than or equal to 3, and if a window to be set is a circle, n may be an integer that is greater than or equal to 1. The points may be input through the input unit 110. Since a user can input points while viewing the medical image displayed on the display 120, the user can set his/her desired area to a window area. A method of inputting points has been described above in the above exemplary embodiments, and accordingly, further descriptions thereof will be omitted.

Then, validity of the input points may be determined, in operation 323. If two points or more are input, it may be determined whether the input points are spaced a reference distance or more apart from each other, and if three points or more are input to set a window of a polygon, it may be determined whether the three points or more are on a straight line. Also, if four points or more are input to set a window of a polygon, it may be determined whether at least one of the internal angles of a quadrangle formed by connecting the four input points to each other is 180 degrees or more to prevent a window having a concave shape from being set. A method of determining validity of input points has been described above in the exemplary embodiment of the image processing apparatus 100.

In the flowchart as shown in FIG. 38, for convenience of description, operation of inputting points and operation of determining validity of points are described as different operations, however, by determining, whenever each of a plurality of points is input, validity of the point to allow a user to immediately correct any wrong point, it is possible to increase the speed of process.

If it is determined that any one of the input points is invalid based on the results of the determination on the validity of the points ("No" in operation 324), another point may be received, in operation 326, and if it is determined that all of the input points are valid ("Yes" in operation 324), a window that is defined by the input points may be created, in operation 325.

Then, shutter processing may be performed to reduce the brightness of the remaining area except for the window area in the medical image displayed on the display 120 to render the remaining area appear dark, or to reduce the definition of the remaining area to render the remaining area appear blurry, and the shutter-processed image may be displayed on the display 120, in operation 327. Since the remaining area except for the window area is not cut off although shutter processing is performed on the medical image to reduce the brightness or definition of the remaining area, image information about the remaining area is not deleted. Accordingly, the user may acquire information about the remaining area, in addition to information about the window area, from the shutter-processed medical image.

The shutter-processed medical image may be temporarily or non-temporarily stored in the storage unit 150, and the original image may also be stored in the storage unit 150 without being deleted. Also, the shutter-processed medical image may be transmitted to another apparatus or system through the communicator 150.

According to whether the image processing apparatus 100 performing the image processing method is included in the medical imaging apparatus 20, the central server 10, or the user control apparatus 30, the shutter-processed medical image may be transmitted to another apparatus among the medical imaging apparatus 20, the central server 10, or the user control apparatus 30, through the communicator 150.

Hereinafter, an embodiment of a method of controlling an X-ray imaging apparatus will be described. The X-ray imaging apparatus may be the X-ray imaging apparatus 200 described above. Accordingly, above descriptions about the embodiments of the X-ray imaging apparatus 200 will be applied to the method of controlling the X-ray imaging apparatus.

Figure 52:
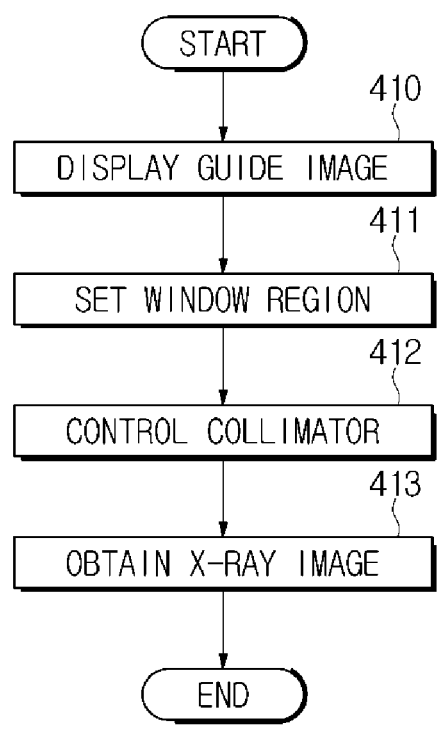
FIG. 52 is a flowchart illustrating a method of controlling an X-ray imaging apparatus according to an embodiment of the present disclosure.

FIG. 52 is a flowchart illustrating a method of controlling an X-ray imaging apparatus according to an embodiment of the present disclosure.

Referring to FIG. 52, a guide image for guiding a user's input may be displayed, in operation 410. The guide image may be an X-ray image acquired with a low dose of X-rays, a camera image photographed by a camera, or a previously photographed X-ray image of the same object.

If a user inputs n points (n is an integer that is greater than or equal to 1) for defining a window area on the guide image displayed on the display 222, the controller 230 may set an area defined by the input points to a window area, in operation 411. Also, the controller 230 may determine validity of the input points, and receive a new input from the user according to the result of the determination on the validity. Details about the operation have already been described in the above embodiment of the image processing method.

The controller 230 may control the collimator 213 in order to acquire an X-ray image for the set window area, in operation 412. The controller 230 may adjust the collimator 213 based on a relation between a collimation area and a window area to thereby form a collimation area of a shape and size corresponding to those of the window area. The controller 230 may form a collimation area having a desired shape and size by appropriately combining rotational movements and linear movements of the blades 213a, 213b, 213c, and 213d. For example, the controller 230 may rotate at least one of the plurality of blades 213a, 213b, 213c, and 213d constituting the collimator 213 in the clockwise direction or in the counterclockwise direction to form a collimation area of a polygon, such as a triangle or a quadrangle. Details about the control of the collimator 213 have been described above in the embodiment of the X-ray imaging apparatus 200.

If X-rays passed through the collimation area is incident onto the X-ray detector 200, an X-ray image corresponding to the window area may be acquired, in operation 413. Or, image processing may be additionally performed on the X-ray image created by the X-rays passed through the collimation area. More specifically, if the user sets a polygon shape having four vertices or less, such as a quadrangle or a triangle, to a window area, the controller 230 may control the collimator 213 to form a collimation area corresponding to the set shape, and additionally perform shutter processing on an X-ray image, or cut off an unnecessary part from the X-ray image to thereby acquire an X-ray image more similar to the user's desired shape. At this time, the original X-ray image may be stored in the storage device 240, without being deleted.

Meanwhile, if the window area set by the user cannot be formed by the collimator 213, the controller 230 may combine the control of the collimator 213 with image processing to acquire an X-ray image corresponding to the window area set by the user. For example, if the window area set by the user is a pentagon or a circle, the controller 230 may form a collimation area of a quadrangle or a triangle most similar to the window area, and perform shutter processing on an X-ray image corresponding to the collimation area.

According to the image processing apparatus 100 and the image processing method as described above, since points corresponding to n vertexes of a window of a polygon to be set in a medical image displayed on a display are received from a user, the user may accurately set a window.

Also, since only an operation of inputting n points is needed to set a window in a medical image, a complicated workflow of entering an editing mode after a window of a quadrangle is created may be avoided.

Also, since the validity of a point is determined whenever the point is input by a user, the user may immediately correct the input point that is determined as invalid, thereby resulting in an increase of processing speed.

Also, by controlling the collimator to form a collimation area corresponding to a window area, it is possible to prevent X-rays from being irradiated onto an unnecessary area, thereby implementing X-ray imaging with a low dose of X-rays.

According to the image processing apparatus and the image processing method according to the exemplary embodiments, by performing shutter processing with respect to a desired area through a simple operation of a user input, it is possible to reduce a workflow and to improve the accuracy of shutter processing.

The image processing methods according to the exemplary embodiments may be recorded as programs that can be executed on a computer and implemented through general-purpose digital computers which can run the programs using a computer-readable recording medium. Data structures described in the above methods can also be recorded on a computer-readable recording medium in various manners.

Examples of the computer-readable recording medium include storage media such as magnetic storage media (e.g., read-only memories (ROMs), floppy disks, hard disks, etc.) and optical recording media (e.g., CD-ROMs or DVDs). Furthermore, the computer-readable recording media may include computer storage media and communication media. The computer storage media may include both volatile and nonvolatile and both detachable and non-detachable media implemented by any method or technique for storing information such as computer-readable instructions, data structures, program modules or other data. The communication media may store computer-readable instructions, data structures, program modules, other data of a modulated data signal such as a carrier wave, or other transmission mechanism, and may include any information transmission media.

Although a few embodiments have been shown and described, it would be appreciated by those skilled in the art that changes may be made in these embodiments without departing from the principles and spirit of the disclosure, the scope of which is defined in the claims and their equivalents.

What is claimed is:

1. An X-ray imaging apparatus comprising:
    a collimator including a plurality of blades to form a collimation area, wherein at least one blade of the plurality of blades is rotatable in a clockwise direction or in a counterclockwise direction;
    a display configured to display a guide image;
    an input device configured to receive n (n being an integer equal to or greater than three) number of input points with respect to the displayed guide image; and
    at least one processor configured to:
        set a polygon defined by the input points to a window area, and control the collimator to form a collimation area having a shape of the polygon defined by the input points, the collimator controlled to perform at least one movement of a rotational movement and a linear movement of at least one of the plurality of blades to place intersection points of the plurality of blades at locations of the input points, respectively, and
        control the collimator to form a collimation area of a shape most similar to the polygon defined by the input points, in response to determining that the intersection points of the plurality of blades cannot be placed at the locations of the input points, respectively, by any of the at least one movement of the rotational movement and the linear movement of the at least one of the plurality of blades.

2. The X-ray imaging apparatus according to claim 1, wherein the at least one processor is configured to determine validity of the input points.

3. The X-ray imaging apparatus according to claim 2, wherein, in response to receiving an input point, the at least one processor is configured to determine validity of the input point, and if the at least one processor determines that the input point is invalid, the at least one processor is configured to display a result of that the input point is invalid through the display.

4. The X-ray imaging apparatus according to claim 2, wherein when a distance between a first input point and a second input point among the input points is less than a reference value, the at least one processor is configured to determine that an input point that is last input among the first input point and the second input point is invalid.

5. The X-ray imaging apparatus according to claim 2, wherein when at least three input points of the input points are located on a straight line, the at least one processor is configured to determine that an input point that is last input among the at least three input points is invalid.

6. The X-ray imaging apparatus according to claim 2, wherein when a figure defined by the input points has a concave shape, the at least one processor is configured to determine that an input point that is last input among the input points is invalid.

7. The X-ray imaging apparatus according to claim 6, wherein the at least one processor is configured to determine whether the figure defined by the input points has the concave shape based on whether an order in which a lastly input point among the input points is connected with previously input points is in a clockwise order or a counterclockwise order.

8. The X-ray imaging apparatus according to claim 2, wherein when the at least one processor determines that an input point among the input points is invalid, the input device is configured to receive a new input point that replaces the input point that is determined to be invalid.

9. The X-ray imaging apparatus according to claim 2, wherein when the at least one processor determines that all of the input points are valid, the at least one processor is configured to connect the input points to define the window area in a shape of the polygon.

10. The X-ray imaging apparatus according to claim 1, wherein the guide image includes at least one image among an X-ray image acquired by irradiating a low dose of X-rays on an object before main scanning, a camera image acquired by photographing the object with a camera, and a previously acquired X-ray image of the object.

11. The X-ray imaging apparatus according to claim 10, wherein when the at least one processor is configured to acquire an X-ray image corresponding to the collimation area of the shape most similar to the polygon defined by the input points, and to perform image processing on the acquired X-ray image.

12. The X-ray imaging apparatus according to claim 11, wherein the at least one processor is configured to perform the image processing in such a way to reduce brightness or definition of a remaining area except for the window area in the acquired X-ray image or to cut off the remaining area.

13. An X-ray imaging apparatus comprising:
    a collimator including a plurality of blades to form a collimation area, wherein at least one blade of the plurality of blades is rotatable in a clockwise direction or in a counterclockwise direction;
    a display configured to display a guide image;
    an input device configured to receive n number of a point for the guide image, the n number of the point input by a user, wherein n is an integer that is equal to or greater than 1; and
    at least one processor configured to set a circle defined by the n number of the point to a window area, to control the collimator to form a collimation area in a shape of a polygon including to the window area, and to perform image processing on an X-ray image acquired by X-rays passed through the collimation area to acquire an X-ray image corresponding to the window area,
    wherein, in response to determining that the collimator cannot form a collimation area having a shape of the circle defined by the n number of the point, the at least one processor is configured to control the collimator to form the collimation area in a shape of a square of which one side has a length equal to a diameter of the circle defined by the n number of the point.

14. The X-ray imaging apparatus according to claim 13, wherein when two points are input through the input device, the at least one processor is configured to set a circle whose diameter or radius is a straight line connecting the two points, to the window area.

15. The X-ray imaging apparatus according to claim 13, wherein when a point and a straight line starting from the point are input through the input device, the at least one processor is configured to set a circle whose center point is the point and whose radius is the straight line, to the window area.

16. The X-ray imaging apparatus according to claim 13, wherein when a point and a straight line starting from the point are input through the input device, the at least one processor is configured to set a circle whose diameter is the straight line, to the window area.

17. The X-ray imaging apparatus according to claim 13, wherein when a point is input through the input device, the at least one processor is configured to create a circle whose center point is the point input through the input device, and increase a radius of the circle in proportion to a time period for which the point is input.

18. The X-ray imaging apparatus according to claim 17, wherein the at least one processor is configured to set a circle having a radius acquired at time at which the point is no longer input, to the window area.

19. The X-ray imaging apparatus according to claim 13, wherein the plurality of blades are configured to perform at least one movement of a rotational movement and a linear movement.

20. The X-ray imaging apparatus according to claim 13, wherein the at least one processor is further configured to perform shutter processing on a remaining area in the acquired X-ray image except for an area occupied by the circle by the n number of the point or cut off the remaining area, to generate an X-ray image corresponding to the window area.

21. A method of controlling an X-ray imaging apparatus, comprising:
    displaying a guide image on a display;
    receiving n number of input points for the guide image from a user, wherein n is an integer that is equal to or greater than 3; and
    setting a polygon defined by the n number of input points to a window area, and controlling a collimator including a plurality of blades to form a collimation area corresponding to the window area, wherein at least one blade of the plurality of blades is rotatable in a clockwise direction or in a counterclockwise direction,
    wherein the controlling the collimator comprises:
        controlling the collimator to form a collimation area having a shape of the polygon defined by the n number of input points, the collimator controlled to perform at least one movement of a rotational movement and a linear movement of at least one of the plurality of blades to place intersection points of the plurality of blades at locations of the n number of input points, respectively; and
        controlling the collimator to form a collimation area of a shape most similar to the polygon defined by the n number of input points, in response to determining that the intersection points of the plurality of blades cannot be placed at the locations of the n number of input points, respectively, by any of the at least one movement of the rotational movement and the linear movement of the at least one of the plurality of blades.

22. The method according to claim 21, wherein the controlling of the collimator to form the collimation area of the shape most similar to the polygon defined by the n number of input points comprises:
    acquiring an X-ray image corresponding to the collimation area of the shape most similar to the polygon defined by the n number of input points, and
    controlling the collimator to perform image processing on an acquired X-ray image.

23. A method of controlling an X-ray imaging apparatus, comprising:
    displaying a guide image on a display;
    receiving n number of a point for the guide image, the n number of the point input by a user, wherein n is an integer that is equal to or greater than 1; and
    setting a circle defined by the n number of the point to a window area;
    controlling a collimator including a plurality of blades to form a collimation area in a shape of a polygon including the window area, wherein at least one blade of the plurality of blades is configured to be rotatable in a clockwise direction or in a counterclockwise direction;
    in response to determining that the collimator cannot form a collimation area having a shape of the circle defined by the n number of the point, controlling the collimator to form the collimation area in a shape of a square of which one side has a length equal to a diameter of the circle defined by the n number of the point; and
    performing image processing on an X-ray image acquired by X-rays passed through the collimation area to acquire an X-ray image corresponding to the window area.

24. The method according to claim 23, wherein the performing the image processing comprises performing shutter processing on a remaining area in the acquired X-ray image except for an area occupied by the circle by the n number of the point or cutting off the remaining area, to generate an X-ray image corresponding to the window area.

* * * * *